US012297486B2

(12) United States Patent
Patterson et al.

(10) Patent No.: US 12,297,486 B2
(45) Date of Patent: *May 13, 2025

(54) METHODS FOR SPATIAL ANALYSIS USING PROXIMITY LIGATION

(71) Applicant: 10x Genomics, Inc., Pleasanton, CA (US)

(72) Inventors: David Michael Patterson, Oakland, CA (US); Sultan Doganay Tuncer, Danville, CA (US); Zachary Bent, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/991,309

(22) Filed: Nov. 21, 2022

(65) Prior Publication Data

US 2023/0077364 A1 Mar. 16, 2023

Related U.S. Application Data

(63) Continuation of application No. 17/155,764, filed on Jan. 22, 2021.

(60) Provisional application No. 63/043,459, filed on Jun. 24, 2020, provisional application No. 62/965,612, filed on Jan. 24, 2020.

(51) Int. Cl.
| | |
|---|---|
| *C12Q 1/68* | (2018.01) |
| *C12N 9/00* | (2006.01) |
| *C12N 9/12* | (2006.01) |
| *C12Q 1/6813* | (2018.01) |
| *C12Q 1/6837* | (2018.01) |
| *C12Q 1/6844* | (2018.01) |

(52) U.S. Cl.
CPC ......... *C12Q 1/6837* (2013.01); *C12N 9/1241* (2013.01); *C12N 9/93* (2013.01); *C12Q 1/6813* (2013.01); *C12Q 1/6844* (2013.01); *C12Y 207/07* (2013.01); *C12Y 600/00* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,800,159 A | 1/1989 | Mullis | |
| 4,883,867 A | 11/1989 | Lee | |
| 4,965,188 A | 10/1990 | Mullis | |
| 4,988,617 A | 1/1991 | Landegren et al. | |
| 5,002,882 A | 3/1991 | Lunnen | |
| 5,130,238 A | 7/1992 | Malek | |
| 5,308,751 A | 5/1994 | Ohkawa | |
| 5,321,130 A | 6/1994 | Yue | |
| 5,410,030 A | 4/1995 | Yue | |
| 5,436,134 A | 7/1995 | Haugland | |
| 5,455,166 A | 10/1995 | Walker | |
| 5,494,810 A | 2/1996 | Barany et al. | |
| 5,503,980 A | 4/1996 | Cantor | |
| 5,512,439 A | 4/1996 | Hornes | |
| 5,512,462 A | 4/1996 | Cheng | |
| 5,582,977 A | 12/1996 | Yue | |
| 5,599,675 A | 2/1997 | Brenner | |
| 5,641,658 A | 6/1997 | Adams | |
| 5,648,245 A | 7/1997 | Fire et al. | |
| 5,658,751 A | 8/1997 | Yue | |
| 5,695,940 A | 12/1997 | Drmanac et al. | |
| 5,750,341 A | 5/1998 | Macevicz | |
| 5,763,175 A | 6/1998 | Brenner | |
| 5,830,711 A | 11/1998 | Barany et al. | |
| 5,837,832 A | 11/1998 | Chee et al. | |
| 5,854,033 A | 12/1998 | Lizardi | |
| 5,863,753 A | 1/1999 | Haugland | |
| 5,871,921 A | 2/1999 | Landegren et al. | |
| 5,912,148 A | 6/1999 | Eggerding | |
| 5,925,545 A | 7/1999 | Reznikoff et al. | |
| 5,928,906 A | 7/1999 | Koester et al. | |
| 5,958,775 A | 9/1999 | Wickstrrom | |
| 5,962,271 A | 10/1999 | Chenchik et al. | |
| 5,962,272 A | 10/1999 | Chenchik et al. | |
| 5,965,443 A | 10/1999 | Reznikoff et al. | |
| 6,013,440 A | 1/2000 | Lipshutz | |
| 6,027,889 A | 2/2000 | Barany et al. | |
| 6,054,274 A | 4/2000 | Sampson et al. | |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Appella, "Non-natural nucleic acids for synthetic biology," Current Opinion in Chemical Biology, Dec. 2009, 13(5-6): 687-696.
Bunt et al., "FRET from single to multiplexed signaling events," Biophys Rev. Apr. 2017, 9(2): 119-129.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Ma et al., "Isothermal amplification method for next-generation sequencing," PNAS, Aug. 12, 2013, 110(35):14320-14323.
O'Huallachain et al., "Ultra-high throughput single-cell analysis of proteins and RNAs by split-pool synthesis," Communications Biology, 2020, 3:213, 19 pages.

(Continued)

*Primary Examiner* — Suryaprabha Chunduru
(74) *Attorney, Agent, or Firm* — Fish & Richardson P.C.

(57) ABSTRACT

The present disclosure provides methods and compositions for detecting and spatially locating analyte interactions and gene expression in a biological sample. For example, provided herein are methods of determining a location of at least one analyte in a biological sample using analyte-binding moieties, proximity ligation, and an array including capture probes.

28 Claims, 23 Drawing Sheets

(56) References Cited

U.S. PATENT DOCUMENTS

| | | |
|---|---|---|
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,492 B2 | 10/2009 | Fu et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,343,500 B2 | 1/2013 | Wraith |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |

(56) References Cited

U.S. PATENT DOCUMENTS

| | | |
|---|---|---|
| 9,376,719 B2 | 6/2016 | Eijk |
| 9,404,156 B2 | 8/2016 | Hicks |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,950 B2 | 2/2018 | Church et al. |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,011,872 B1 | 7/2018 | Belgrader et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,266,876 B2 | 4/2019 | Cai et al. |
| 10,267,808 B2 | 4/2019 | Cai |
| 10,273,541 B2 | 4/2019 | Hindson et al. |
| 10,308,982 B2 | 6/2019 | Chee |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,428,326 B2 | 10/2019 | Belhocine et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,662,468 B2 | 5/2020 | Chee |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,872,679 B2 | 12/2020 | Cai et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,001,879 B1 | 5/2021 | Chee |
| 11,008,607 B2 | 5/2021 | Chee |
| 11,008,608 B2 | 5/2021 | Samusik et al. |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,214,796 B2 | 1/2022 | Shirai et al. |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,459,607 B1 | 10/2022 | Terry et al. |
| 11,479,809 B2 | 10/2022 | Frisen et al. |
| 11,479,810 B1 | 10/2022 | Chee |
| 11,492,612 B1 | 11/2022 | Dadhwal |
| 11,501,440 B2 | 11/2022 | Weisenfeld et al. |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,519,138 B2 | 12/2022 | Meier et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,713,480 B2 | 8/2023 | Lee |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |

(56) References Cited

U.S. PATENT DOCUMENTS

| | | |
|---|---|---|
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 11,981,958 B1 | 5/2024 | Galonska |
| 11,981,960 B1 | 5/2024 | Lin et al. |
| 11,981,965 B2 | 5/2024 | Chell et al. |
| RE50,065 E | 7/2024 | Frisen et al. |
| 12,024,741 B2 | 7/2024 | Tentori et al. |
| 12,031,177 B1 | 7/2024 | Tentori et al. |
| 12,060,604 B2 | 8/2024 | Katiraee et al. |
| 12,071,655 B2 | 8/2024 | Sukovich et al. |
| 12,076,701 B2 | 9/2024 | Bava |
| 12,098,417 B2 | 9/2024 | Engblom et al. |
| 12,098,985 B2 | 9/2024 | Cox et al. |
| 12,110,541 B2 | 10/2024 | Bava |
| 12,117,439 B2 | 10/2024 | Delaney et al. |
| 12,128,403 B2 | 10/2024 | Kim et al. |
| 12,129,516 B2 | 10/2024 | Tentori et al. |
| 12,157,124 B2 | 12/2024 | Cox et al. |
| 12,180,543 B2 | 12/2024 | Uytingco et al. |
| 12,195,790 B2 | 1/2025 | Sukovich et al. |
| 12,203,134 B2 | 1/2025 | Nagendran et al. |
| 12,209,280 B1 | 1/2025 | Mignardi et al. |
| D1,064,308 S | 2/2025 | Alimsijah et al. |
| 12,223,751 B2 | 2/2025 | Li et al. |
| 12,228,544 B2 | 2/2025 | Kim et al. |
| 12,234,505 B2 | 2/2025 | Chee |
| 12,241,060 B2 | 3/2025 | Kim et al. |
| 12,241,890 B2 | 3/2025 | Delaney et al. |
| 12,249,085 B2 | 3/2025 | Tentori et al. |
| 2001/0055764 A1 | 12/2001 | Empendocles et al. |
| 2002/0040275 A1 | 4/2002 | Cravatt |
| 2002/0048766 A1 | 4/2002 | Doyle et al. |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0087232 A1 | 5/2003 | Christians |
| 2003/0092624 A1 | 5/2003 | Wang et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0019005 A1 | 1/2004 | Van Ness |
| 2004/0033499 A1 | 2/2004 | Ilsley et al. |
| 2004/0067492 A1 | 4/2004 | Peng et al. |
| 2004/0067493 A1 | 4/2004 | Matsuzaki |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0224326 A1 | 11/2004 | Kim et al. |
| 2004/0235103 A1 | 11/2004 | Reznikoff et al. |
| 2004/0241660 A1 | 12/2004 | Wojtowicz et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0118602 A1 | 6/2005 | Li et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0170373 A1 | 8/2005 | Monforte |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0041385 A1 | 2/2006 | Bauer et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0153086 A1 | 6/2008 | Wong |
| 2008/0160580 A1 | 7/2008 | Adessi et al. |
| 2008/0220434 A1 | 9/2008 | Thomas |

(56) References Cited

U.S. PATENT DOCUMENTS

| | | |
|---|---|---|
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0011943 A1 | 1/2009 | Drmanac et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0270273 A1 | 10/2009 | Burns et al. |
| 2009/0283407 A1 | 11/2009 | Van Eijk |
| 2009/0286249 A1 | 11/2009 | Bekcer et al. |
| 2009/0289184 A1 | 11/2009 | Deininger |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120043 A1 | 5/2010 | Sood et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Fan et al. |
| 2011/0223613 A1 | 9/2011 | Gut |
| 2011/0245101 A1 | 10/2011 | Chee et al. |
| 2011/0245111 A1 | 10/2011 | Chee |
| 2011/0269647 A1* | 11/2011 | Ule .................. C12N 15/1093 |
| | | 435/6.19 |
| 2011/0287435 A1 | 11/2011 | Grunenwald et al. |
| 2012/0010091 A1 | 1/2012 | Linnarson |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0040842 A1 | 2/2013 | Lim et al. |
| 2013/0065768 A1 | 3/2013 | Zheng et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0065609 A1 | 3/2014 | Hicks et al. |
| 2014/0066318 A1 | 3/2014 | Frisen et al. |
| 2014/0099637 A1 | 4/2014 | Nolan et al. |
| 2014/0121118 A1 | 5/2014 | Warner |
| 2014/0155295 A1 | 6/2014 | Hindson et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0132743 A1 | 5/2015 | Egidio et al. |
| 2015/0148239 A1* | 5/2015 | Peter .................. C12Q 1/6841 |
| | | 506/3 |
| 2015/0292988 A1 | 10/2015 | Bharadwaj et al. |
| 2015/0298091 A1 | 10/2015 | Weitz et al. |
| 2015/0344942 A1* | 12/2015 | Frisen .................. C12Q 1/6841 |
| | | 506/30 |
| 2015/0368704 A1 | 12/2015 | Fan et al. |
| 2016/0019337 A1 | 1/2016 | Roberts et al. |
| 2016/0024576 A1 | 1/2016 | Chee |
| 2016/0032282 A1 | 2/2016 | Vigneault et al. |
| 2016/0041159 A1 | 2/2016 | Labaer et al. |
| 2016/0060687 A1* | 3/2016 | Zhu .................. G01N 33/5308 |
| | | 506/31 |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289669 A1 | 10/2016 | Fan et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0283860 A1 | 4/2017 | Kool et al. |
| 2017/0159109 A1 | 6/2017 | Zheng et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0242020 A1 | 8/2017 | Yamauchi et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0343545 A1 | 11/2017 | Hadrup et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0088112 A1 | 3/2018 | Fan et al. |
| 2018/0094316 A1 | 4/2018 | Oliphant et al. |
| 2018/0105808 A1 | 4/2018 | Mikkelsen et al. |
| 2018/0112209 A1 | 4/2018 | Eshoo |
| 2018/0112212 A1 | 4/2018 | Nicol et al. |
| 2018/0112261 A1 | 4/2018 | Van Driel et al. |
| 2018/0114316 A1 | 4/2018 | Lele et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1* | 7/2018 | Larman .................. C12Q 1/68 |
| 2018/0216161 A1 | 8/2018 | Chen et al. |
| 2018/0216162 A1 | 8/2018 | Belhocine et al. |
| 2018/0237864 A1 | 8/2018 | Imler et al. |

(56) References Cited

U.S. PATENT DOCUMENTS

| | | |
|---|---|---|
| 2018/0245142 A1 | 8/2018 | So et al. |
| 2018/0247017 A1 | 8/2018 | van Eijk et al. |
| 2018/0251825 A1 | 9/2018 | Stoeckius et al. |
| 2018/0282803 A1 | 10/2018 | Belgrader et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2018/0334670 A1 | 11/2018 | Bharadwaj et al. |
| 2018/0346970 A1 | 12/2018 | Chang |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085324 A1 | 3/2019 | Regev et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0144936 A1 | 5/2019 | Gierahn et al. |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218607 A1 | 7/2019 | Love et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0276880 A1 | 9/2019 | Fan et al. |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0352708 A1 | 11/2019 | Gaige et al. |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0002764 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0217850 A1 | 7/2020 | Liu et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |

(56) References Cited

U.S. PATENT DOCUMENTS

| | | |
|---|---|---|
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0315984 A1 | 10/2022 | Edelman et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403374 A1 | 12/2022 | Soumillon |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0416807 A1 | 1/2023 | Chee |
| 2023/0416808 A1 | 1/2023 | Sukovich et al. |
| 2023/0031305 A1 | 2/2023 | Hernandez Neuta et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0212656 A1 | 7/2023 | Chow et al. |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0267625 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304072 A1 | 9/2023 | Gohil et al. |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0351619 A1 | 11/2023 | Tentori et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |
| 2024/0182968 A1 | 6/2024 | Bava |
| 2024/0191286 A1 | 6/2024 | Boutet et al. |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |

(56) References Cited

U.S. PATENT DOCUMENTS

| | | |
|---|---|---|
| 2024/0219701 A1 | 7/2024 | Tentori et al. |
| 2024/0253036 A1 | 8/2024 | Kim et al. |
| 2024/0263218 A1 | 8/2024 | Katiraee et al. |
| 2024/0271190 A1 | 8/2024 | Stoeckius et al. |
| 2024/0271195 A1 | 8/2024 | Mikhaiel et al. |
| 2024/0279747 A1 | 8/2024 | Williams |
| 2024/0287600 A1 | 8/2024 | Iyer et al. |
| 2024/0294971 A1 | 9/2024 | Galonska |
| 2024/0294974 A1 | 9/2024 | Galonska et al. |
| 2024/0294975 A1 | 9/2024 | Lin et al. |
| 2024/0301488 A1 | 9/2024 | Stoeckius |
| 2024/0301489 A1 | 9/2024 | Chew et al. |
| 2024/0360494 A1 | 10/2024 | Costa et al. |
| 2024/0368711 A1 | 11/2024 | Giacomello et al. |
| 2024/0377297 A1 | 11/2024 | Cox et al. |
| 2024/0385088 A1 | 11/2024 | Kim et al. |
| 2024/0392349 A1 | 11/2024 | Frisen et al. |
| 2024/0392351 A1 | 11/2024 | Chee |
| 2024/0392352 A1 | 11/2024 | Stahl et al. |
| 2024/0392353 A1 | 11/2024 | Engblom et al. |
| 2024/0401109 A1 | 12/2024 | Kim et al. |
| 2024/0401117 A1 | 12/2024 | Bava |
| 2024/0401118 A1 | 12/2024 | Tentori et al. |
| 2024/0404301 A1 | 12/2024 | Li et al. |
| 2024/0408593 A1 | 12/2024 | Kim et al. |
| 2024/0416315 A1 | 12/2024 | Bava |
| 2024/0417783 A1 | 12/2024 | Chew et al. |
| 2024/0417784 A1 | 12/2024 | Sukovich et al. |
| 2025/0002980 A1 | 1/2025 | Tentori et al. |
| 2025/0002982 A1 | 1/2025 | Stoeckius et al. |
| 2025/0003956 A1 | 1/2025 | Delaney et al. |
| 2025/0019689 A1 | 1/2025 | Galonska et al. |
| 2025/0019749 A1 | 1/2025 | Katiraee et al. |
| 2025/0066762 A1 | 2/2025 | Man et al. |
| 2025/0066770 A1 | 2/2025 | Costa |
| 2025/0073719 A1 | 3/2025 | Cox et al. |
| 2025/0075261 A1 | 3/2025 | Kim |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2130913 | 12/2009 |
| EP | 2292788 | 3/2011 |
| EP | 2302070 | 3/2011 |
| EP | 2881465 | 6/2015 |
| EP | 3013984 | 5/2016 |
| EP | 3207134 | 7/2019 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| RU | 2270254 | 2/2006 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/017390 | 3/2000 |
| WO | WO 2000/024940 | 5/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/024952 | 3/2002 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/117541 | 11/2006 |
| WO | WO 2006/124771 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/022332 | 2/2008 |
| WO | WO 2008/069906 | 6/2008 |
| WO | WO 2008/075086 | 6/2008 |
| WO | WO 2009/032167 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2011/008502 | 1/2011 |
| WO | WO 2011/062933 | 5/2011 |
| WO | WO 2011/068088 | 6/2011 |
| WO | WO 2011/094669 | 8/2011 |
| WO | WO 2012/048341 | 4/2012 |
| WO | WO 2012/049316 | 4/2012 |
| WO | WO 2012/061832 | 5/2012 |
| WO | WO 2012/071428 | 5/2012 |
| WO | WO 2012/083225 | 6/2012 |
| WO | WO 2012/129242 | 9/2012 |
| WO | WO 2012/159089 | 11/2012 |
| WO | WO 2013/022807 | 2/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/201273 | 12/2014 |
| WO | WO 2014/210223 | 12/2014 |
| WO | WO 2014/210225 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2015/168161 | 11/2015 |
| WO | WO 2015/188839 | 12/2015 |
| WO | WO 2016/040476 | 3/2016 |
| WO | WO 2016/057552 | 4/2016 |

(56) References Cited

FOREIGN PATENT DOCUMENTS

| | | |
|---|---|---|
| WO | WO 2016/077763 | 5/2016 |
| WO | WO 2016/100196 | 6/2016 |
| WO | WO 2016/126871 | 8/2016 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/013170 | 1/2017 |
| WO | WO 2017/019456 | 2/2017 |
| WO | WO 2017/019481 | 2/2017 |
| WO | WO 2017/044993 | 3/2017 |
| WO | WO 2017/075265 | 5/2017 |
| WO | WO 2017/075293 | 5/2017 |
| WO | WO 2017/096158 | 7/2017 |
| WO | WO 2017/143155 | 8/2017 |
| WO | WO 2017/147483 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/075693 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO-2018175779 A1 * | 9/2018 ............ C12N 15/11 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/104337 | 5/2019 |
| WO | WO 2019/113457 | 6/2019 |
| WO | WO 2019/113533 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/077236 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/227309 | 11/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/032195 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2011/019964 | 6/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |

(56) References Cited

FOREIGN PATENT DOCUMENTS

| WO | WO 2023/250077 | 12/2023 |
|---|---|---|
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |

OTHER PUBLICATIONS

Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Satija et al., "Spatial reconstruction of single-cell gene expression data," Nature, Apr. 13, 2015, 33(5):495-402, 14 pages.
Stoeckius et al., "Simultaneous epitope and transcriptome measurement in single cells," Nature Methods, Jul. 31, 2017, 14(9):865-868.
U.S. Appl. No. 16/353,937, filed Mar. 14, 2019, Frisen et al.
U.S. Appl. No. 17/707,189, filed Mar. 29, 2022, Chell et al.
U.S. Appl. No. 60/416,118, filed Oct. 3, 2002, Fan et al.
U.S. Appl. No. 61/267,363, filed Dec. 7, 2009, Fan et al.
U.S. Appl. No. 63/033,348, filed Jun. 2, 2020, Bent.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.
Adamson et al., "A Multiplexed Single-Cell CRISPR Screening Platform Enables Systematic Dissection of the Unfolded Protein Response," Cell, Dec. 2016, 167(7):1867-1882.e21.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples, " Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Andresen et al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes—Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Azioune et al., "Simple and rapid process for single cell micropatterning," Lab Chip, Jun. 2009, 9(11):1640-1642.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.

(56) References Cited

OTHER PUBLICATIONS

Banerjee et al., "Viral glycoproteins: biological role and application in diagnosis," Virusdisease, Mar. 2016, 27(1):1-11.

Barnes, "PCR amplification of up to 35-kb DNA with high fidelity and high yield from lambda bacteriophage templates," Proc. Natl. Acad. Sci USA, 1994, 91(6):2216-2220.

Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.

Bartosovic et al., "Single-cell CUT&Tag profiles histone modifications and transcription factors in complex tissues," Nat Biotechnol., Jul. 2021, 39(7):825-835, Abstract.

Baugh et al., "Quantitative analysis of mRNA amplification by in vitro transcription," Nucleic Acids Res., 2001, 29(5):e29, 9 pages.

Beattie et al., "Advances in genosensor research," Clin Chem., May 1995, 41(5):700-6.

Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.

Bell, "A simple way to treat PCR products prior to sequencing using ExoSAP-IT," Biotechniques, 2008, 44(6):834, 1 page.

Bentley et al., "Accurate whole human genome sequencing using reversible terminator chemistry," Nature, 2008, 456(7218):53-59.

Bergenstråhle et al., "Seamless integration of image and molecular analysis for spatial transcriptomics workflows," BMC Genomics, Jul. 2020, 21(1):482, 7 pages.

Berger et al., "Universal bases for hybridization, replication and chain termination," Nucleic Acid Res., Aug. 2000, 28(15):2911-2914.

Bielas et al., "Quantification of random genomic mutations," Nat. Methods, 2005, 2(4):285-290.

Biosyntagma.com, [online], "Resolving Heterogeneity One Cell at a Time," available on or before Apr. 21, 2017, via Internet Archive: Wayback Machine URL<https://web.archive.org/web/20170421212315/http:/www.biosyntagma.com/>, retrieved on Sep. 29, 2021, URL<http://www.biosyntagma.com/>, 3 pages.

Birney et al., "Identification and analysis of functional elements in 1% of the human genome by the Encode pilot project," Nature, 2007, 447(7146):799-816.

Blair et al., "Microarray temperature optimization using hybridization kinetics," Methods Mol Biol., 2009, 529:171-96.

Blanchard et al., "High-density oligonucleotide arrays," Biosensors & Bioelectronics, 1996, 11(6-7):687-690.

Blanco et al., "A practical approach to FRET-based PNA fluorescence in situ hybridization," Methods, Dec. 2010, 52(4):343-51.

Blokzijl et al., "Profiling protein expression and interactions: proximity ligation as a tool for personalized medicine," J Intern. Med., 2010, 268(3):232-245.

Blow, "Tissue Issues," Nature, 2007, 448(7156):959-962.

Bolognesi et al., "Multiplex Staining by Sequential Immunostaining and Antibody Removal on Routine Tissue Sections," J. Histochem. Cytochem., Aug. 2017, 65(8):431-444.

Bolotin et al., "MiXCR: software for comprehensive adaptive immunity profiling," Nat Methods., May 2015, 12(5):380-1.

Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).

Boulé et al., "Terminal deoxynucleotidyl transferase indiscriminately incorporates ribonucleotides and deoxyribonucleotides," J Biol Chem., Aug. 2001, 276(33):31388-93.

Brandon et al., "Mitochondrial mutations in cancer," Oncogene, 2006, 25(34):4647-4662.

Brenner et al., "Gene expression analysis by massively parallel signature sequencing (MPSS) on microbead arrays," Nat. Biotech., 2000, 18(6):630-634.

Brenner et al., "In vitro cloning of complex mixtures of DNA on microbeads: physical separation of differentially expressed cDNAs," Proc. Natl. Acad. Sci. USA, 2000, 97(4):1665-1670.

Brow, "35—The Cleavase I enzyme for mutation and polymorphism scanning," PCR Applications Protocols for Functional Genomics, 1999, pp. 537-550.

Brown et al., "Retroviral integration: structure of the initial covalent product and its precursor, and a role for the viral IN protein," Proc Natl Acad Sci USA, Apr. 1989, 86(8):2525-9.

Buenrostro et al., "Transposition of native chromatin for multimodal regulatory analysis and personal epigenomics," Nat Methods, Dec. 2013, 10(12):1213-1218.

Bullard et al., "Direct comparison of nick-joining activity of the nucleic acid ligases from bacteriophage T4," Biochem. J. 2006, 398(1):135-144.

Burgess, "A space for transcriptomics," Nature Reviews Genetics, 2016, 17(8):436-7.

Burgess, "Finding structure in gene expression," Nature Reviews Genetics, 2018, 19(5):249, 1 page.

Burgess, "Spatial transcriptomics coming of age," Nat Rev Genet., Jun. 2019, 20(6):317, 1 page.

Burton et al., "Coverslip Mounted-Immersion Cycled in Situ RT-PCR for the Localization of mRNA in Tissue Sections," Biotechniques, 1998, 24(1):92-100.

Butler et al., "Integrating single-cell transcriptomic data across different conditions, technologies, and species," Nat Biotechnol., Jun. 2018, 36(5):411-420.

Caliari et al., "A practical guide to hydrogels for cell culture," Nat Methods., Apr. 2016, 13(5):405-14.

Cha et al., "Specificity, efficiency, and fidelity of PCR," Genome Res., 1993, 3(3):S18-29.

Chandra et al., "Cell-free synthesis-based protein microarrays and their applications," Proteomics, 2009, 5(6):717-30.

Chatterjee et al., "Mitochondrial DNA mutations in human cancer. Oncogene," 2006, 25(34):4663-4674.

Chen et al., "ATAC-see reveals the accessible genome by transposase-mediated imaging and sequencing," Nature Methods, Dec. 2016, 13(12):1013-1020.

Chen et al., "DNA hybridization detection in a microfluidic Channel using two fluorescently labelled nucleic acid probes," Biosensors and Bioelectronics, 2008, 23(12):1878-1882.

Chen et al., "Efficient in situ barcode sequencing using padlock probe-based BaristaSeq," Nucleic Acids Res., 2018, 46(4): e22, 11 pages.

Chen et al., "Expansion microscopy," Science, 2015, 347(6221):543-548.

Chen et al., "Geometric control of cell life and death," Science, May 1997, 276(5317):1425-1428.

Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.

Chen et al., "Nanoscale imaging of RNA with expansion microscopy," Nat Methods, Aug. 2016, 13(8):679-84.

Chen et al., "Parallel single nucleotide polymorphism genotyping by surface invasive cleavage with universal detection," Anal Chem., Apr. 2005, 77(8):2400-5.

Chen et al., "RNA imaging. Spatially resolved, highly multiplexed RNA profiling in single cells," Science, Apr. 2015, 348(6233):aaa6090, 21 pages.

Chen et al., "Spatial Transcriptomics and In Situ Sequencing to Study Alzheimer's Disease," Cell, Aug. 2020, 182(4):976-991.

Chen et al., "Spatially resolved, highly multiplexed RNA profiling in single cells," Science, 2015, 348(6233):aaa6090, 21 pages.

Chen et al., "µCB-seq: microfluidic cell barcoding and sequencing for high-resolution imaging and sequencing of single cells," Lab Chip, Nov. 2020, 20(21):3899-3913.

Cheng et al., "Sensitive Detection of Small Molecules by Competitive Immunomagnetic-Proximity Ligation Assay," Anal Chem, 2012, 84:2129-2132.

Chester et al., "Dimethyl sulfoxide-mediated primer Tm reduction: a method for analyzing the role of renaturation temperature in the polymerase chain reaction," Anal Biochem, Mar. 1993, 209(2):284-90.

Chrisey et al., "Covalent attachment of synthetic DNA to self-assembled monolayer films," Nucleic Acids Res., Aug. 1996, 24(15):3031-9.

(56) References Cited

OTHER PUBLICATIONS

Chung et al., "Imaging single-cell signaling dynamics with a deterministic high-density single-cell trap array," Anal Chem, Sep. 2011, 83(18):7044-7052.
Chung et al., "Structural and molecular interrogation of intact biological systems," Nature, May 2013, 497:332-337.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Collins et al., "Two-dimensional single-cell patterning with one cell per well driven by surface acoustic waves," Nature Communications, Nov. 2015, 6:8686, 11 pages.
Constantine et al., "Use of genechip high-density oligonucleotide arrays for gene expression monitoring, " Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Corces et al., "Lineage-specific and single-cell chromatin accessibility charts human hematopoiesis and leukemia evolution," Nature Genetics, Oct. 2016, 48(10):1193-1203.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Datlinger et al., "Pooled CRISPR screening with single-cell transcriptome readout," Nat Methods, Mar. 2017, 14(3):297-301.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
DePasquale et al., "DoubletDecon: Deconvoluting Doublets from Single-Cell RNA-Sequencing Data," Cell Rep., Nov. 5, 2019, 29(6):1718-1727.e8, 19 pages.
Ding et al., "On-chip manipulation of single microparticles, cells, and organisms using surface acoustic waves," PNAS, Jul. 2012, 109(28):11105-11109.
Dixit et al., "Perturb-Seq: Dissecting Molecular Circuits with Scalable Single-Cell RNA Profiling of Pooled Genetic Screens," Cell, Dec. 2016, 167(7):1853-1866.e17.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine et al., "Analysis of gene expression in single live neurons," Proc. Natl. Acad. Sci., USA 89, 3010-3014, 1992.
Eberwine, "Amplification of mRNA populations using aRNA generated from immobilized oligo(dT)-T7 primed cDNA, "BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Evers et al., "The effect of formaldehyde fixation on RNA: optimization of formaldehyde adduct removal," J Mol Diagn., May 2011, 13(3):282-8.
Falconnet et al., "Surface engineering approaches to micropattern surfaces for cell-based assays," Biomaterials, Jun. 2006, 27(16):3044-3063.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Folch et al., "Microfabricated elastomeric stencils for micropatterning cell cultures," J Biomed Mater Res, Nov. 2000, 52(2):346-353.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.

(56) References Cited

OTHER PUBLICATIONS

Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.
Gaucherand et al., "The Influenza A Virus Endoribonuclease PA-X Usurps Host mRNA Processing Machinery to Limit Host Gene Expression," Cell Reports, Apr. 2019, 27(3):776-792.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Giam et al., "Scanning probe-enabled nanocombinatorics define the relationship between fibronectin feature size and stem cell fate," PNAS, Mar. 2012, 109(12):4377-4382.
Gierahn et al., "Seq-Well: portable, low-cost RNA sequencing of single cells at high throughput," ResearchSquare, 2017, 53 pages.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grant et al., "Pathways and mechanisms of endocytic recycling," Nat. Rev. Mol. Cell Biol., Sep. 2009, 10(9):597-608.
Grokhovsky, "Specificity of DNA cleavage by ultrasound," Molecular Biology, 2006, 40(2):276-283.
Gross et al., "Technologies for Single-Cell Isolation," Int. J Mol. Sci., Jul. 2015, 16(8):16897-16919.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Habib et al., "Div-Seq: Single-nucleus RNA-Seq reveals dynamics of rare adult newborn neurons," Science, Aug. 2016, 353(6302):925-8.
Habib et al., "Massively parallel single-nucleus RNA-seq with DroNc-seq," Nat Methods, Oct. 2017, 14(10):955-958.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hammond et al., "Profiling cellular protein complexes by proximity ligation with dual tag microarray readout," PLoS One, 2012, 7(7):e40405, 9 pages.
Han et al., "3C and 3C-based techniques: the powerful tools for spatial genome organization deciphering", Molecular Cytogenetics (2018) 11: 21, 10 pages, 2018.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Heaton et al., "Souporcell: Robust clustering of single cell RNAseq by genotype and ambient RNA inference without reference genotypes," bioRxiv, Sep. 2019, 22 pages.
Hedskog et al., "Dynamics of HIV-1 Quasispecies during Antiviral Treatment Dissected using Ultra-Deep Pyrosequencing," PLoS One, 5(7): e11345, 2010.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoffman et al., "Formaldehyde crosslinking: a tool for the study of chromatin complexes," J Biol Chem., Oct. 2015, 290(44):26404-11.
Hsuih et al., "Novel, Ligation-Dependent PCR Assay for Detection of Hepatitis C Virus in Serum," Journal of Clinical Microbiology, Mar. 1996, 34(3):501-507.
Hu et al., "Dissecting Cell-Type Composition and Activity-Dependent Transcriptional State in Mammalian Brains by Massively Parallel Single-Nucleus RNA-Seq," Mol Cell., Dec. 2017, 68(5):1006-1015.
Hu et al., "High reproducibility using sodium hydroxide-stripped long oligonucleotide DNA microarrays," Biotechniques, Jan. 2005, 38(1):121-4.
Hughes et al., "Highly Efficient, Massively-Parallel Single-Cell RNA-Seq Reveals Cellular States and Molecular Features of Human Skin Pathology," bioRxiv, Jul. 2019, 51 pages.
Hughes et al., "Microfluidic Western blotting," PNAS, Dec. 2012, 109(52):21450-21455.

(56) References Cited

OTHER PUBLICATIONS

Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.

Ichikawa et al., "In vitro transposition of transposon Tn3," J Biol. Chem., Nov. 1990, 265(31):18829-32, Abstract.

Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.

Jabara et al., Accurate sampling and deep sequencing of the HIV-1 protease gene using a Primer ID. PNAS 108(50); 20166-20171, 2011.

Jaitin et al., "Dissecting Immune Circuits by Linking CRISPR-Pooled Screens with Single-Cell RNA-Seq," Cell, Dec. 2016, 167(7):1883-1896.e15.

Jamur et al., "Permeabilization of cell membranes.," Method Mol. Biol., 2010, 588:63-66.

Jemt et al., "An automated approach to prepare tissue-derived spatially barcoded RNA-sequencing libraries," Scientific Reports, 2016, 6:37137, 10 pages.

Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.

Jones et al., "Comparative lesion sequencing provides insights into tumor evolution," Proc. Natl. Acad. Sci. USA, 105(11): 4283-4288, 2008.

Jucá et al., "Effect of dimethyl sulfoxide on reverse transcriptase activity," Braz. J. Med. Biol. Res., Mar. 1995, 28(3):285-90.

Kalantari et al., "Deparaffinization of formalin-fixed paraffin-embedded tissue blocks using hot water instead of xylene," Anal Biochem., Aug. 2016, 507:71-3.

Kap et al., "Histological assessment of PAXgene tissue fixation and stabilization reagents," PLoS One, 2011, 6:e27704, 10 pages.

Kapteyn et al., "Incorporation of non-natural nucleotides into template-switching oligonucleotides reduces background and improves cDNA synthesis from very small RNA samples," BMC Genomics, Jul. 2010, 11:413, 9 pages.

Karmakar et al., "Organocatalytic removal of formaldehyde adducts from RNA and DNA bases," Nature Chemistry, Aug. 3, 2015, 7(9):752-758.

Kaya-Okur et al., "CUT&Tag for efficient epigenomic profiling of small samples and single cells," Apr. 2019, 10(1):1930, 10 pages.

Ke et al., "In situ sequencing for RNA analysis in preserved tissue and cells," Nat Methods., Sep. 2013, Supplementary Materials, 29 pages.

Kennedy-Darling et al., "Measuring the Formaldehyde Protein-DNA Cross-Link Reversal Rate," Analytical Chemistry, 2014, 86(12):5678-5681.

Kent et al., "Polymerase θ is a robust terminal transferase that oscillates between three different mechanisms during end-joining" Elife, Jun. 2016, 5:e13740, 25 pages.

Kirby et al., "Cryptic plasmids of Mycobacterium avium: Tn552 to the rescue," Mol Microbiol., Jan. 2002, 43(1):173-86.

Kleckner et al., "Tn10 and IS10 transposition and chromosome rearrangements: mechanism and regulation in vivo and in vitro," Curr Top Microbiol Immunol., 1996, 204:49-82.

Korbel et al., "Paired-end mapping reveals extensive structural variation in the human genome," Science, 2007, 318(5849):420-426.

Korsunsky et al., "Fast, sensitive and accurate integration of single-cell data with Harmony," Nat. Methods, Dec. 2019, 16(12):1289-1296.

Kozlov et al., "A highly scalable peptide-based assay system for proteomics," PLoS One, 2012, 7(6):e37441, 10 pages.

Kozlov et al., "A method for rapid protease substrate evaluation and optimization," Comb Chem High Throughput Screen, 2006, 9(6):481-87.

Kristensen et al., "High-Throughput Methods for Detection of Genetic Variation," BioTechniques, Feb. 2001, 30(2):318-332.

Krzywkowski et al., "Chimeric padlock and iLock probes for increased efficiency of targeted RNA detection," RNA, Jan. 2019, 25(1):82-89.

Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.

Kumar et al., "Template-directed oligonucleotide strand ligation, covalent intramolecular DNA circularization and catenation using click chemistry," J Am Chem Soc., May 2007, 129(21):6859-64.

Kurz et al., "cDNA—protein fusions: covalent protein—gene conjugates for the in vitro selection of peptides and proteins," ChemBioChem., 2001, 2(9):666-72.

Kwok, "High-throughput genotyping assay approaches," Pharmocogenomics, Feb. 2000, 1(1):95-100.

Lacar et al., "Nuclear RNA-seq of single neurons reveals molecular signatures of activation," Nat Commun., Apr. 2016, 7:11022, 12 pages.

Lage et al., "Whole genome analysis of genetic alterations in small DNA samples using hyperbranched strand displacement amplification and array-CGH," Genome Research, 2003, 13(2):294-307.

Lahiani et al., "Enabling Histopathological Annotations on Immunofluorescent Images through Virtualization of Hematoxylin and Eosin," J Pathol Inform., Feb. 2018, 9:1, 8 pages.

Lake et al., "Neuronal subtypes and diversity revealed by single-nucleus RNA sequencing of the human brain," Science, Jun. 2016, 352(6293):1586-90.

Lampe et al., "A purified mariner transposase is sufficient to mediate transposition in vitro," EMBO J., Oct. 1996, 15(19):5470-9.

Landegren et al., "Reading bits of genetic information: methods for single-nucleotide polymorphism analysis, " Genome Res., Aug. 1998, 8(8):769-76.

Langdale et al., "A rapid method of gene detection using DNA bound to Sephacryl," Gene, 1985, 36(3):201-210.

Larman et al., "Sensitive, multiplex and direct quantification of RNA sequences using a modified RASL assay," Nucleic Acids Research, 2014, 42(14):9146-9157.

Laurell et al., "Chip integrated strategies for acoustic separation and manipulation of cells and particles," Chem. Soc. Rev., Mar. 2007, 36(3):492-506.

Lee et al., "Fluorescent in situ sequencing (FISSEQ) of RNA for gene expression profiling in intact cells and tissues," Nature Protocols, 2015, 10(3):442-458.

Lee et al., "Improving the efficiency of genomic loci capture using oligonucleotide arrays for high throughput resequencing," BMC Genomics, Dec. 2009, 10:646, 12 pages.

Lee et al., "XYZeq: Spatially resolved single-cell RNA sequencing reveals expression heterogeneity in the tumor microenvironment," Science Advances, 2021, 7:eabg4755, 1-14.

Lenard, "Viral Membranes," Encyclopedia of Virology, Jul. 2008, pp. 308-314.

Leriche et al., "Cleavable linkers in chemical biology," Bioorganic & Medicinal Chemistry, 2012, 20:571-582.

Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.

Li et al., "A photocleavable fluorescent nucleotide for DNA sequencing and analysis," Proc. Natl. Acad. Sci., 2003, 100(2):414-419.

Li et al., "An activity-dependent proximity ligation platform for spatially resolved quantification of active enzymes in single cells," Nat Commun, Nov. 2017, 8(1):1775, 12 pages.

Li et al., "RASL-seq for Massively Parallel and Quantitative Analysis of Gene Expression," Curr Protoc Mol Biol., Apr. 2012, 4(13):1-10.

Li et al., "Review: a comprehensive summary of a decade development of the recombinase polymerase amplification," Analyst, Dec. 2018, 144(1):31-67.

(56) References Cited

OTHER PUBLICATIONS

Liberali et al., "Single-cell and multivariate approaches in genetic perturbation screens," Nat Rev Genet., Jan. 2015, 16(1):18-32.
Lin et al., "Highly multiplexed imaging of single cells using a high-throughput cyclic immunofluorescence method," Nat Commun., Sep. 2015, 6:8390, 7 pages.
Lin et al., "Microfluidic cell trap array for controlled positioning of single cells on adhesive micropatterns," Lab Chip, Feb. 2013, 13(4):714-721.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omnics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lubeck et al., "Single cell systems biology by super-resolution imaging and combinatorial labeling," Nature Methods, Jan. 2013, 9(7):743-748, 18 pages.
Lubeck et al., "Single-cell in situ RNA profiling by sequential hybridization," Nature Methods, Apr. 2014, 11(4):360-361, 2 pages (Supplemental Materials).
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.

Macosko et al., "Highly Parallel Genome-wide Expression Profiling of Individual Cells Using Nanoliter Droplets," Cell, 2015, 161:1202-1214.
Madissoon et al., "scRNA-seq assessment of the human lung, spleen, and esophagus tissue stability after cold preservation," Genome Biol., Dec. 2019, 21(1):1, 16 pages.
Maginnis, "Virus-Receptor Interactions: The Key to Cellular Invasion," J Mol. Bio., Aug. 2018, 430(17):2590-2611.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
McGinnis et al., "MULTI-seq: sample multiplexing for single-cell RNA sequencing using lipid-tagged indices," Nat Methods, Jul. 2019, 16(7): 619-626, 14 pages.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Morlan et al., "Selective depletion of rRNA enables whole transcriptome profiling of archival fixed tissue," PLoS One, Aug. 2012, 7(8):e42882, 8 pages.
Mortazavi et al., "Mapping and quantifying mammalian transcriptomes by RNA-Seq," Nature Methods, 5(7): 621-8, 2008.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nakamura et al., "Biocompatible inkjet printing technique for designed seeding of individual living cells," Tissue Eng, Nov. 2005, 11(11-12):1658-1666.

(56) References Cited

OTHER PUBLICATIONS

Nallur et al., "Signal amplification by rolling circle amplification on DNA microarrays," Nucleic Acids Res., Dec. 1, 2001, 29(23):e118, 9 pages.

Nam et al., "Somatic mutations and cell identity linked by Genotyping of Transcriptomes," Nature, Jul. 2019, 571(7765):355-360.

Nandakumar et al., "How an RNA Ligase Discriminates RNA versus DNA Damage," Molecular Cell, 2004, 16:211-221.

Nandakumar et al., "RNA Substrate Specificity and Structure-guided Mutational Analysis of Bacteriophage T4 RNA Ligase 2," Journal of Biological Chemistry, Jul. 2004, 279(30):31337-31347.

Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Nelson et al., "Ebola Virus Does Not Induce Stress Granule Formation during Infection and Sequesters Stress Granule Proteins within Viral Inclusions," J Virol., Jul. 2016, 90(16):7268-7284.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Niedringhaus et al., "Landscape of next-generation sequencing technologies," Anal Chem., Jun. 2011, 83(12):4327-41.

Nikiforov et al., "The use of 96-well polystyrene plates for DNA hybridization-based assays: an evaluation of different approaches to oligonucleotide immobilization," Anal Biochem, May 1995, 227(1):201-9.

Niklas et al., "Selective permeabilization for the high-throughput measurement of compartmented enzyme activities in mammalian cells," Anal Biochem, Sep. 2011, 416(2):218-27.

Nilsson et al., "RNA-templated DNA ligation for transcript analysis," Nucleic Acids Res., Jan. 2001, 29(2):578-81.

Nowak et al., "Entering the Postgenome Era," Science, 1995, 270(5235):368-71.

Ohtsubo et al., "Bacterial insertion sequences," Curr Top Microbiol Immunol., 1996, 204:1-26.

Olivier, "The Invader assay for SNP genotyping," Mutat. Res., Jun. 2005, 573(1-2):103-110.

Ostuni et al., "Patterning Mammalian Cells Using Elastomeric Membranes," Langmuir, Aug. 2000, 16(20):7811-7819.

Ozsolak et al., "Digital transcriptome profiling from attomole-level RNA samples," Genome Res., Apr. 2010, 20(4):519-25.

Pandey et al., "Inhibition of terminal deoxynucleotidyl transferase by adenine dinucleotides. Unique inhibitory action of Ap5A," FEBS Lett., Mar. 1987, 213(1):204-8.

Park et al., "Single cell trapping in larger microwells capable of supporting cell spreading and proliferation," Microfluid Nanofluid, 2010, 8:263-268.

Passow et al., "RNAlater and flash freezing storage methods nonrandomly influence observed gene expression in RNAseq experiments," bioRxiv, Jul. 2018, 28 pages.

Pellestor et al., "The peptide nucleic acids (PNAs), powerful tools for molecular genetics and cytogenetics," Eur J Hum Genet., Sep. 2004, 12(9):694-700.

Pemov et al., "DNA analysis with multiplex microarray-enhanced PCR," Nucl. Acids Res., Jan. 2005, 33(2):e11, 9 pages.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perler et al., "Intervening sequences in an Archaea DNA polymerase gen," Proc Natl Acad Sci USA, Jun. 1992, 89(12):5577-5581.

Perocchi et al., "Antisense artifacts in transcriptome microarray experiments are resolved by actinomycin D," Nucleic Acids Res., 2007, 35(19):e128, 7 pages.

Petterson et al., "Generations of sequencing technologies," Genomics, 2009, 93(2):105-111.

Picelli et al., "Full-length RNA-seq from single cells using Smart-seq2," Nat Protoc., Jan. 2014, 9(1):171-81.

Picelli et al., "Tn5 transposase and tagmentation procedures for massively scaled sequencing projects," Genome Res., Dec. 2014, 24(12):2033-40.

Pipenburg et al., "DNA detection using recombination proteins," PLoS Biol., Jul. 2006, 4(7):e204, 7 pages.

Pirici et al., "Antibody elution method for multiple immunohistochemistry on primary antibodies raised in the same species and of the same subtypem," J. Histochem. Cytochem., Jun. 2009, 57(6):567-75.

Plasterk, "The Tcl/mariner transposon family," Curr Top Microbiol Immunol., 1996, 204:125-43.

Plongthongkum et al., "Advances in the profiling of DNA modifications: cytosine methylation and beyond," Nature Reviews Genetics, Aug. 2014, 15(10):647-661.

Polsky-Cynkin et al., "Use of DNA immobilized on plastic and agarose supports to detect DNA by sandwich hybridization," Clin. Chem., 1985, 31(9):1438-1443.

Porreca et al., "Polony DNA sequencing," Curr Protoc Mol Biol., Nov. 2006, Chapter 7, Unit 7.8, pp. 7.8.1-7.8.22.

U.S. Appl. No. 61/267,363, filed Dec. 7, 2009, 33 pages.

Qiu et al., "Combination probes with intercalating anchors and proximal fluorophores for DNA and RNA detection," Nucleic Acids Research, Sep. 2016, 44(17):e138, 12 pages.

Raab et al., "Human tRNA genes function as chromatin insulators," EMBO J., Jan. 2012, 31(2):330-50.

Raj et al., "Imaging individual mRNA molecules using multiple singly labeled probes," Nature Methods, Oct. 2008, 5(10):877-879, 9 pages.

Ranki et al., "Sandwich hybridization as a convenient method for the detection of nucleic acids in crude samples," Gene, 1983, 21(1-2):77-85.

Reinartz et al., "Massively parallel signature sequencing (MPSS) as a tool for in-depth quantitative gene expression profiling in all organisms," Brief Funct Genomic Proteomic, Feb. 2002, 1(1):95-104.

Rettig et al., "Large-scale single-cell trapping and imaging using microwell arrays," Anal Chem, Sep. 2005, 77(17):5628-5634.

Reznikoff, "Tn5 as a model for understanding DNA transposition," Mol Microbiol., Mar. 2003, 47(5):1199-206.

Rialdi et al., "The RNA Exosome Syncs IAV-RNAPII Transcription to Promote Viral Ribogenesis and Infectivity," Cell, May 2017, 169(4):679-692.

Ristic et al., "Detection of Protein-Protein Interactions and Post-translational Modifications Using the Proximity Ligation Assay: Application to the Study of the SUMO Pathway," Methods Mol. Biol., 2016, 1449:279-90.

Rodriques et al., "Slide-seq: A scalable technology for measuring genome-wide expression at high spatial resolution," Science, 2019, 363(6434):1463-1467.

Ronaghi et al., "A sequencing method based on real-time pyrophosphate," Science, Jul. 1998, 281(5375):363-365.

Ronaghi et al., "Real-time DNA sequencing using detection of pyrophosphate release," Analytical Biochemistry, Nov. 1996, 242(1):84-89.

Ronaghi, "Pyrosequencing sheds light on DNA sequencing," Genome Res, Jan. 2001, 11(1):3-11.

Rosenthal et al., "Cell patterning chip for controlling the stem cell microenvironment," Biomaterials, Jul. 2007, 28(21):3208-3216.

Roy et al., "Assessing long-distance RNA sequence connectivity via RNA-templated DNA-DNA ligation," eLife, 2015, 4:e03700, 21 pages.

Russell et al., "Molecular mechanisms of late endosome morphology, identity and sorting," Curr. Opin. Cell Bio., Aug. 2006, 18(4):422-428.

Salmén et al., "Barcoded solid-phase RNA capture for Spatial Transcriptomics profiling in mammalian tissue sections," Nature Protocols, Oct. 2018, 13(11):2501-2534.

(56) References Cited

OTHER PUBLICATIONS

Satpathy et al., "Massively parallel single-cell chromatin landscapes of human immune cell development and intratumoral T cell exhaustion," Nat Biotechnol., Aug. 2019, 37(8):925-936.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Setliff et al., High-Throughput Mapping of B Cell Receptor Sequences to Antigen Specificity, Cell, 2019, 179:1636-1646.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Shirai et al., "Novel Tools for Analyzing Gene Expressions in Single Cells," The 5th International Workshop on Approaches to Single-Cell Analysis, The University of Tokyo, Mar. 3-4, 2011, 1 page.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "Scrinshot, a spatial method for single-cell resolution mapping of cell states in tissue sections," PLoS Biol., Nov. 2020, 18(11):e3000675, 32 pages.
Sparrer et al., "Intracellular detection of viral nucleic acids," Curr. Opin. Microbiol., Aug. 2015, 26:1-9.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Stoeckius et al., "Cell Hashing with barcoded antibodies enables multiplexing and doublet detection for single cell genomics," Genome Biology, Dec. 19, 2018, 19: 224, 12 pages.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Stuart et al., "Comprehensive Integration of Single-Cell Data," Cell, Jun. 2019, 177(7):1888-1902.
Suh et al., "A simple soft lithographic route to fabrication of poly(ethylene glycol) microstructures for protein and cell patterning," Biomaterials, Feb. 2004, 25(3):557-563.
Sutherland et al., "Utility of formaldehyde cross-linking and mass spectrometry in the study of protein-protein interactions," J. Mass Spectrom., Jun. 2008, 43(6):699-715.
Tan et al., "Parylene peel-off arrays to probe the role of cell-cell interactions in tumour angiogenesis," Integr Biol (Camb), Oct. 2009, 1(10):587-594.
Tang et al., "RNA-Seq analysis to capture the transcriptome landscape of a single cell.," Nat Protoc., 5:516-35, 2010.
Taniguchi et al., "Quantitative analysis of gene expression in a single cell by qPCR," Nature Methods, 6, pp. 503-506, 2009.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS One, Feb. 2019, 14(2):e0212031, 22 pages.
Tseng et al., "Magnetic nanoparticle-mediated massively parallel mechanical modulation of single-cell behavior," Nat Methods, Nov. 2012, 9(11):1113-1119.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.

(56) References Cited

OTHER PUBLICATIONS

Vázquez Bernat et al., "High-Quality Library Preparation for NGS-Based Immunoglobulin Germline Gene Inference and Repertoire Expression Analysis," Front Immunol., Apr. 2019, 10:660, 12 pages.

Velculescu et al., "Serial analysis of gene expression," Science, Oct. 1995, 270(5235):484-7.

Vermesh et al., "High-density, multiplexed patterning of cells at single-cell resolution for tissue engineering and other applications," Angew Chem Int Ed Engl, Aug. 2011, 50(32):7378-7380.

Vickovic et al., "High-definition spatial transcriptomics for in situ tissue profiling," Nat Methods, Oct. 2019, 16(10):987-990.

Vickovic et al., "Massive and parallel expression profiling using microarrayed single-cell sequencing," Nature Communications, 2016, 7(13182):1-9.

Vickovic et al., "SM-Omics: An automated Platform for High-Throughput Spatial Multi-Omics," bioRxiv, Oct. 2020, 40 pages.

Vincent et al., "Helicase-dependent isothermal DNA amplification," EMBO Rep., Aug. 2004, 5(8):795-800.

Viollet et al., "T4 RNA ligase 2 truncated active site mutants: improved tools for RNA analysis," BMC Biotechnol., Jul. 2011, 11:72, 14 pages.

Vogelstein et al., "Digital PCR," Proceedings of the National Academy of Sciences, Aug. 1999, 96(16):9236-9241.

Waichman et al., "Functional immobilization and patterning of proteins by an enzymatic transfer reaction," Analytical chemistry, 2010, 82(4):1478-85.

Walker et al., "Strand displacement amplification—an isothermal, in vitro DNA amplification technique," Nucleic Acids Research, 1992, 20(7):1691-1696.

Wang et al., "Concentration gradient generation methods based on microfluidic systems," RSC Adv., 2017, 7:29966-29984.

Wang et al., "High-fidelity mRNA amplification for gene profiling," Nature Biotechnology, Apr. 2000, 18(4):457-459.

Wang et al., "Imaging-based pooled CRISPR screening reveals regulators of lncRNA localization," Proc Natl Acad Sci USA, May 2019, 116(22):10842-10851.

Wang et al., "Optimization of Process Conditions for Infected Animal Tissues by Alkaline Hydrolysis Technology," Procedia Environmental Sciences, 2016, 31:366-374.

Wang et al., "Single cell analysis: the new frontier in 'omics,'" Trends Biotechnol., 28: 281-90, 2010.

Wang et al., "Tagmentation-based whole-genome bisulfite sequencing," Nature Protocols, Oct. 2013, 8(10):2022-2032.

Wang, "RNA amplification for successful gene profiling analysis," J Transl Med., Jul. 2005, 3:28, 11 pages.

Watanabe et al., "Cellular networks involved in the influenza virus life cycle," Cell Host & Microbe, Jun. 2010, 7(6):427-39.

Weinreich et al., "Evidence that the cis Preference of the Tn5 Transposase is Caused by Nonproductive Multimerization," Genes and Development, Oct. 1994, 8(19):2363-2374.

Wheeler et al., "Microfluidic device for single-cell analysis," Analytical Chemistry, Jul. 2003, 75(14):3581-3586.

Wiedmann et al., "Ligase chain reaction (LCR)—overview and applications," PCR Methods Appl., Feb. 1994, 3(4):S51-64.

Wilson et al., "New transposon delivery plasmids for insertional mutagenesis in Bacillus anthracis," J Microbiol Methods, Dec. 2007, 71(3):332-5.

Wohnhaas et al., "DMSO cryopreservation is the method of choice to preserve cells for droplet-based single-cell RNA sequencing," Scientific Reports, Jul. 2019, 9(1):10699, 14 pages.

Wolf et al., "Rapid hybridization kinetics of DNA attached to submicron latex particles," Nucleic Acids Res, 1987, 15(7):2911-2926.

Wong et al., "Direct Site-Selective Covalent Protein Immobilization Catalyzed by a Phosphopantetheinyl Transferase," J. Am. Chem Soc., 2008, 130(37):12456-64.

Wood et al., "Single cell trapping and DNA damage analysis using microwell arrays," PNAS, Jun. 2010, 107(22):10008-10013.

Worthington et al., "Cloning of random oligonucleotides to create single-insert plasmid libraries," Anal Biochem, 2001, 294(2):169-175.

Wright et al., "Reusable, reversibly sealable parylene membranes for cell and protein patterning," J Biomed Mater Res A., May 2008, 85(2):530-538.

Wu et al., "Detection DNA Point Mutation with Rolling-Circle Amplification Chip," IEEE, 2010 4th International Conference on Bioinformatics and Biomedical Engineering, Jun. 2010, 4 pages.

Wu et al., "RollFISH achieves robust quantification of single-molecule RNA biomarkers in paraffin-embedded tumor tissue samples," Commun Biol., Nov. 2018, 1:209, 8 pages.

Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.

Yamauchi et al., "Subcellular western blotting of single cells," Microsyst Nanoeng., 2017, 3:16079, 9 pages.

Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.

Yeakley et al., "A trichostatin A expression signature identified by TempO-Seq targeted whole transcriptome profiling," PLoS One, May 2017, 12(5):e0178302, 22 pages.

Yeakley et al., "Profiling alternative splicing on fiber-optic arrays," Nature biotechnology, 2002, 20:353-358.

Yershov et al., "DNA analysis and diagnostics on oligonucleotide microchips," Proc. Natl. Acad. Sci. USA, May 1996, 93(10):4913-4918.

Yin et al., "Genetically encoded short peptide tag for versatile protein labeling by Sfp phosphopantetheinyl transferase," PNAS, 2005, 102(44):15815-20.

Yusof et al., "Inkjet-like printing of single-cells," Lab Chip, Jul. 2011, 11(14):2447-2454.

Zhang et al., "Archaeal RNA ligase from Thermoccocus kodakarensis for template dependent ligation," RNA Biol., Jan. 2017, 14(1):36-44.

Zhang et al., "Assembling DNA through Affinity Binding to Achieve Ultrasensitive Protein Detection," Angew Chem Int Ed Engl., 2013, 52(41):10698-705.

Zhang et al., "Binding-induced DNA assembly and its application to yoctomole detection of proteins," Anal Chem, 2012, 84(2):877-884.

Zhang et al., "Block-Cell-Printing for live single-cell printing," PNAS, Feb. 2014, 111(8):2948-2953.

Zhang et al., "Genome-wide open chromatin regions and their effects on the regulation of silk protein genes in Bombyx mori," Sci Rep., Oct. 2017, 7(1):12919, 9 pages.

Zhang et al., "Multiplex ligation-dependent probe amplification (MLPA) for ultrasensitive multiplexed microRNA detection using ribonucleotide-modified DNA probes," Chem. Commun., 2013, 49:10013-10015.

Zhao et al., "Isothermal Amplification of Nucleic Acids," Chemical Reviews, Nov. 2015, 115(22):12491-12545.

Zheng et al., "Massively parallel digital transcriptional profiling of single cells," Nat Commun., Jan. 16, 2017, 8:14049, 12 pages.

Zheng et al., "Origins of human mitochondrial point mutations as DNA polymerase gamma-mediated errors," Mutat. Res., 2006, 599(1-2):11-20.

Zhou et al., "Genetically encoded short peptide tags for orthogonal protein labeling by Sfp and AcpS phosphopantetheinyl transferases," ACS Chemical Biol., 2007, 2(5):337-346.

Zhu et al., "Reverse transcriptase template switching: a Smart approach for full-length cDNA library construction," Biotechniques, Apr. 2001, 30(4):892-897.

Adam et al., "Psychrophilic proteases dramatically reduce single-cell RNA-seq artifacts: a molecular atlas of kidney development," Development, Oct. 1, 2017, 144(19):3625-3632.

Bibikova et al., "Quantitative gene expression profiling in formalin-fixed paraffin-embedded tissues using universal bead arrays," The American Journal of Pathology, Nov. 1, 2004, 165(5):1799-1807.

(56) References Cited

OTHER PUBLICATIONS

Choi et al., "Multiplexed detection of mRNA using porosity-tuned hydrogel microparticles," Analytical Chemistry, Sep. 28, 2012, 84(21):9370-9378.
Eastburn et al., "Identification of Genetic Analysis of Cancer Cells with PCT-activated Cell Sorting," Nucleic Acids Research, Jul. 16, 2014, 42(16):e128, 10 pages.
Eastburn et al., "Ultrahigh-throughput Mammalian Single Cell Reverse-transcriptase Polymerase Chain Reaction in Microfluiding Drops," Analytical Chemistry, American Chemical Society, Aug. 20, 2013, 85(16):8016-8021.
Edsgard et al., "Identification of spatial expression trends in single-cell gene expression data," Nature Methods, Mar. 19, 2018, 15: 339-342, 16 pages.
Fan et al., "A versatile assay for high-throughput gene expression profiling on universal array matrices," Genome Research, May 1, 2004, 14(5):878-885.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Ha et al, "Self-assembly hollow nanosphere for enzyme encapsulation," Soft Matter, Feb. 11, 2010, 6, 1405-1408, 10 pages.
Hu et al., "A thermo-degradable hydrogel with light-tunable degradation and drug release," Biomaterials, Jan. 2017, 112:133-140.
Ju et al, "Supramolecular dendrimer capsules by cooperative binding," Chem. Commun., Jan. 7, 2011, 47(1):268-270, 8 pages.
Kuiper et al, "Enzymes containing porous polymersomes as nano reaction vessels for cascade reactions," Org. Biomol, Chem, Oct. 15, 2008, 6(23):4315-4318.
Liu et al., "Preparation and Characterization of Temperature-Sensitive Poly(N-isopropylacrylamide)-b-poly(d,1-lactide) Microspheres for Protein Delivery," Biomacromolecules, 2003, 4(6):1784-1793.
Luo et al., "Probing infectious disease by single-cell RNA sequencing: Progresses and perspectives," Computational and Structural Biotechnology Journal, Oct. 21, 2020, 18:2962-2971.
Lyu et al., "One-Pot Synthesis of Protein-Embedded Metal-Organic Frameworks with Enhanced Biological Activities," Nano Lett., Sep. 11, 2014, 14:5761-5765.
Massoni-Badosa et al, "Sampling artifacts in single-cell genomics cohort studies," bioRxiv, Jan. 15, 2020, 32 pages.
Miller et al., "Rapid and Efficient Enzyme Encapsulation in a Dendrimer Silica Nanocomposite," Macromolecular Bioscience, Oct. 25, 2006, 6(10):839-845.
O'Flanagan et al, "Dissociation of solid tumor tissues with cold active protease for single-cell RNA-seq minimizes conserved collagenase-associated stress responses," Genome Biology, Oct. 17, 2019, 20:210, 13 pages.
Pellegrino et al, "High-throughput Single-cell DNA Sequencing of Acut Myeloid Leukemia Tumors with Droplet Microfluidics," Genome Research, Aug. 7, 2018, 28(9):1345-1352.
Rahimi et al, "Synthesis and Characterization of Thermo-Sensitive Nanoparticles for Drug Delivery Applications," J. Biomed. Nanotechnol. Dec. 2008, 4(4):482-490, 19 pages.
Shieh, et al., "Imparting Functionality to Biocatalysts via Embedding Enzymes into Nanoporous Materials by a de Novo Approach: Size-Selective Sheltering of Catalase in Metal-Organic Framework Microcrystals," J Am Chem Soc., Apr. 8, 2015, 137(13):4276-4279, 4 pages.
Soderberg, "Droplet Microfluidics Reverse Transcription and PCR Towards Single Cell and Exosome Analysis," Doctoral Thesis, KTH School of Biotechnology Science for Life Laboratory, 2017, 69 pages.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.

Takei et al., "Integrated Spatial Genomics Reveals Global Architecture of Single Nuclei," Nature, Jan. 27, 2021, 590(7845):344-350, 53 pages.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Hobro et al., "An evaluation of fixation methods: Spatial and compositional cellular changes observed by Raman imaging," Vibrational Spectroscopy, Jul. 2017, 91:31-45.
Landegren et al., "A Ligase-Mediated Gene Detection Technique," Science, 1988, 241(4869):1077-1080.
Mamedov et al., "Preparing unbiased T-cell receptor and antibody cDNA libraries for the deep next generation sequencing profiling," Frontiers in Immunol., Dec. 23, 2013, 4(456):1-10.
Oksuz et al., "Systematic evaluation of chromosome conformation capture assays," Nature Methods, Sep. 2021, 18:1046-1055.
Rohland et al., "Partial uracil-DNA-glycosylase treatment for screening of ancient DNA," Phil. Trans. R. Soc. B, Jan. 19, 2015, 370(1660): 20130624, 11 pages.
Schmidl et al., "ChIPmentation: fast, robust, low-input ChIP-seq for histones and transcription factors," Nature Methods, Oct. 2015, 12:963-965.
Su et al., "Restriction enzyme selection dictates detection range sensitivity in chromatin conformation capture-based variant-to-gene mapping approaches," bioRxiv, Dec. 15, 2020, 22 pages.
Chen et al. "Arrayed profiling of multiple glycans on whole living cell surfaces." Analytical chemistry, Oct. 15, 2013, 85(22):11153-11158.
Howell et al., "iFRET: An Improved Fluorescence System for DNA-Melting Analysis," Genome Research, 2002, 12:1401-1407.
Lu et al., "Highly multiplexed profiling of single-cell effector functions reveals deep functional heterogeneity in response to pathogenic ligands," PNAS, Feb. 2, 2015, E607-E615.
Lu et al., "Highly multiplexed profiling of single-cell effector functions reveals deep functional heterogeneity in response to pathogenic ligands," PNAS, Feb. 2, 2015, E607-E615 (Supplementary Information), 94 pages.
Nam et al., "Nanoparticle-Based Bio-Bar Codes for the Ultrasensitive Detection of Proteins," Science, Sep. 26, 2003, 301(5641):1884-1886.
Pittcon, "Single Molecule Detection of Proteins in Single Cells," News-Medical, Feb. 3, 2017, retreived on Nov. 1, 2023, retrieved from URL <https://www.news-medical.net/news/20170203/Single-molecule-detection-of-proteins-in-single-cells.aspx>, 13 pages.
Redmond et al., "Single-cell TCRseq: paired recovery of entire T-cell alpha and beta chain transcripts in T-cell receptors from single-cell RNAseq," Genome Med, 2016, 8:80, 12 pages.
Tang et al., "mRNA-Seq whole-transcriptome analysis of a single cell," Nat Methods, 2009, 6:377-382.
Asp et al., "A spatiotemporal organ-wide gene expression and cell atlas of the developing human heart," Cell, Dec. 12, 2019, 179(7):1647-1660.
Fiskin et al., "Single-cell multimodal profiling of proteins and chromatin accessibility using Phage-Atac," bioRxiv, posted Oct. 20, 2020, 63 pages.
10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

(56) References Cited

OTHER PUBLICATIONS

Gerard et al., "High-throughput single-cell activity-based screening and sequencing of antibodies using droplet microfluidics," Nature Biotechnology, Jun. 2020, 38(6):715-721, 19 pages.

Hatori et al., "Particle-Templated Emulsification for Microfluidics-Free Digital Biology," Anal. Chem., 2018, 90:9813-9820.

Kuhn et al., "A novel, high-performance random array platform for quantitative gene expression profiling," Genome Res, 2004, 14:2347-2356.

Wang et al., "Multiplexed PCR-Free Detection of MicroRNAs in Single Cancer Cells Using a DNA-Barcoded Microtrough Array Chip," Micromachines, 2019, 10(4):215, 11 pages.

* cited by examiner

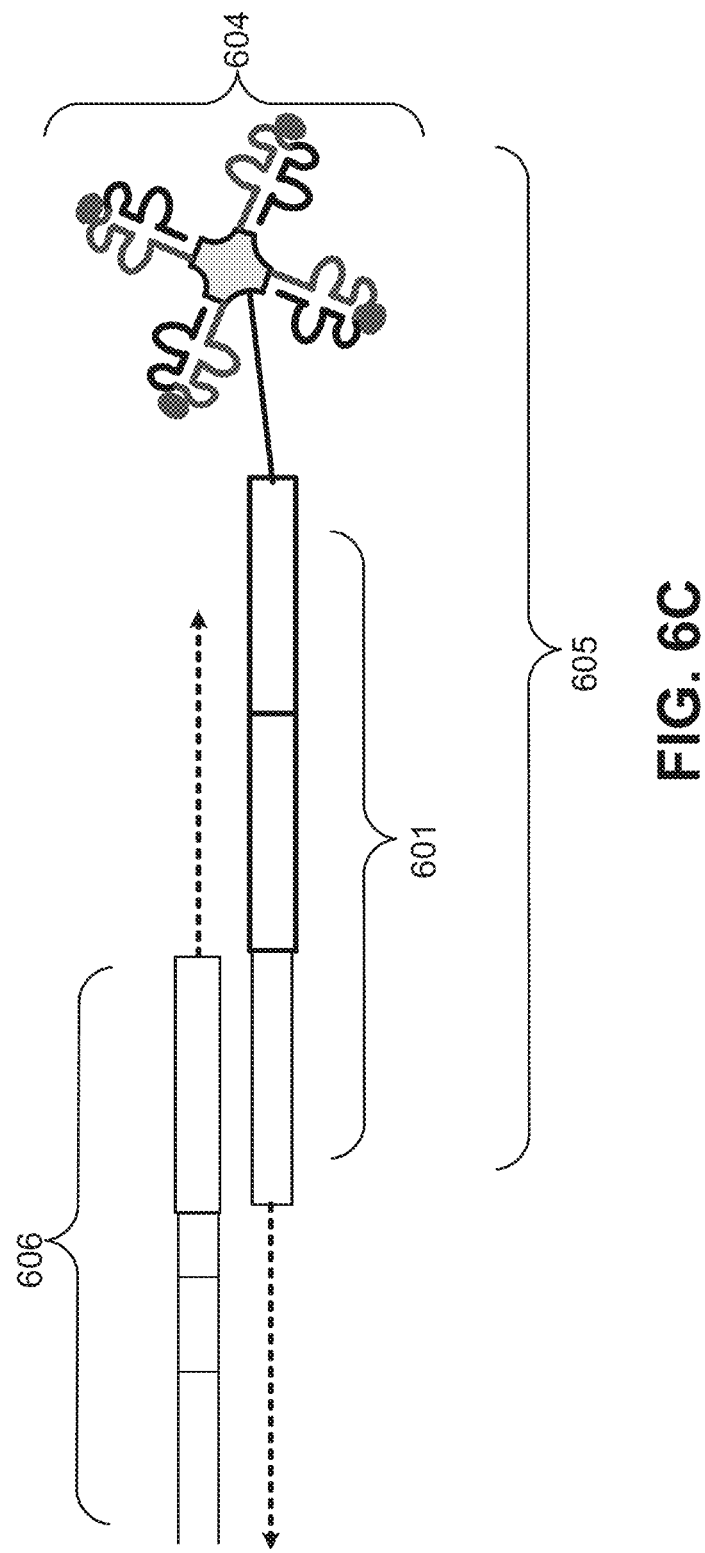

METHODS FOR SPATIAL ANALYSIS USING PROXIMITY LIGATION

CROSS-REFERENCE TO RELATED APPLICATIONS

This application is a continuation of U.S. patent application Ser. No. 17/155,764, filed on Jan. 22, 2021, which claims priority to U.S. Provisional Patent Application No. 62/965,612, filed Jan. 24, 2020; and U.S. Provisional Patent Application No. 63/043,459, filed Jun. 24, 2020. The contents of each of these applications are incorporated herein by reference in their entireties.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Proximity ligation is used to identify two analytes that have a spatial relationship to one another (e.g., two sequences on the same transcript; protein-protein interaction). There remains a need to develop strategies to enhance proximity ligation.

SUMMARY

In one aspect, this disclosure features methods of determining a location or abundance of an interaction between a first analyte and a second analyte in a biological sample, the method including: (a) contacting the biological sample with a substrate including a plurality of capture probes, where a capture probe of the plurality of capture probes includes a spatial barcode and a capture domain; (b) attaching a first analyte-binding moiety to the first analyte, where the first analyte-binding moiety is bound to a first oligonucleotide including a first barcode that is unique to the interaction between the first analyte and the first analyte-binding moiety; (c) attaching a second analyte-binding moiety to the second analyte, where the second analyte-binding moiety is bound to a second oligonucleotide including a second barcode that is unique to the interaction between the second analyte and the second analyte-binding moiety; (d) hybridizing a third oligonucleotide to the first oligonucleotide and to the second oligonucleotide; (e) ligating the first oligonucleotide and the second oligonucleotide, thereby generating a ligation product including a capture probe capture domain sequence; and (f) hybridizing the capture probe capture domain sequence to the capture domain; and (g) determining (i) all or a portion of the sequence of the spatial barcode or a complement thereof; (ii) all or a portion of the sequence of the first barcode or a complement thereof; (iii) all or a portion of the sequence of the second barcode or a complement thereof; and using the determined sequences of (i), (ii), and (iii) to identify the location or abundance of the interaction between the first analyte and the second analyte in the biological sample.

In some embodiments, the first oligonucleotide further includes a first functional sequence, the capture probe capture domain sequence, or both.

In some embodiments, the second oligonucleotide further includes a second functional sequence, the capture probe capture domain sequence, or both.

In some embodiments, the third oligonucleotide includes a sequence that is substantially complementary to the first oligonucleotide. In some embodiments, the third oligonucleotide includes a sequence that is substantially complementary to the second oligonucleotide. In some embodiments, the third oligonucleotide includes a functional sequence, the capture probe capture domain sequence, or both.

In some embodiments, the third oligonucleotide further includes a sequence complementary to the first barcode and a sequence complementary to the second barcode.

In some embodiments, the third oligonucleotide includes at least two oligonucleotides that are serially connected to one another.

In some embodiments, the first oligonucleotide further includes a first bridge sequence and the second oligonucleotide further includes a second bridge sequence.

In some embodiments, the method also includes washing the biological sample after step (d) to remove any third oligonucleotides that are unbound to the first oligonucleotide and/or the second oligonucleotide.

In some embodiments, the method also includes dissociating the third oligonucleotide from the first oligonucleotide and the second oligonucleotide between steps (e) and (f).

In another aspect, this disclosure features a method of determining a location or abundance of an interaction between a first analyte and a second analyte in a biological sample, the method including: (a) contacting the biological sample with a substrate including a plurality of capture probes, where a capture probe of the plurality of capture probes includes a spatial barcode and a capture domain; (b) attaching a first analyte-binding moiety to the first analyte, where the first analyte-binding moiety is bound to a first oligonucleotide including a first barcode that is unique to the interaction between the first analyte and the first analyte-binding moiety and a first bridge sequence; (c) attaching a second analyte-binding moiety to the second analyte, where the second analyte-binding moiety is bound to a second oligonucleotide including a second barcode that is unique to the interaction between the second analyte and the second analyte-binding moiety and a second bridge sequence; (d) hybridizing the first bridge sequence to the second bridge sequence, thereby creating a hybridized proximity oligonucleotide including a capture probe capture domain sequence; (e) hybridizing the capture probe capture domain sequence to the capture domain; (f) determining (i) all or a portion of the sequence of the first barcode or a complement thereof; (ii) all or a portion of the sequence of the second barcode or a complement thereof, and (iii) all or a part of the sequence of the spatial barcode or a complement thereof, and using the determined sequence of (i), (ii), and (iii) to identify the location or abundance of the interaction between the first analyte and the second analyte in the biological sample.

In some embodiments, the first oligonucleotide further includes a first functional sequence, a unique molecular identifier (UMI), the capture probe capture domain sequence, or any combination thereof. In some embodiments, the second oligonucleotide further includes a second functional sequence, a UMI, the capture probe capture domain sequence or a complement thereof, or any combination thereof.

In some embodiments, the first oligonucleotide includes a sequence including one or more uracil nucleotides. In some embodiments, the second oligonucleotide includes a sequence including one or more uracil nucleotides.

In some embodiments, the first oligonucleotide includes from 5' to 3': a functional sequence, a first barcode sequence, and a first bridge sequence. In some embodiments, the first oligonucleotide includes from 5' to 3': a functional sequence, one or more uracil nucleotides, a first barcode sequence, and a first bridge sequence. In some embodiments, the functional sequence includes a second capture probe capture domain sequence, or a complement thereof.

In some embodiments, the second oligonucleotide includes from 5' to 3': a capture probe capture domain sequence, a second barcode sequence, and a second bridge sequence. In some embodiments, the second oligonucleotide includes from 5' to 3': a capture probe capture domain sequence, or a complement thereof, one or more uracil nucleotides, a second barcode sequence, and a second bridge sequence.

In some embodiments, the first bridge sequence is substantially complementary to at least a portion of the second bridge sequence. In some embodiments, the second bridge sequence is substantially complementary to at least a portion of the first bridge sequence.

In some embodiments, the method also includes extending the first oligonucleotide using the second oligonucleotide as a template. In some embodiments, the method also includes extending the second oligonucleotide using the first oligonucleotide as a template. In some embodiments, the extending step includes a U(−) polymerase. In some embodiments, the extending step includes a U(+) polymerase.

In some embodiments, the first analyte-binding moiety is a first protein. In some embodiments, the first protein is a first antibody. In some embodiments, the first antibody is a monoclonal antibody, recombinant antibody, synthetic antibody, a single domain antibody, a single-chain variable fragment (scFv), and or an antigen-binding fragment (Fab).

In some embodiments, the first analyte-binding moiety is a nucleic acid aptamer.

In some embodiments, the first analyte-binding moiety is associated with the first oligonucleotide via a first linker. In some embodiments, the first linker is a cleavable linker, where the first cleavable linker is a photocleavable linker, UV-cleavable linker, or an enzyme-cleavable linker. In some embodiments, the first cleavable linker is an enzyme cleavable linker.

In some embodiments, the first oligonucleotide includes a free 3' end. In some embodiments, the first oligonucleotide includes from 5' to 3': a first barcode and a first bridge sequence. In some embodiments, the first oligonucleotide includes a functional sequence, where the functional sequence is a primer sequence. In some embodiments, the first oligonucleotide includes from 5' to 3': a primer sequence, a first barcode, and a first bridge sequence. In some embodiments, the first oligonucleotide includes from 5' to 3': a functional sequence and a first barcode.

In some embodiments, the second analyte-binding moiety is a second protein. In some embodiments, the second protein is a second antibody. In some embodiments, the second antibody is a monoclonal antibody, recombinant antibody, synthetic antibody, a single domain antibody, a single-chain variable fragment (scFv), and or an antigen-binding fragment (Fab).

In some embodiments, the second analyte-binding moiety is a nucleic acid aptamer.

In some embodiments, the second analyte-binding moiety is associated with the second oligonucleotide via a second linker. In some embodiments, the second linker is a second cleavable linker, where the second cleavable linker is a photocleavable linker, UV-cleavable linker, or an enzyme-cleavable linker. In some embodiments, the second cleavable linker is an enzyme cleavable linker.

In some embodiments, the second oligonucleotide includes a free 5' end. In some embodiments, the second oligonucleotide includes a phosphorylated nucleotide at the 5' end. In some embodiments, the second oligonucleotide includes from 3' to 5': a capture probe capture domain sequence, and a second barcode.

In some embodiments, the second oligonucleotide includes a free 3' end. In some embodiments, the second oligonucleotide includes from 5' to 3': a capture probe capture domain sequence and a second barcode.

In some embodiments, the first barcode and the second barcode are different.

In some embodiments, the first bridge sequence is about 10 nucleotides to about 30 oligonucleotides. In some embodiments, the second bridge sequence is about 10 nucleotides to about 30 nucleotides.

In some embodiments, the third oligonucleotide includes a sequence of about 20 nucleotides to about 60 nucleotides.

In some embodiments, the first analyte and the second analyte are the same. In some embodiments, the first analyte and the second analyte interact with each other in the biological sample. In some embodiments, the first analyte and the second analyte interact with each other via a protein-protein interaction. In some embodiments, the first analyte and the second analyte interact with each other via a cell-cell interaction protein complex.

In some embodiments, the first analyte is selected from the group consisting of: lipids, carbohydrates, peptides, post-translational modifications, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, extracellular and intracellular proteins, antibodies, and antigen binding fragments.

In some embodiments, the second analyte is selected from the group consisting of: lipids, carbohydrates, peptides, post-translational modifications, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, extracellular and intracellular proteins, antibodies, and antigen binding fragments.

In some embodiments, the ligating step uses enzymatic ligation or chemical ligation to create a ligation product. In some embodiments, the enzymatic ligation utilizes ligase. In some embodiments, the ligase is a splintR ligase.

In some embodiments, the method also includes releasing the ligation product. In some embodiments, the releasing includes removing the first oligonucleotide from the first analyte-binding moiety. In some embodiments, the releasing includes removing the second oligonucleotide from the second analyte-binding moiety. In some embodiments, the releasing step includes contacting the first analyte-binding moiety associated with the first oligonucleotide with an enzyme.

In some embodiments, the releasing step includes contacting the second analyte-binding moiety associated with the second oligonucleotide with an enzyme.

In some embodiments, the capture probe capture domain sequence includes a sequence that is substantially complementary to the capture domain.

In some embodiments, the method also includes providing a template switching oligonucleotide, thereby generating a full length oligonucleotide including the first oligonucleotide and the second oligonucleotide.

In some embodiments, the determining step includes amplifying all or part of the ligation product or all or part of the hybridized proximity oligonucleotide bound to the capture domain, thereby generating an amplifying product.

In some embodiments, the amplifying product includes (i) all or part of sequence the ligation product or the hybridized proximity oligonucleotide bound to the capture domain, or a complement thereof, and (ii) all or a part of the sequence of the spatial barcode, or a complement thereof.

In some embodiments, the determining step includes sequencing.

In some embodiments, the first analyte is a host analyte and the second analyte is viral analyte or the first analyte is a viral analyte and the second analyte is a host analyte. In some embodiments, the host analyte is selected from the group consisting of: a host protein, a cell surface moiety, a cell motor protein, a nuclear pore protein, and a RNA polymerase. In some embodiments, the viral analyte selected from the group consisting of: is a viral protein, a viral capsid, a glycoprotein, an envelope protein, a viral coat protein, or an integrase protein. In some embodiments, the viral analyte from virus selected from an Influenza Type A virus, an ebolavirus, human immunodeficiency virus-1, human immunodeficiency virus-2, West Nile virus, avian influenza, severe acute respiratory syndrome coronavirus-1, severe acute respiratory syndrome coronavirus-2, Zika virus, or any combination thereof.

In another aspect, this disclosure features a kit including: (a) an array including a plurality of capture probes; (b) a first analyte-binding moiety and a second analyte-binding moiety, where the first analyte-binding moiety is bound to a first oligonucleotide, where the first oligonucleotide includes: a first barcode, where the second analyte-binding moiety is bound to a second oligonucleotide; where the second oligonucleotide includes: (i) a capture probe capture domain sequence, and (ii) a second barcode; (c) a third oligonucleotide, where the third nucleotide includes a sequence that is substantially complementary to the first oligonucleotide, and a sequence that is substantially complementary to the second oligonucleotide; (d) a plurality of enzymes including a ligase and a polymerase; and (e) instructions for performing any of the methods described herein.

In another aspect, this disclosure features kit including (a) an array including a plurality of capture probes; (b) a first analyte-binding moiety and a second analyte-binding moiety, where the first analyte-binding moiety is bound to a first oligonucleotide, where the first oligonucleotide includes: a first barcode, where the second analyte-binding moiety is bound to a second oligonucleotide; where the second oligonucleotide includes: a second barcode; (c) a third oligonucleotide including (i) a first sequence that is substantially complementary to a portion of the first oligonucleotide, (ii) a second sequence that is substantially complementary to a portion of the second oligonucleotide; and (iii) a capture probe capture domain sequence; (d) a ligase; and (e) instructions for performing any of the methods described herein.

In another aspect, this disclosure features a kit including: (a) an array including a plurality of capture probes; (b) a first analyte-binding moiety and a second analyte-binding moiety, where the first analyte-binding moiety is bound to a first oligonucleotide, where the first oligonucleotide includes: (i) a first barcode; and (ii) a first bridge sequence, where the second analyte-binding moiety is bound to a second oligonucleotide; where the second oligonucleotide includes: (i) a capture probe capture domain sequence; (ii) a second barcode; and (iii) a second bridge sequence, where the first bridge sequence is substantially complementary to the second bridge sequence; (c) a plurality of enzymes including a polymerase and a ligase; and (d) instructions for performing any of the methods described herein.

In some embodiments of any of the kits described herein, the first bridge sequence includes one or more uracil nucleotides.

In some embodiments of any of the kits described herein, the second bridge sequence includes one or more uracil nucleotides.

In another aspect, this disclosure features methods of determining a location of a host analyte-viral analyte interaction in a biological sample comprising: (a) contacting the biological sample with a substrate comprising a plurality of capture probes, wherein a capture probe of the plurality of capture probes comprises a spatial barcode and a capture domain; (b) attaching an analyte-binding moiety to a first analyte in the biological sample, where the analyte-binding moiety is bound to a first oligonucleotide including (i) a first barcode; and (ii) a first bridge sequence; (c) attaching a second oligonucleotide to a viral nucleic acid analyte in the biological sample, where the second oligonucleotide includes: (i) a capture probe capture domain sequence; (ii) a detection sequence that is at substantially complementary to the viral nucleic acid analyte; (iii) a second barcode; and (iv) a second bridge sequence; (d) contacting the biological sample with a third oligonucleotide; (e) hybridizing the third oligonucleotide to the first bridge sequence and to the second bridge sequence; (f) ligating the first oligonucleotide and the second oligonucleotide, thereby generating a ligation product; and (g) hybridizing the capture probe capture domain sequence to the capture domain.

In another aspect, this disclosure features methods of determining a location of a host analyte-viral analyte interaction in a biological sample including: (a) contacting the biological sample with a substrate comprising a plurality of capture probes, wherein a capture probe of the plurality of capture probes comprises a spatial barcode and a capture domain; (b) attaching an analyte-binding moiety to a first analyte in the biological sample, where the analyte-binding moiety is bound to a first oligonucleotide, where the first oligonucleotide includes: (i) a capture probe capture domain sequence (ii) a first barcode; and (ii) a first bridge sequence; (c) attaching a second oligonucleotide to a viral nucleic acid analyte in the biological sample, where the second oligonucleotide includes: (i) a detection sequence that is at substantially complementary to the viral nucleic acid analyte; (ii) a second barcode; and (iii) a second bridge sequence; (d) contacting the biological sample with a third oligonucleotide; (e) hybridizing the third oligonucleotide to the first bridge sequence of the first oligonucleotide and the second bridge sequence of the second oligonucleotide; (f) ligating the first oligonucleotide and the second oligonucleotide, thereby generating a ligation product; and (g) hybridizing the capture probe capture domain sequence to the capture domain.

In some embodiments, the method also includes: (h) determining (i) all or a part of the sequence of the analyte, the analyte molecule, the nucleic acid product derived from the analyte, the nucleic acid product derived from the analyte molecule, the second oligonucleotide, the ligation product, or combination thereof bound to the capture domain, or a complement thereof, and (ii) all or a part of the sequence of the spatial barcode, or a complement thereof, and using the determined sequence of (i) and (ii) to identify the location of the first analyte and the nucleic acid analyte in the biological sample.

In some embodiments, the first analyte-binding moiety is a first protein. In some embodiments, the first protein is a first antibody. In some embodiments, the first antibody is a monoclonal antibody, recombinant antibody, synthetic antibody, a single domain antibody, a single-chain variable fragment (scFv), and or an antigen-binding fragment (Fab). In some embodiments, the first analyte-binding moiety is an aptamer. In some embodiments, the aptamer is a DNA aptamer. In some embodiments, the aptamer is a RNA aptamer. In some embodiments, the first analyte-binding moiety is associated with the first oligonucleotide via a first linker. In some embodiments, the first linker is a cleavable linker. In some embodiments, the first cleavable linker is a photocleavable linker, UV-cleavable linker, or an enzyme-cleavable linker. In some embodiments, the first cleavable linker is an enzyme cleavable linker.

In some embodiments, the first oligonucleotide includes a free 3' end. In some embodiments, the first oligonucleotide includes from 5' to 3': a first barcode and a first bridge sequence. In some embodiments, the first oligonucleotide further includes a functional sequence. In some embodiments, the functional sequence is a primer sequence. In some embodiments, the first oligonucleotide includes from 5' to 3': a primer sequence, a first barcode, and a first bridge sequence. In some embodiments, the first oligonucleotide includes from 5' to 3': a functional sequence and a first barcode.

In some embodiments, the second oligonucleotide includes a sequence of about 20 nucleotides to about 80 nucleotides. In some embodiments, the detection sequence of the second oligonucleotide includes a sequence of about 10 nucleotides to about 40 nucleotides. In some embodiments, the detection sequence includes a sequence that is substantially complementary to a nucleic acid analyte. In some embodiments, the detection sequence includes a sequence that is substantially complementary to a viral nucleic acid analyte.

In some embodiments, the second oligonucleotide includes a cleavable domain. In some embodiments, the cleavage domain is a second cleavable linker. In some embodiments, the second cleavable linker is a photocleavable linker, UV-cleavable linker, or an enzyme-cleavable linker. In some embodiments, the second cleavable linker is an enzyme cleavable linker.

In some embodiments, the second oligonucleotide includes a free 5' end. In some embodiments, the second oligonucleotide includes a phosphorylated nucleotide at the 5' end. In some embodiments, the second oligonucleotide includes from 3' to 5': a capture probe capture domain sequence, a detection sequence, a second barcode, and a second bridge sequence. In some embodiments, second oligonucleotide includes from 3' to 5': a detection sequence, a second barcode, and a second bridge sequence. In some embodiments, the second oligonucleotide includes a free 3' end. In some embodiments, the second oligonucleotide includes a free hydroxyl group at the free 3' end. In some embodiments, the second oligonucleotide includes from 5' to 3': a capture probe capture domain sequence, a detection sequence, a second barcode and a second bridge sequence. In some embodiments, the second oligonucleotide includes from 5' to 3': a detection sequence, a second barcode, and a second bridge sequence. In some embodiments, the first barcode and the second barcode are different. In some embodiments, the first bridge sequence is about 10 nucleotides to about 30 oligonucleotides. In some embodiments, the second bridge sequence is about 10 nucleotides to about 30 nucleotides.

In some embodiments, the first analyte and the nucleic acid analyte interact with each other in the biological sample.

In some embodiments, the first analyte that interacts with the nucleic acid analyte is selected from the group consisting of: lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, extracellular and intracellular proteins, antibodies, and antigen binding fragments.

In some embodiments, the first analyte includes a host protein and the nucleic acid analyte includes a viral nucleic acid sequence. In some embodiments, the first analyte is a host analyte. In some embodiments, the host analyte in a cell surface moiety. In some embodiments, the host analyte is a cell motor. In some embodiments, the host analyte is a nuclear pore. In some embodiments, the host analyte is a RNA polymerase. In some embodiments, the viral nucleic acid sequence includes a viral RNA sequence. In some embodiments, the viral nucleic acid sequence includes a viral DNA sequence.

In some embodiments, further including a wash step. In some embodiments, the wash step occurs between step (b) and step (c).

In some embodiments, the third oligonucleotide includes a sequence that is complementary to the first bridge sequence. In some embodiments, the third oligonucleotide includes a sequence that is partially complementary to the first bridge sequence. In some embodiments, the third oligonucleotide includes a sequence that is complementary to the second bridge sequence. In some embodiments, the third oligonucleotide includes a sequence that is partially complementary to the second bridge sequence. In some embodiments, the third oligonucleotide includes a sequence from 3' to 5': a sequence that is at least partially complementary to the second bridge sequence and a sequence that is at least partially complementary to the first bridge sequence. In some embodiments, the third oligonucleotide includes a sequence from 5' to 3': a sequence that is at least partially complementary to the second bridge sequence a sequence that is at least partially complementary to the first bridge sequence.

In some embodiments, the ligating step uses enzymatic ligation or chemical ligation to create a ligation product. In some embodiments, the enzymatic ligation utilizes ligase. In some embodiments, the ligase is a splintR ligase.

In some embodiments, the method further includes releasing the ligation product. In some embodiments, the releasing includes removing the first oligonucleotide from the first analyte-binding moiety. In some embodiments, the releasing step includes contacting the first analyte-binding moiety associated with the first oligonucleotide with an enzyme.

In some embodiments, the capture probe capture domain sequence includes a sequence that is complementary to the capture domain. In some embodiments, the capture probe capture domain sequence includes a sequence that is partially complementary to the capture domain.

In some embodiments, the method further includes extending the first oligonucleotide.

In some embodiments, the method further includes extending the second oligonucleotide.

In some embodiments, the method further includes providing a template switching oligonucleotide, thereby generating a full length oligonucleotide including the first oligonucleotide and the second oligonucleotide.

In some embodiments, the determining step includes amplifying all or part of the analyte, the analyte molecule, the nucleic acid product derived from the analyte, the nucleic acid product derived from the analyte molecule, the second oligonucleotide, ligation product, or combination thereof bound to the capture domain. In some embodiments, the amplifying is isothermal. In some embodiments, the amplifying is not isothermal. In some embodiments, an amplifying product includes (i) all or part of sequence of the ligation product bound to the capture domain, or a complement thereof, and (ii) all or a part of the sequence of the spatial barcode, or a complement thereof. In some embodiments, the determining step includes sequencing. In some embodiments, the sequencing is in situ sequencing. In some embodiments, in situ sequencing is performed via sequencing-by-synthesis (SBS), sequential fluorescence hybridization, sequencing by ligation, nucleic acid hybridization, or high-throughput digital sequencing techniques.

In some embodiments, the method further includes amplifying the ligation product. In some embodiments, the amplifying includes rolling circle amplification (RCA). In some embodiments, the method further includes detecting the ligation product in situ by adding one or more detection moieties to the biological sample. In some embodiments, the one or more detection moieties includes a nucleic acid that is substantially complementary to the ligation product or a sequence created using RCA. In some embodiments, the one or more detection moieties includes a detection label. In some embodiments, the detection label is selected from a fluorophore, a radioisotope, a chemiluminescent compound, a bioluminescent compound, or a dye.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIGS. 6A-6C are schematics illustrating how streptavidin cell tags can be utilized in an array-based system to produce a spatially-barcoded cells or cellular contents.

a schematic diagram showing a first oligonucleotide extended with a U(−) polymerase using the second oligonucleotide as a template, and a second oligonucleotide extended with a U(−) polymerase using the first oligonucleotide as a template, and (C) a schematic showing a first oligonucleotide extended with a U(+) polymerase using the second oligonucleotide as a template, and the second oligonucleotide extended with a U(+) polymerase using the first oligonucleotide as a template.

Figure 16:
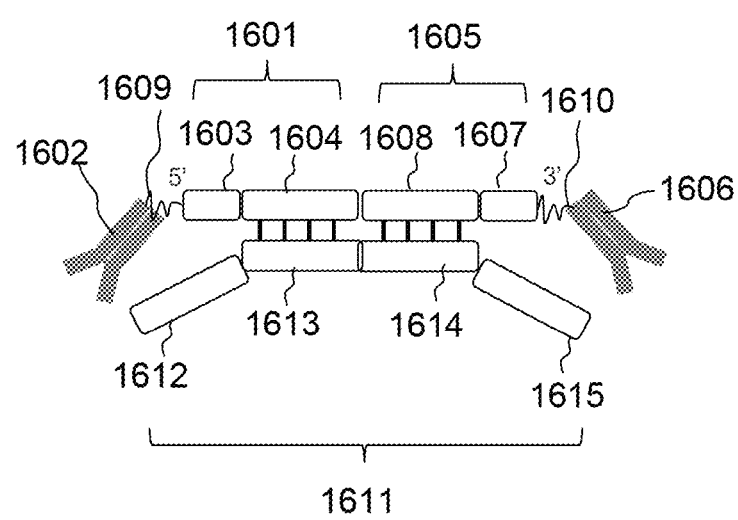

FIG. 16 is a schematic diagram showing a third oligonucleotide hybridized to a first oligonucleotide bound to a first analyte-binding moiety and a second oligonucleotide bound to a second analyte-binding moiety.

Figure 17:
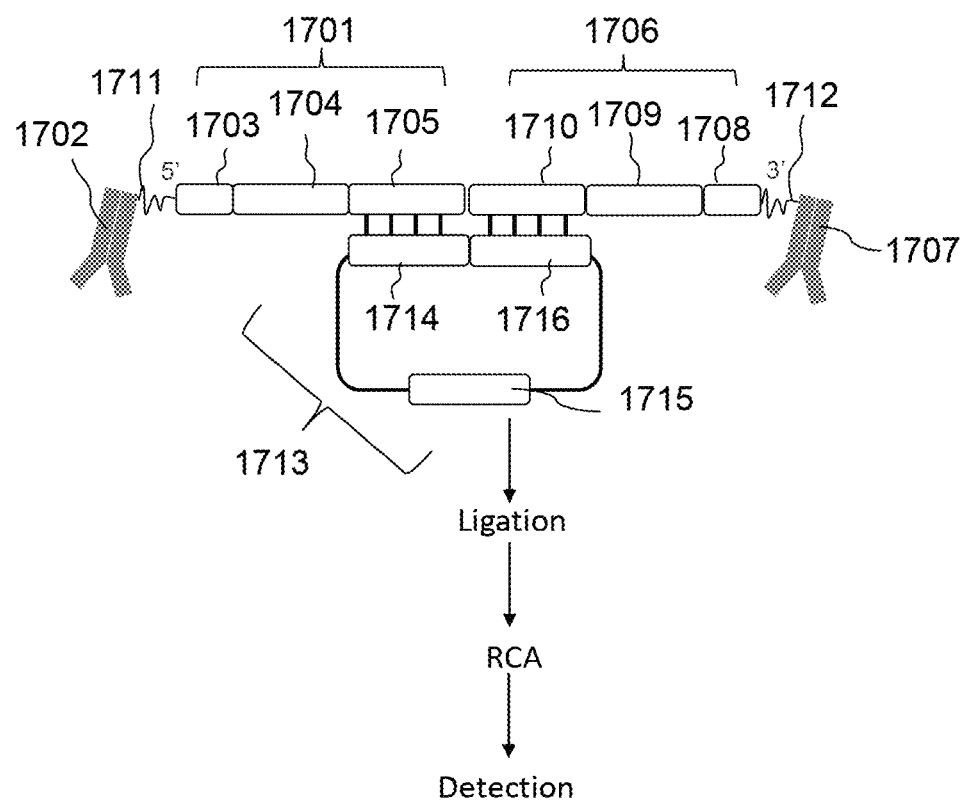

FIG. 17 is a schematic diagram showing a padlock oligonucleotide hybridized to a first oligonucleotide bound to a first analyte-binding moiety and a second oligonucleotide bound to a second analyte-binding moiety.

DETAILED DESCRIPTION

I. Introduction

Spatial analysis methods using capture probes and/or analyte capture agents provide information regarding the abundance and location of an analyte (e.g., a nucleic acid or protein). Traditionally, these methods identify a singular molecule at a location. Extending these methods to study interactions between two or more analytes would provide information on the interactions between two or more analytes at a location in a biological sample. Analyte capture agents as provided herein comprises an analyte binding moiety affixed to an oligonucleotide. The oligonucleotide comprises a sequence that uniquely identifies the analyte and moiety. Further, nearby oligonucleotides affixed to a different moiety in a nearby location can be ligated to the first oligonucleotide and then can be detected using the spatial methods described herein. The methods disclosed herein thus provide the ability to study the interaction between two or more analytes in a biological sample.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a connected probe (e.g., a ligation product) or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)).

Figure 1:
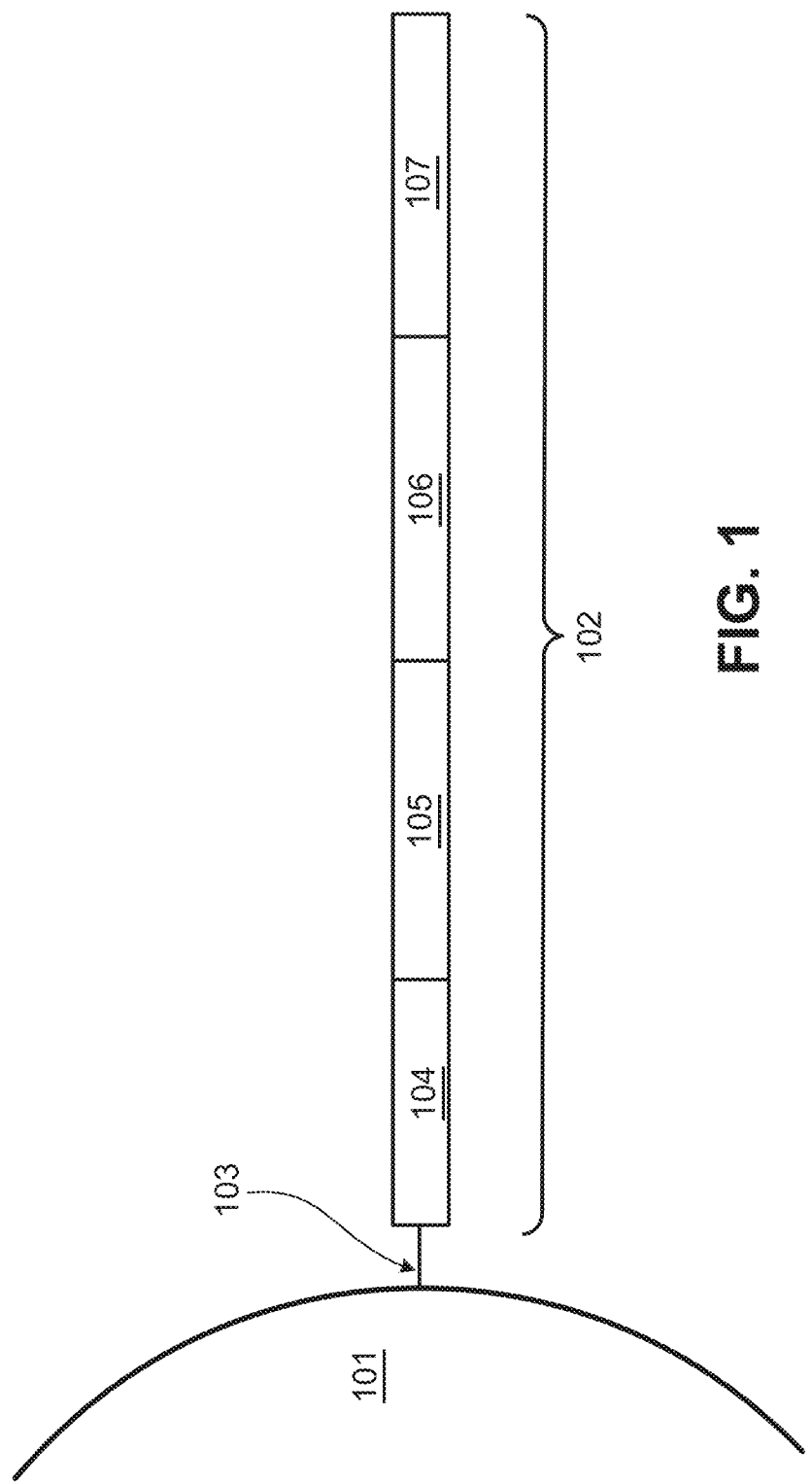
FIG. 1 is a schematic diagram showing an example of a barcoded capture probe, as described herein.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

Figure 2:
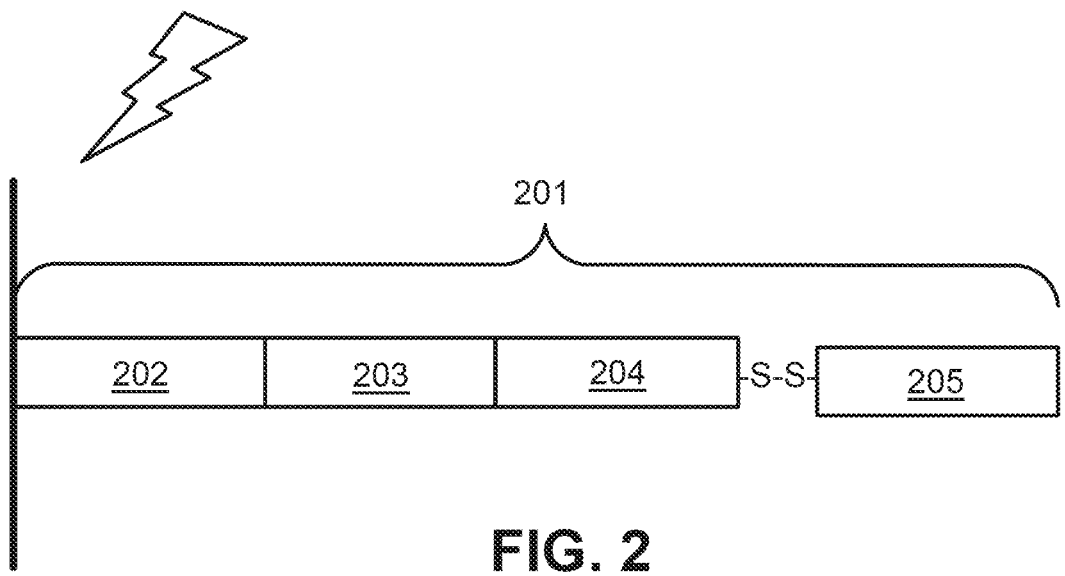
FIG. 2 is a schematic illustrating a cleavable capture probe, wherein the cleaved capture probe can enter into a non-permeabilized cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain.

Figure 3:
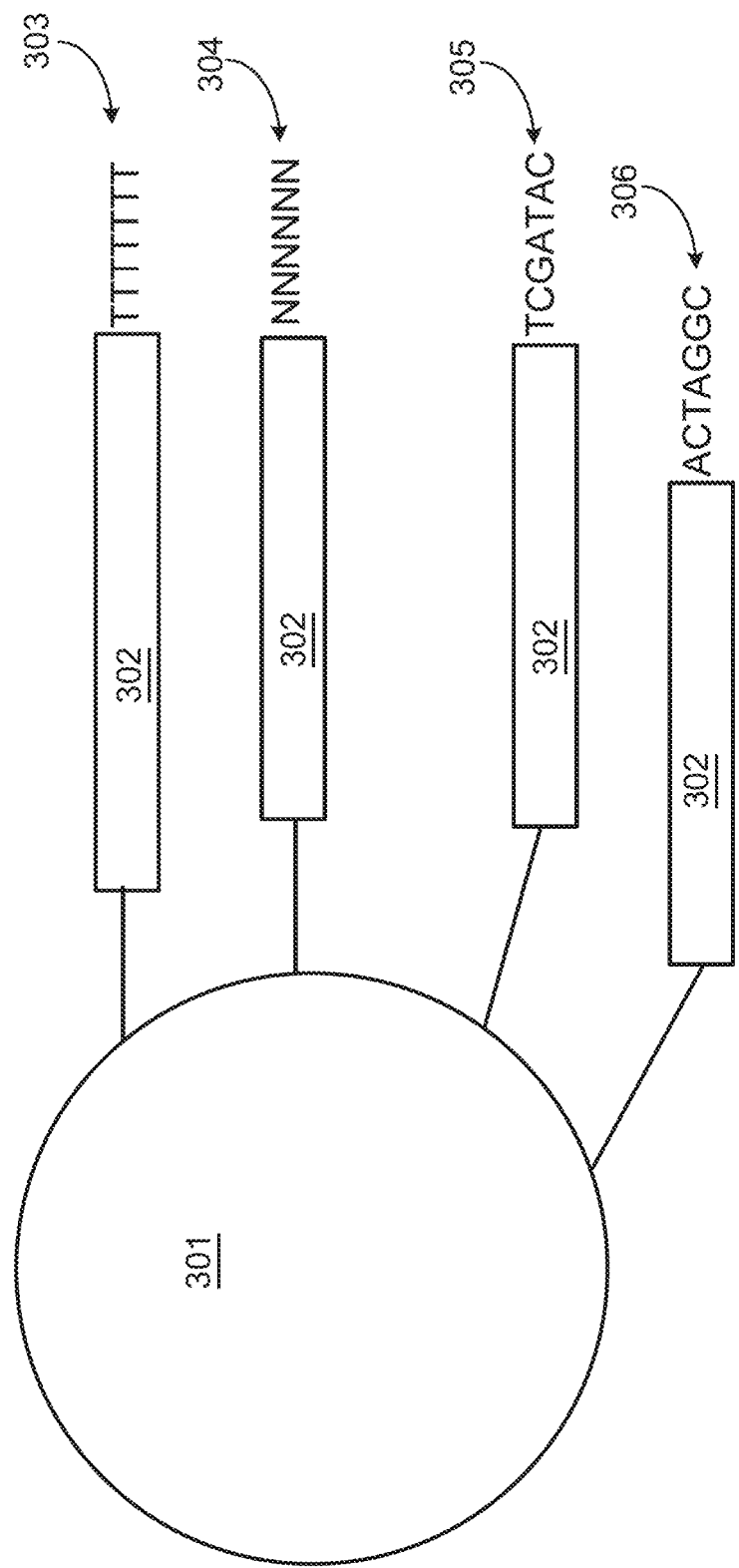
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) a capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent.

Figure 4:
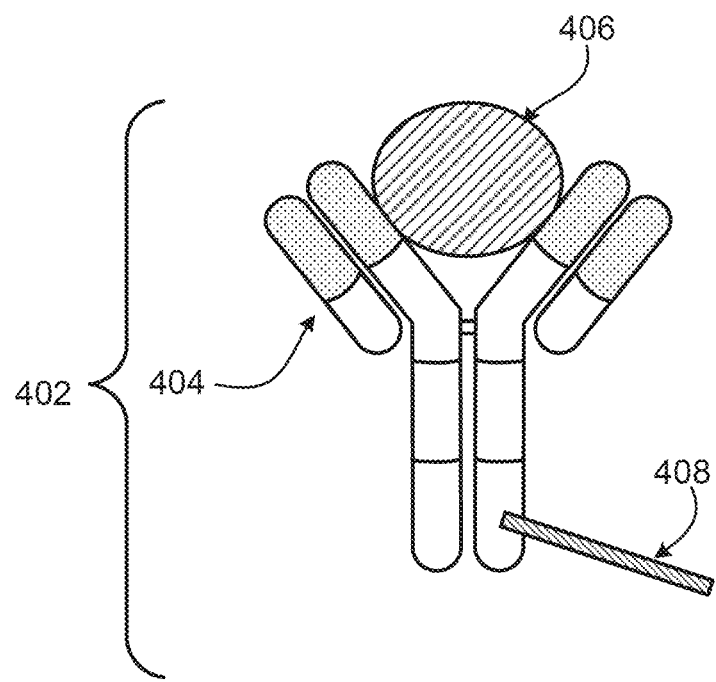
FIG. 4 is a schematic diagram of an exemplary analyte capture agent.

FIG. 4 is a schematic diagram of an exemplary analyte capture agent 402 comprised of an analyte-binding moiety 404 and an analyte-binding moiety barcode domain 408. The exemplary analyte-binding moiety 404 is a molecule capable of binding to an analyte 406 and the analyte capture agent is capable of interacting with a spatially-barcoded capture probe. The analyte-binding moiety can bind to the analyte 406 with high affinity and/or with high specificity. The analyte capture agent can include an analyte-binding moiety barcode domain 408, a nucleotide sequence (e.g., an oligonucleotide), which can hybridize to at least a portion or an entirety of a capture domain of a capture probe. The analyte-binding moiety barcode domain 408 can comprise an analyte binding moiety barcode and a capture handle sequence described herein. The analyte-binding moiety 404 can include a polypeptide and/or an aptamer. The analyte-binding moiety 404 can include an antibody or antibody fragment (e.g., an antigen-binding fragment).

Figure 5:
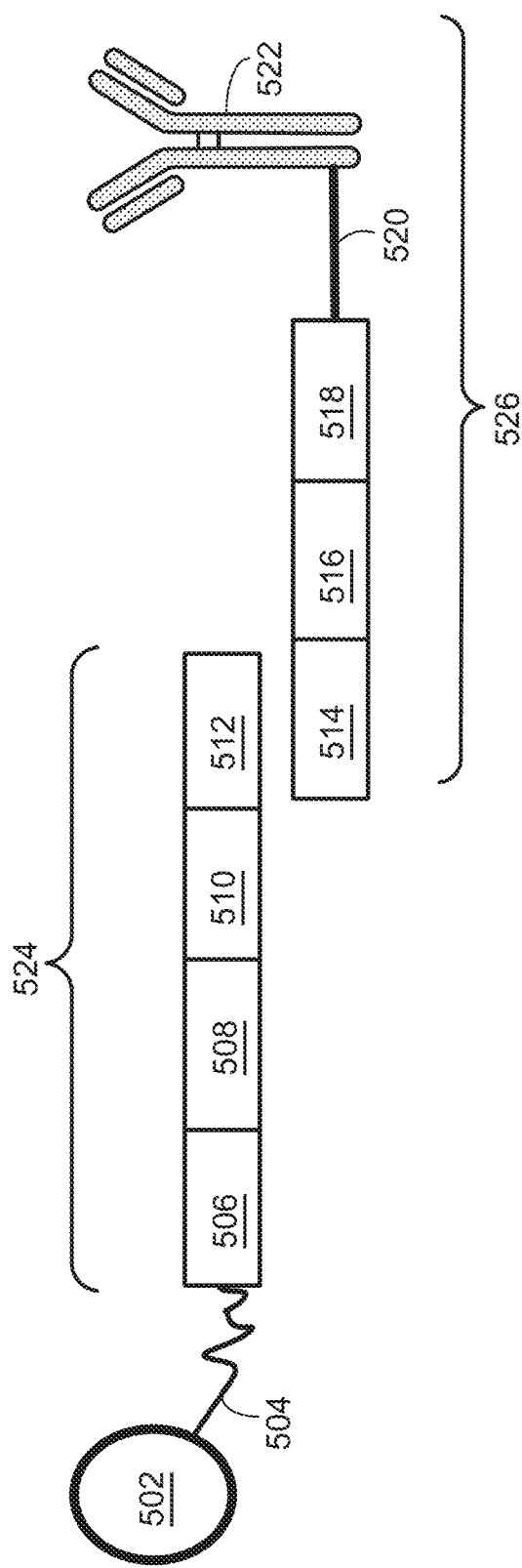
FIG. 5 is a schematic diagram depicting an exemplary interaction between a feature-immobilized capture probe 524 and an analyte capture agent 526.

FIG. 5 is a schematic diagram depicting an exemplary interaction between a feature-immobilized capture probe 524 and an analyte capture agent 526. The feature-immobilized capture probe 524 can include a spatial barcode 508 as well as functional sequences 506 and UMI 510, as described elsewhere herein. The capture probe can also include a capture domain 512 that is capable of binding to an analyte capture agent 526. The analyte capture agent 526 can include a functional sequence 518, analyte binding moiety barcode 516, and a capture handle sequence 514 that is capable of binding to the capture domain 512 of the capture probe 524. The analyte capture agent can also include a linker 520 that allows the capture agent barcode domain 516 to couple to the analyte binding moiety 522.

Figure 6A:
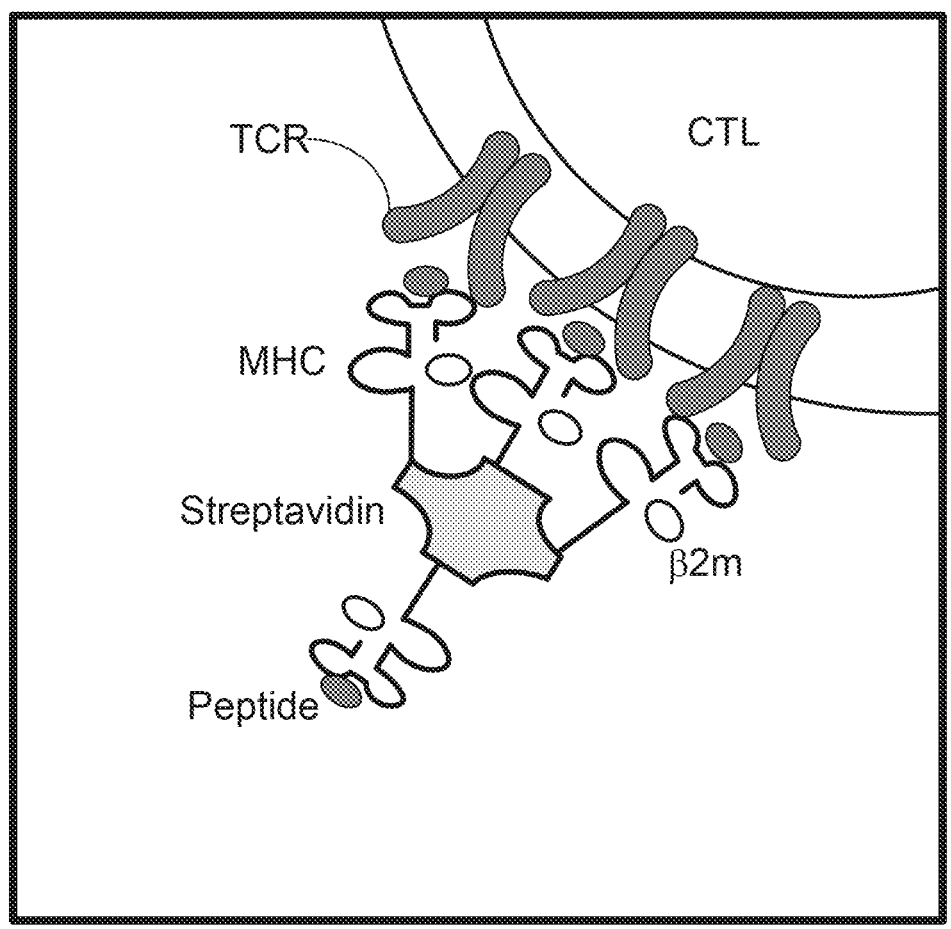
Figure 6B:
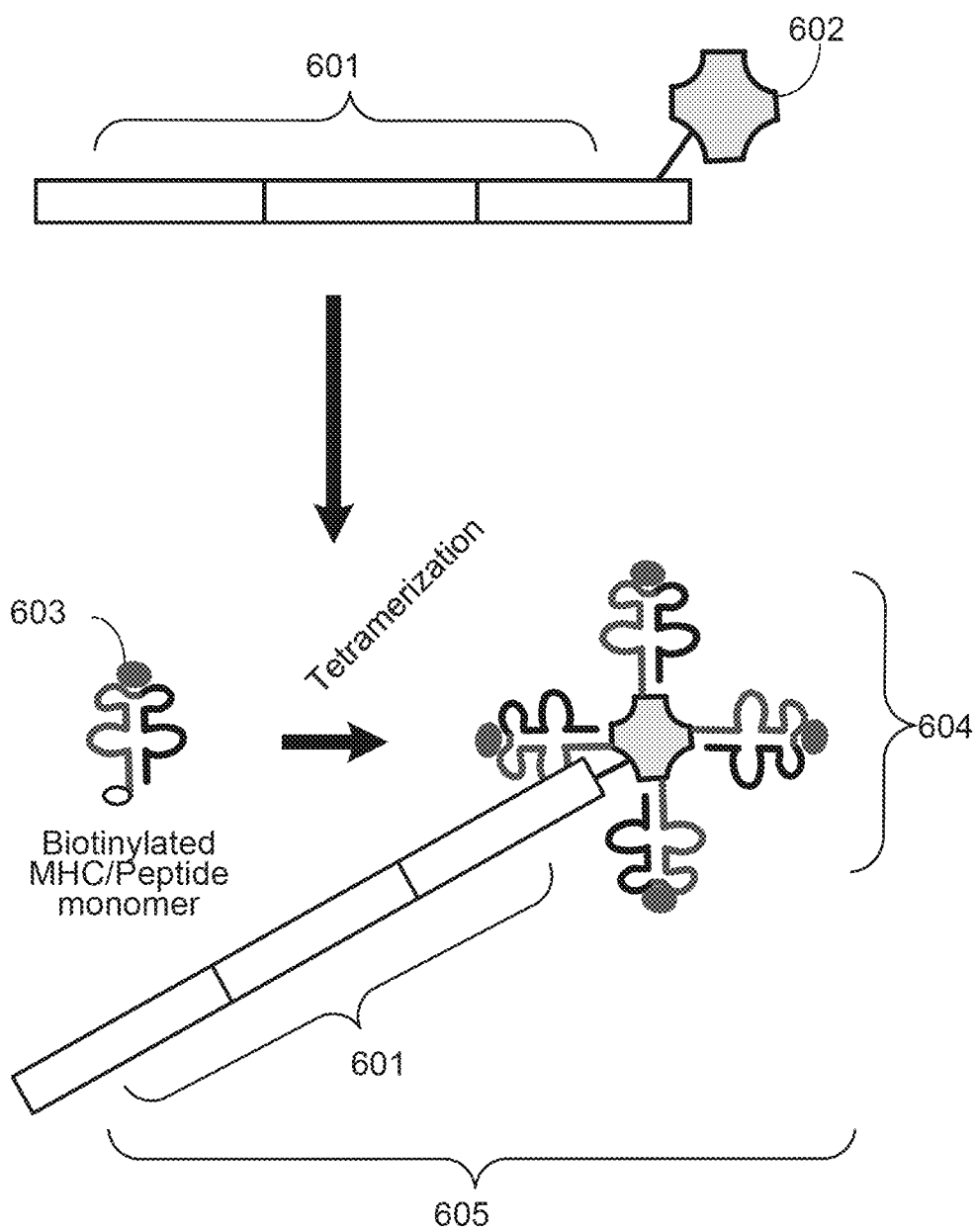

FIGS. 6A, 6B, and 6C are schematics illustrating how streptavidin cell tags can be utilized in an array-based system to produce a spatially-barcoded cell or cellular contents. For example, as shown in FIG. 6A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 6B, a capture agent barcode domain 601 can be modified with streptavidin 602 and contacted with multiple molecules of biotinylated MHC 603 such that the biotinylated MHC 603 molecules are coupled with the streptavidin conjugated capture agent barcode domain 601. The result is a barcoded MHC multimer complex 1105. As shown in FIG. 6B, the capture agent barcode domain sequence 601 can identify the MHC as its associated label and also includes optional functional sequences such as sequences for hybridization with other oligonucleotides. As shown in FIG. 6C, one example oligonucleotide is capture probe 606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 606 may at first be associated with a feature (e.g., a gel bead) and released from the feature. In other embodiments, capture probe 606 can hybridize with a capture agent barcode domain 601 of the MHC-oligonucleotide complex 605. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 606 or capture agent barcode domain 601. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 606 spatial barcode sequence may be used to identify a feature and the sequence derived from spatial barcode sequence on the capture agent barcode domain 601 may be used to identify the particular peptide MHC complex 604 bound on the surface of the cell (e.g., when using MHC-peptide libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a connected probe (e.g., a ligation product) or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form a connected probe (e.g., a ligation product) with a template (e.g., a DNA or RNA template, such as an analyte or an intermediate agent, or portion thereof), thereby creating ligation products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a connected probe (e.g., a ligation product). In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the connected probe (e.g., a ligation product) is released from the analyte. In some instances, the connected probe (e.g., a ligation product) is released using an endonuclease (e.g., RNAse H). The released connected probe (e.g., a ligation product) can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

The sandwich process is described in PCT Patent Application Publication No. WO 2020/123320, which is incorporated by reference in its entirety.

II. Proximity Ligation and Spatial Sequencing

Featured herein are methods of detecting the abundance of an analyte (e.g., mRNA, protein) using proximity ligation. Proximity ligation takes advantage of hybridization or association of multiple (e.g., two) oligonucleotides to adjacent areas (e.g., sequences) of an analyte. When the oligonucleotides are in close proximity to one another, a ligation reaction is performed, joining the two oligonucleotides. Because a proximity ligation reaction should only occur in sequence-specific areas of a sample, it allows for targeted detection of an analyte(s) that associates with or hybridizes to the multiple oligonucleotides. Thus, the efficiency of target capture and identification is increased compared to a system that uses one oligonucleotide to associate with (e.g., hybridize to, attach to, or bind to) an analyte.

In some embodiments, provided herein are methods and materials for determining a location of at least one analyte in a biological sample based on proximity ligation of a first oligonucleotide and a second oligonucleotide. In some embodiments, the methods provided herein include determining a location of an analyte interaction (e.g., a host analyte-viral analyte interaction) in a biological sample. In some embodiments, proximity ligation of the first oligonucleotide to the second oligonucleotide and capture of the ligation product (e.g., an oligonucleotide that includes the first oligonucleotide and the second oligonucleotide ligated together) is used to determine the location of at least one analyte in a biological sample. For example, the ligation product generated from the ligation of (i) a first oligonucleotide bound to a first analyte-binding moiety to (ii) a second oligonucleotide bound to a second analyte-binding moiety based on the proximity of the first and second analyte-binding moieties is used to determine a location of least one analyte in a biological sample.

Also provided herein is a method of determining a location of a host analyte-pathogen-derived analyte interaction in a biological sample where the pathogen-derived analyte includes a pathogen-derived nucleic acid analyte. In some cases, the method uses proximity ligation between a first antigen binding moiety that bind to a host analyte and a second oligonucleotide that binds to a pathogen-derived nucleic acid analyte (e.g., viral nucleic acid analyte) to determine the location of a host analyte-pathogen-derived nucleic acid analyte interaction in the biological sample.

(a) Proximity Ligation Using a First Analyte-Binding Moiety and a Second Analyte-Binding Moiety In some instances, the proximity ligation methods disclosed herein utilize a first analyte-binding moiety and a second analyte-binding moiety that interact with different analytes in proximity to one another (e.g., within about 400 nm of each other (e.g., about 300 nm, about 200 nm, about 150 nm, about 100 nm, about 50 nm, about 25 nm, about 10 nm, or about 5 nm)). In some embodiments, a first analyte-binding moiety is an analyte capture agent (e.g., any of the exemplary analyte capture agents described herein). In some embodiments, the first analyte-binding moiety is a first protein. In some embodiments, the first analyte-binding moiety is a first antibody. For example, the first antibody can include, without limitation, a monoclonal antibody, recombinant antibody, synthetic antibody, a single domain antibody, a single-chain variable fragment (scFv), and or an antigen-binding fragment (Fab). In some instances, the first analyte-binding moiety binds to a protein in a sample. In some embodiments, the first analyte-binding moiety binds to a cell surface analyte (e.g., any of the exemplary cell surface analytes described herein). In some embodiments, binding of the analyte is performed metabolically. In some embodiments, binding of the analyte is performed enzymatically.

In some embodiments, the methods include a secondary antibody that binds to a primary antibody. In some embodiments, the first antibody binds to a first analyte-binding moiety, and a first secondary antibody binds to the first antibody. In some embodiments, multiple secondary antibodies can bind to a first antibody, allowing the detection of an analyte to be amplified. In some embodiments, an oligonucleotide (e.g., a first oligonucleotide) as disclosed herein is bound to a secondary antibody, and the oligonucleotide can be used in a proximity ligation reaction disclosed herein.

In some embodiments, the unbound primary antibodies are washed away before a secondary antibody is added. In some embodiments, the unbound secondary antibodies are washed away before any downstream steps. A wash step can be performed using any wash solution disclosed herein (e.g., 1×PBST).

In some embodiments, the first analyte-binding moiety is a non-protein. For example, the first analyte-binding moiety is an aptamer. In some embodiments, the first analyte-binding moiety is a DNA aptamer. In some embodiments, the DNA aptamer is a single-stranded DNA molecule. In some embodiments, the first analyte-binding moiety is an RNA aptamer. In some embodiments, the aptamer is synthetic. In some embodiments, the aptamer is a single-stranded RNA molecule. In some embodiments, the aptamer binds to a specific target, including but not limited to, proteins, peptides, carbohydrates, small molecules, and toxins. In some embodiments, an aptamer as disclosed herein binds into its target by folding into tertiary structures. In some instances, the aptamer includes a sequence that can be used for the proximity ligation methods disclosed herein. In some instances, a sequence that can be used for the proximity ligation methods disclosed herein is affixed to the aptamer.

In some embodiments, the first analyte-binding moiety binds to an analyte present inside a cell (e.g., any of the exemplary analytes present inside a cell). For example, analytes can be derived from cytosol, from cell nuclei, from mitochondria, from microsomes, and more generally, from any other compartment, organelle, or portion of a cell. In some embodiments, the first analyte-binding moiety binds to an analyte present on the surface of or outside a cell. Analytes present on the surface of or outside a cell can include without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified.

In some embodiments, the first analyte-binding moiety binds a non-protein. In some embodiments, the first analyte-binding moiety binds cell surface analytes that are post-translationally modified. In such embodiments, the first analyte-binding moiety can be specific for one or more cell surface analytes based on a given state of post-translational modification (e.g., phosphorylation, glycosylation, ubiquitination, nitrosylation, methylation, acetylation or lipidation), such that a cell surface analyte profile can include post-translational modification information of one or more analytes.

In some embodiments, also provided herein is a second analyte-binding moiety that binds to a second analyte. In some instances, the second analyte-binding moiety is an analyte capture agent (e.g., any of the exemplary analyte capture agents described herein). In some embodiments, the second analyte-binding moiety is a second protein. In some embodiments, the second analyte-binding moiety is a second antibody. For example, the second antibody can include, without limitation, a monoclonal antibody, recombinant antibody, synthetic antibody, a single domain antibody, a single-chain variable fragment (scFv), and or an antigen-binding fragment (Fab). In some instances, the second analyte-binding moiety binds to a protein in a sample. In some embodiments, the second analyte-binding moiety binds to a cell surface analyte (e.g., any of the exemplary cell surface analytes described herein). In some embodiments, the second analyte-binding moiety binds to an analyte present inside a cell (e.g., any of the exemplary analytes present inside a cell). In some embodiments, the second analyte-binding moiety binds a non-protein. For example, the second analyte-binding moiety can bind to a nucleic acid. In some embodiments, the second analyte-binding moiety binds cell surface analytes that are post-translationally modified. In such embodiments, the second analyte-binding moiety can be specific for one or more cell surface analytes based on a given state of post-translational modification (e.g., phosphorylation, glycosylation, ubiquitination, nitrosylation, methylation, acetylation or lipidation), such that a cell surface analyte profile can include post-translational modification information of one or more analytes.

In some embodiments, the methods disclosed herein include a secondary antibody that binds to the second analyte-binding moiety (e.g., a primary antibody) to amplify the signal. In some embodiments, multiple secondary antibodies can bind to the primary antibody associated with the second analyte binding moiety, allowing the detection of an analyte to be amplified. In some embodiments, an oligonucleotide (e.g., a second oligonucleotide) as disclosed herein is bound to a secondary antibody, and the oligonucleotide can be used in a proximity ligation reaction disclosed herein.

In some embodiments, the unbound primary antibodies are washed away before a secondary antibody is added. In some embodiments, the unbound secondary antibodies are washed away before any downstream steps. A wash step can be performed using any wash solution disclosed herein (e.g., 1×PBST).

In some embodiments, the second analyte-binding moiety is a non-protein. For example, the second analyte-binding moiety is an aptamer. In some embodiments, the second analyte-binding moiety is a DNA aptamer. In some embodiments, the DNA aptamer is a single-stranded DNA molecule. In some embodiments, the second analyte-binding moiety is an RNA aptamer. In some embodiments, the aptamer is synthetic. In some embodiments, the aptamer is a single-stranded RNA molecule. In some embodiments, the aptamer binds to a specific target, including but not limited to, proteins, peptides, carbohydrates, small molecules, and toxins. In some embodiments, an aptamer as disclosed herein binds into its target specifically by folding into tertiary structures. In some instances, the aptamer includes a sequence that can be used for the proximity ligation methods disclosed herein. In some instances, a sequence that can be used for the proximity ligation methods disclosed herein is affixed to the aptamer.

In some embodiments, the second analyte-binding moiety binds to an analyte present inside a cell (e.g., any of the exemplary analytes present inside a cell). For example, analytes can be derived from cytosol, from cell nuclei, from mitochondria, from microsomes, and more generally, from any other compartment, organelle, or portion of a cell. In some embodiments, the second analyte-binding moiety binds to an analyte present on the surface of or outside a cell. Analytes present on the surface of or outside a cell can include without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified.

In some embodiments, the second analyte-binding moiety binds a non-protein. In some embodiments, the second analyte-binding moiety binds cell surface analytes that are post-translationally modified. In such embodiments, the second analyte-binding moiety can be specific for one or more cell surface analytes based on a given state of post-translational modification (e.g., phosphorylation, glycosylation, ubiquitination, nitrosylation, methylation, acetylation or lipidation), such that a cell surface analyte profile can include post-translational modification information of one or more analytes.

In some embodiments, the first analyte-binding moiety and the second analyte-binding moiety each bind to the same analyte. For example, the first analyte-binding moiety binds to a sequence of a first polypeptide and the second analyte-binding moiety also binds to the first polypeptide, but at a different sequence. In some embodiments, the first analyte-binding moiety and/or second analyte-binding moiety each bind to a different analyte. For example, in some embodiments, the first analyte-binding moiety binds to a first polypeptide and the second analyte-binding moiety binds to a second polypeptide. In some embodiments, the first analyte-binding moiety binds to a first polypeptide and the second analyte-binding moiety binds to a post-translational modification of the first polypeptide. In some embodiments, the first analyte-binding moiety binds to a first polypeptide and the second analyte-binding moiety binds to a post-translational modification of a second polypeptide. In some embodiments, the first analyte-binding moiety binds to a first post-translational modification and the second analyte-binding moiety binds to a second polypeptide. In some embodiments, the first analyte-binding moiety binds to a first post-translational modification and the second analyte-binding moiety binds to a second post-translational modification of a second polypeptide.

In some embodiments, the first and/or second analyte includes, but is not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments.

In some embodiments, the first analyte and the second analyte interact with each other in the biological sample. In some embodiments, the first analyte and the second analyte interact with each other via a protein-protein interaction. In a non-limiting example, the first analyte can be a receptor polypeptide and a second analyte can be a ligand polypeptide. However, nearly any interaction both on the surface of a cell and within a cell (i.e., where the analytes are in proximity to one another) can be used herein.

In some embodiments, the methods include more than two analyte-binding moieties (e.g., at least three analyte-binding moieties, at least four analyte-binding moieties, at least five analyte-binding moieties, at least six analyte-binding moieties, or at least seven or more analyte-binding moieties). In some embodiments, each of the three or more analyte-binding moieties binds to a different analyte. For example, a first analyte-binding moiety binds to a first polypeptide, a second analyte-binding moiety binds to a post-translational modification of a second polypeptide, and a third analyte-binding moiety binds to a lipid.

(i) Host Analytes and Viral Analytes

In another aspect, the methods provided herein include determining a location of a host analyte-viral analyte interaction in a biological sample. Viruses rely on host protein-viral protein-interactions for virus replication, propagation and suppression of host defense mechanisms. The infectious life cycle of a virus includes interactions with host proteins at each stage including: attachment and entry into the host cell, translation of viral RNA by host ribosomes, viral genome replication, assembly of viral particles, and release of the viral particles from the cell. In order to determine the presence or abundance of an interaction between a host protein and a viral protein, the methods described herein include proximity ligation.

In some cases, the methods provided herein use proximity ligation between a first antigen binding moiety that binds specifically to a host analyte and a second antigen-binding moiety that binds specifically to a viral analyte to determine the location of a host analyte-viral analyte interaction in the biological sample. It is understood that, unless specified, the term first and second are interchangeable and can be reversed. For example, the first antigen binding moiety can bind to a host analyte and the second antigen-binding moiety can bind to a viral analyte; or the second antigen binding moiety can bind to a host analyte and the first antigen-binding moiety can bind to a viral analyte. When the host analyte and the viral analyte are within about 400 nm of each other (e.g., about 300 nm, about 200 nm, about 150 nm, about 100 nm, about 50 nm, about 25 nm, about 10 nm, or about 5 nm) from each other in the biological sample proximity ligation results in a ligation product. The ligation product is an indication of host analyte-viral analyte interaction in the particular location in the biological sample.

In some embodiments, where the methods provided herein include determining a location of a host analyte-viral analyte interaction in a biological sample, the first analyte is a host analyte and the second analyte is a viral analyte. In some embodiments, the first analyte is a viral analyte and the second analyte is a host analyte. In some embodiments, the first analyte and second analyte each bind to a viral analyte.

In some embodiments where the method includes a first and/or second analyte binding moiety that binds to a host analyte, the host analyte is a host protein. In some cases, the host protein is host cellular machinery that is co-opted for viral propagation. Non-limiting examples of host proteins involved in viral infection and propagation include proteins involved in endocytosis (e.g., RAB5, RAB7, and RAB10), nuclear import (e.g., NUP98, NUP153, Importin-5, and KPNB1), genome replication and transcription (HSP90, POLII, P14 and SNRP70), nuclear export (NXF1, Hsc79, and CRM1), translation (GRSF-1, P58IPK), posttranslational modification, protein transport/cell motor proteins (e.g., actin, and RAB11) as described in Watanabe et al., *Cell Host & Microbe*, 7(6): 427-39 (2010), which is herein incorporated by reference in its entirety.

In some embodiments, the host protein is a cell surface moiety. A cell surface moiety can be any moiety present on the surface of a cell to which a viral analyte interacts either directly or indirectly. A viral analyte may interact directly with the cell surface moiety (e.g., a receptor on the surface of the cell) as a means to invade the cell. Non-limiting examples of cell surface moieties include common viral receptors such as sialylated glycans; cell adhesion molecules such as immunoglobulin superfamily members and integrins; and phosphatidylserine receptors (see Maginnis, *J. Mol. Bio.*, 17: 2590-2611 (2018), which is herein incorporated by reference in its entirety).

In some embodiments, the host protein is a sialyated glycan or sialic acid. For example, the sialic acid can be 5-N-acetyl neuraminic acid (Neu5Ac) in which the 5-carbon position is modified with an N-acetyl group. In another example, the sialic acid can be a ganglioside. Sialyated glycans are receptors for enveloped coronaviruses (+ssRNA) and influenza viruses (−ssRNA), and the nonenveloped reoviruses (dsRNA) and polyomaviruses (dsDNA) (see Maginnis et al. 2018).

In some embodiments, the host protein is a cell motor protein. In some embodiments the host protein is a protein transport protein. In such cases, a cell motor protein and/or protein transport protein is utilized by a virus to transport virus or virus-related material within the cell. For example, a cytoplasmic dynein cell motor protein can be used to transport virus or virus-related material to the nucleus. In such cases, the first and/or second analyte binding moiety can hybridize to the cytoplasmic dynein cell motor protein. In another example, a kinesin protein can be used to transport virus or virus-related material within the cell. In such cases, the first and/or second analyte-binding moiety can hybridize to the kinesin protein. In some embodiments, the host protein is a microtubule. For example, the host protein is TUBA1A or TUBB3.

Many viruses rely on nuclear proteins for replication, which means the viral genome must enter the nucleus of the host cell. The nuclear envelope can act as a barrier between the cytoplasm and the nucleus controlling the transport into and out of the nucleus. In some cases, the host analyte is the nuclear envelope where the first and/or second analyte binding moiety hybridize to the nuclear envelope. The first and/or second analyte-binding moiety can bind to the inner nuclear membrane and/or the outer nuclear membrane. Embedded in the nuclear envelope are nuclear pore complexes that include 30 different proteins called nucleoporins. The nucleoporins are arranged to form the pore through which a virus and/or virus-related material can pass. In some embodiments, the first and/or second analyte-binding moiety hybridize to the one or more nuclear pore proteins. In some embodiments, the nuclear pore protein is a nucleoporin. The nuclear envelope is also associated with nuclear laminin which plays a role regulating entry into the nucleus. Nuclear lamina is composed of lamins, including type A and type B and intermediate filaments. In some embodiments, the first and/or second analyte-binding moiety that hybridizes to a host analyte hybridizes to a nuclear lamina. Non-limiting examples of host proteins associated with the nuclear envelope include: LMNA, LMNB, NUP98, and EMD.

In some embodiments, the first and/or second analyte-binding moiety that hybridizes to a host analyte hybridizes to a host ribosomal protein. In some embodiments, the host analyte is a host protein involved in translational initiation. In some embodiments, the host analyte is a host protein involved in translation. In some embodiments, the host analyte is a host protein involved in posttranslational modifications.

In some embodiments, the first and/or second analyte-binding moiety that hybridizes to a host analyte hybridizes to a host protein associated with the endosome. Non-limiting examples of host proteins associated with the endosome include RAB5A, RAB4, EEA1, RAB7, RAB9, RAB 11, CLTB, and CTLC (see Russell et al., *Curr. Opin. Cell Bio.*, 18(4):422-428 (2006), which is incorporated herein by reference in its entirety). In some embodiments, the first and/or second analyte-binding moiety that hybridizes to a host protein associated with the endocytic pathway. Non-limiting examples of host proteins associated with the endocytic pathway are described in Grant and Donaldson, *Nat. Rev. Mol. Cell Biol.*, 10(9): 597-608 (2009), which is incorporated by reference herein in its entirety.

In some embodiments, the first and/or second analyte-binding moiety that hybridizes to a host analyte hybridizes to a host protein associated with the endoplasmic reticulum. Non-limiting examples of host proteins associated with the endoplasmic reticulum include: CANX, GRP78, GRP94, CALR, BCAP31, SEC13 and PDI.

In some embodiments, the first and/or second analyte-binding moiety that hybridizes to a host analyte hybridizes to a host protein associated with the Golgi. Non-limiting examples of host proteins associated with the Golgi include: FTCD, STX6, RCAS1, TGN38, GOLGB1, and GOLGA2.

In some embodiments, the first and/or second analyte-binding moiety that hybridizes to a host analyte hybridizes to a host protein associated with autophagosomes and/or lysosomes. Non-limiting examples of host proteins associated with autophagosomes and/or lysosomes include ATGS, LAMP1, LAMP2, GLB1, ATG12, and LC3.

Also provided herein are methods where the first and/or second analyte-binding moiety that hybridizes to a viral analyte is a viral protein. The viral protein to which the first and/or second analyte-binding moieties can hybridize include viral proteins that a virus utilizes for replication, propagation and/or suppression of host defenses. The viral protein can include viral proteins from enveloped viruses and non-enveloped viruses. Non-limiting examples of enveloped viruses include: Baculo-, Bunya-, Corona-, Filo-, Herpes-, Lenti-, Orthomyxo-, Paramyxo-, Pox-, Retro-, Rhabdo-, and Togaviridae (see Lenard, J., *Encyclopedia of Virology*, 308-314 (2008), which is herein incorporated by reference in its entirety). In some cases, the viral protein can be a nonstructural protein (e.g., an nsp protein), a regulatory protein (e.g., a Vpg protein), and/or an accessory protein. Non-structural proteins include virus proteins expressed in infected cells but not incorporated into the viral particles. In some cases, the viral protein is a component of the mature assembled virus particle, including nucleocapsid core proteins (e.g., a gag protein), enzymes (e.g., a polymerase), and membrane components (e.g., an envelope protein). In some embodiments, the viral protein includes a gag, a pol, and/or an env protein encoded within the retroviral genome.

In some embodiments, the viral protein is a viral capsid. In some cases, capsid proteins bind to host cell surface moieties. In some cases capsid proteins are glycoproteins. Binding of the glycoprotein can lead to fusion of the virion particle with the host cell membrane, which leads to release of the viral capsid containing the viral genome into the cytoplasm. Non-limiting examples of viral capsid proteins include: VP1, VP2, VP3, and VP4.

In some embodiments, the viral protein is a glycoprotein. Non-limiting examples of glycoproteins include those glycoproteins from viruses including: influenza virus (e.g., haemaglutinin and neuraminidase); SARS-CoV and SARS-CoV2 (e.g., spike(S) glycoprotein); hepatitis C (e.g., E1 and E2); HIV (e.g., gp120, gp160, and gp41); Ebola virus (e.g., spike protein Gp1 and spike protein Gp2); Dengue virus (e.g., E dimer); and Chikungunya virus (e.g., E1 and E2) (see Banerjee and Mukhopadhyay, *Virusdisease*, 27(1):1-11 (2016), which is herein incorporated by reference in its entirety). Glycoproteins can include envelope proteins, membrane proteins, and spike proteins.

In some embodiments, the viral protein in an integrase protein. An integrase protein catalyzes the integration of virally derived DNA into the host cell DNA in the nucleus. For example, a viral protein can be a retroviral integrase protein. In some cases, the viral protein is a HIV integrase.

In some embodiments, the viral protein is a viral polymerase protein. Viral polymerases include, without limitation, RNA-dependent RNA polymerase, RNA-dependent DNA polymerase, DNA-dependent RNA polymerase, and DNA-dependent RNA polymerase. In some embodiments, the viral protein is part of the viral polymerase complex (see, Rialdi, *Cell,* 169: 679-692 (2017), which is herein incorporated by reference in its entirety). The viral polymerase complex can co-opt the host RNA exosome machinery to enable translation of viral mRNA.

In some embodiments, the viral protein is a nucleocapsid. Nucleocapsid proteins can facilitate viral replication. Non-limiting examples of nucleocapsid proteins include: retroviral nucleocapsid proteins (e.g., lentivirus p7, p8, and p10 and retrovirus p10, p12, and p15); SARS-CoV and SARS-CoV2 (e.g., nucleocapsid); influenza virus (e.g., nucleocapsid protein) and Ebola virus (e.g., nucleoprotein (NP)).

In some embodiments, the viral protein is a protein that suppresses the host antiviral response. Non-limiting examples of viruses that encode proteins that suppress the host antiviral immune response include; influenza A (e.g., encodes an endoribonuclease PA-X protein), herpes virus (e.g., vhs proteins), and SARS-CoV (e.g., non-structural protein 1 (nsp1) (see Gaucherand et al., *Cell Reports,* 27:776-792 (2019), which is herein incorporated by reference in its entirety). In some cases, the viral protein can be part of a viral inclusion in the cytoplasm that enables and/or evades the host antiviral response. For example, following Ebola virus infection, Ebola viruses sequesters stress granules in viral inclusions, which helps to limit the antiviral response of the cell (see, Nelson et al., *J. Virol.,* 90(16): 7268-7284 (2016), which is herein incorporated by reference in its entirety).

In some embodiments, the viral analyte is from a virus selected from an Influenza Type A virus, an ebolavirus, human immunodeficiency virus-1, human immunodeficiency virus-2, West Nile virus, avian influenza, severe acute respiratory syndrome coronavirus-1, severe acute respiratory syndrome coronavirus-2, Zika virus, or any combination thereof.

(b) First Oligonucleotide

In some embodiments of any of the methods of determining a location of at least one analyte in a biological sample, a first oligonucleotide is bound (e.g., conjugated or otherwise attached using any of the methods described herein) to a first analyte-binding moiety. For example, the first oligonucleotide can be covalently linked to the first analyte-binding moiety. In some embodiments, the first oligonucleotide is bound to the first analyte-binding moiety via its 5' end. In some embodiments, the first oligonucleotide includes a free 3' end. In some embodiments the first oligonucleotide is bound to the first analyte-binding moiety via its 3' end. In some embodiments, the first oligonucleotide includes a phosphate at its free 5' end.

In some embodiments, the first oligonucleotide is about 10 to about 150 nucleotides (e.g., about 10, about 20, about 30, about 40, about 50, about 60, about 70, about 80, about 90, about 100, about 110, about 120, about 130, about 140, or about 150 nucleotides) in length. In some instances, the first oligonucleotide is a DNA molecule comprising DNA nucleotides (e.g., adenine (A), thymine (T), guanine (G), and cytosine (C)).

In some embodiments, the oligonucleotide is bound to the first analyte-binding moiety via a first linker (e.g., any of the exemplary linkers described herein). For example, the first oligonucleotide is bound to the first analyte-binding moiety via a first linker. In some embodiments, the first linker is a first cleavable linker (e.g., any of the exemplary cleavable linkers described herein). In some embodiment, the first linker is a linker with photo-sensitive chemical bonds (e.g., photo-cleavable linkers). In some embodiments, the first linker is a cleavable linker that can undergo induced dissociation.

In some embodiments, a first oligonucleotide is bound (e.g., attached via any of the methods described herein) to a first analyte-binding domain via a 5' end.

In some embodiments, a first oligonucleotide includes from 5' to 3': a functional sequence (e.g., any of the exemplary functional sequences described herein), a first barcode, and a first bridge sequence. In some embodiments, the functional sequence of the first oligonucleotide includes a primer sequence. The primer sequence can be used to bind a primer that can be used to amplify (i) at least part of the first oligonucleotide and (ii) at least part of any additional oligonucleotides (e.g., the first oligonucleotide) ligated to the first oligonucleotide. In some embodiments, a first oligonucleotide includes from 5' to 3': a functional sequence (e.g., any of the exemplary functional sequences described herein) and a first bridge sequence. In some embodiments, a first oligonucleotide includes from 5' to 3': a first barcode sequence and a first bridge sequence. In some embodiments, a first oligonucleotide includes from 5' to 3': a functional sequence (e.g., any of the exemplary functional sequences described herein) and a first barcode sequence. In some embodiments, a first oligonucleotide includes from 5' to 3': a functional sequence (e.g., any of the exemplary functional sequences described herein), a first barcode sequence, and a first bridge sequence. In some embodiments, a second oligonucleotide includes from 5' to 3': a second barcode and a functional sequence (e.g., any of the exemplary functional sequences described herein). In some embodiments, a second oligonucleotide includes from 5' to 3': a second barcode and a capture probe capture domain sequence.

In some embodiments, a first oligonucleotide is bound (e.g., attached via any of the methods described herein) to a first analyte-binding domain via a 3' end. In some embodiments, a first oligonucleotide includes from 3' to 5': a capture probe capture domain sequence, a first barcode, and a first bridge sequence. In some embodiments, a first oligonucleotide includes from 3' to 5': a capture probe capture domain sequence and a first bridge sequence. In some embodiments, a first oligonucleotide includes from 3' to 5': a first barcode sequence and a first bridge sequence. In some embodiments, a first oligonucleotide includes from 3' to 5': a capture probe capture domain sequence and a first barcode sequence.

In some embodiments, the first oligonucleotide is bound to a first (e.g., primary) antibody. In some embodiments, the first oligonucleotide is bound to a first (e.g., primary) antibody using a cleavable linker. In some embodiments, the first oligonucleotide is bound to a secondary antibody. In some embodiments, the first oligonucleotide is bound to a secondary antibody using a cleavable linker.

In some embodiments, the first oligonucleotide comprises a first barcode that is used to identify the first analyte-binding moiety to which it is bound. The first barcode can be any of the exemplary barcodes described herein. In some embodiments, the first barcode is a first capture agent barcode domain that serves as a proxy for identification of an interaction between a first analyte and a first analyte-binding moiety. In some embodiments, the first oligonucleotide comprises a capture probe capture domain. In some embodiments, the first oligonucleotide comprises a primer-binding sequence.

In some embodiments, a first oligonucleotide further includes a first bridge sequence that enables the first oligonucleotide to hybridize a second sequence (e.g., a second bridge sequence on a second oligonucleotide). In some embodiments, a bridge sequence can include a sequence that is at least partially complementary to one or more additional sequences (e.g., a third oligonucleotide, one or more additional oligonucleotides, a proximity probe, or a padlock oligonucleotide) and functions to bring a first oligonucleotide and a second oligonucleotide in sufficient proximity that the first and second oligonucleotides can be ligated and extended. In some embodiments, the first bridge sequence of the first oligonucleotide has at least 80%, at least 85%, at least 90%, at least 91%, at least 92%, at least 93%, at least 94%, at least 95%, at least 96%, at least 97%, at least 98%, or at least 99% sequence identity to a sequence that is 100% complementary of the second bridge sequence or to one or more additional sequences (e.g., a third oligonucleotide, one or more additional oligonucleotides, a proximity probe, or a padlock oligonucleotide).

In some embodiments, a first bridge sequence is about 5 nucleotides to about 50 nucleotides (e.g., about 5 nucleotides to about 45 nucleotides, about 5 nucleotides to about 40 nucleotides, about 5 nucleotides to about 35 nucleotides, about 5 nucleotides to about 30 nucleotides, about 5 nucleotides to about 25 nucleotides, about 5 nucleotides to about 20 nucleotides, about 5 nucleotides to about 15 nucleotides, about 5 nucleotides to about 10 nucleotides, about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 25 nucleotides, about 10 nucleotides to about 20 nucleotides, about 10 nucleotides to about 15 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 25 nucleotides, about 15 nucleotides to about 20 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 25 nucleotides, about 25 nucleotides to about 45 nucleotides, about 25 nucleotides to about 40 nucleotides, about 25 nucleotides to about 35 nucleotides, about 25 nucleotides to about 30 nucleotides, about 30 nucleotides to about 45 nucleotides, about 30 nucleotides to about 40 nucleotides, about 30 nucleotides to about 35 nucleotides, about 35 nucleotides to about 45 nucleotides, about 35 nucleotides to about 40 nucleotides, or about 40 nucleotides to about 45 nucleotides).

In some embodiments, a first bridge sequence includes a sequence that is substantially complementary to a second bridge sequence. In some embodiments, a first oligonucleotide includes from 5' to 3': a functional sequence (e.g., any of the exemplary functional sequences described herein; e.g., a primer binding sequence), a first barcode, and a first bridge sequence.

In some embodiments, a first oligonucleotide includes a sequence including one or more uracil nucleotides. In some embodiments, including one or more uracil nucleotides in a first oligonucleotide enables use of DNA polymerases that include uracil-binding specificity. In some embodiments, the DNA polymerase includes a mutation in the uracil-binding pocket that enables the ability to read and amplify templates containing uracil bases. Using DNA polymerase having the ability to read and amplify templates containing uracil enables strand-specific elongation. A non-limiting example of a DNA polymerase that includes the ability to read and amplify templates containing uracil bases include: Q5U Hot Start High-Fidelity DNA polymerase. As used herein, "a U(+) polymerase" refers to a polymerase that has the ability to read and amplify templates containing uracil nucleotides. In some embodiments, the method includes using a DNA polymerase that does not include the ability to read and amplify templates containing uracil. As used herein, "a U(−) polymerase" refers to a polymerase that does not have the ability to read and amplify templates containing uracil nucleotides.

In some embodiments, a first oligonucleotide includes about 2, 3, 4, 5, 6, 7, 8, 9, 10, or more uracil nucleotides. In some embodiments, the one or more uracil nucleotides in the first oligonucleotide are a contiguous sequence of two or more uracil nucleotides. In some embodiments, the one or more uracil nucleotides in the first oligonucleotide include one or more contiguous sequences of two or more uracil nucleotides.

In some embodiments, a first oligonucleotide includes from 5' to 3': a functional sequence (e.g., any of the exemplary functional sequences described herein), one or more uracils nucleotides, a first barcode, and a first bridge sequence. In some embodiments, a first oligonucleotide includes from 5' to 3': a functional sequence (e.g., any of the exemplary functional sequences described herein), one or more uracil nucleotides, a UMI, a first barcode, and a first bridge sequence.

In some embodiments, a first barcode is used to identify the first analyte-binding moiety to which it is bound. The first barcode can be any of the exemplary barcodes described herein.

In some embodiments, a first oligonucleotide includes a capture probe capture domain sequence. In some instances, the capture probe capture domain sequence is a homopolymeric sequence (e.g., a poly(A) sequence). In some embodiments, a first oligonucleotide includes a capture probe capture domain sequence and a second oligonucleotide also includes a capture probe capture domain sequence. For example, the sequence of the capture probe capture domain of the first oligonucleotide is not complementary to the sequence of the capture probe capture domain of the second oligonucleotide. In another example, the sequence of the capture probe capture domain of the first oligonucleotide is the same as the sequence of the capture probe capture domain of the second oligonucleotide. In some embodiments, a first oligonucleotide includes a second capture probe capture domain and a second oligonucleotide includes a first capture probe capture domain. In some embodiments, a first oligonucleotide includes a first capture probe capture domain and a second oligonucleotide includes a second capture probe capture domain.

(c) Second Oligonucleotide

In some embodiments of any of the methods of determining a location of at least one analyte in a biological sample as described herein, a second oligonucleotide is bound (e.g., conjugated or otherwise attached using any of the methods described herein) to a second analyte-binding moiety. For example, the second oligonucleotide can be covalently linked to the second analyte-binding moiety. In some embodiments, the second oligonucleotide is bound to the second analyte-binding moiety via its 5' end. In some embodiments, the second oligonucleotide includes a free 3' end. In some embodiments the second oligonucleotide is bound to the second analyte-binding moiety via its 3' end. In some embodiments, the second oligonucleotide includes a free 5' end.

In some embodiments, the second oligonucleotide is about 10 to about 150 nucleotides (e.g., about 10, about 20, about 30, about 40, about 50, about 60, about 70, about 80, about 90, about 100, about 110, about 120, about 130, about 140, or about 150 nucleotides) in length. In some instances, the second oligonucleotide is a DNA molecule comprising DNA nucleotides (e.g., adenine (A), thymine (T), guanine (G), and cytosine (C)).

In some embodiments, the oligonucleotide is bound to the second analyte-binding moiety via a second linker (e.g., any of the exemplary linkers described herein). For example, the second oligonucleotide is bound to the second analyte-binding moiety via a second linker. In some embodiments, the second linker is a second cleavable linker (e.g., any of the exemplary cleavable linkers described herein). In some embodiment, the second linker is a linker with photo-sensitive chemical bonds (e.g., photo-cleavable linkers). In some embodiments, the second linker is a cleavable linker that can undergo induced dissociation.

In some embodiments, a second oligonucleotide is bound (e.g., attached via any of the methods described herein) to a second analyte-binding domain via a 3' end. In some embodiments, a second oligonucleotide includes from 3' to 5': a capture probe capture domain sequence, a second barcode, and a second bridge sequence. In some embodiments, a second oligonucleotide includes from 3' to 5': a capture probe capture domain sequence and a second bridge sequence. In some embodiments, a second oligonucleotide includes from 3' to 5': a second barcode and a second bridge sequence.

In some embodiments, a second oligonucleotide is bound (e.g., attached via any of the methods described herein) to a second analyte-binding domain via a 5' end. In some embodiments, a second oligonucleotide includes from 5' to 3': a functional sequence (e.g., any of the exemplary functional sequences described herein), a second barcode, and a second bridge sequence. In some embodiments, a second oligonucleotide includes from 5' to 3': a functional sequence (e.g., any of the exemplary functional sequences described herein) and a second bridge sequence. In some embodiments, a second oligonucleotide includes from 5' to 3': a functional sequence (e.g., any of the exemplary functional sequence described herein) and a second barcode. In some embodiments, a second oligonucleotide includes from 5' to 3': a second barcode and a functional sequence (e.g., any of the exemplary functional sequences described herein). In some embodiments, a second oligonucleotide includes from 5' to 3': a second barcode and a capture probe capture domain sequence. In some embodiments, a second oligonucleotide includes from 5' to 3': a second bridge sequence, a second barcode, and a second functional sequence (e.g., any of the exemplary functional sequences described herein). In some embodiments, a second oligonucleotide includes from 5' to 3': a second barcode and a second bridge sequence. In some embodiments, the functional sequence of the second oligonucleotide includes a primer sequence. The primer sequence can be used to bind a primer that can be used to amplify (i) at least part of the second oligonucleotide and (ii) at least part of any additional oligonucleotides (e.g., the first oligonucleotide) ligated to the second oligonucleotide.

In some embodiments, a second oligonucleotide is bound (e.g., attached via any of the methods described herein) to a second analyte-binding domain via a 3' end. In some embodiments, a second oligonucleotide includes from 3' to 5': a capture probe capture domain sequence, a second barcode, and a second bridge sequence. In some embodiments, a second oligonucleotide includes from 3' to 5': a capture probe capture domain sequence and a second bridge sequence. In some embodiments, a second oligonucleotide includes from 3' to 5': a second barcode and a second bridge sequence. In some embodiments, a second oligonucleotide includes from 3' to 5': a capture probe capture domain sequence and a second barcode.

In some embodiments, the second oligonucleotide comprises a second barcode that is used to identify the second analyte-binding moiety to which it is bound. The second barcode can be any of the exemplary barcodes described herein. In some embodiments, the second barcode is a second capture agent barcode domain that serves as a proxy for identification of an interaction between a second analyte and a second analyte-binding moiety. In some embodiments, the second oligonucleotide comprises a capture probe capture domain sequence. In some embodiments, the second oligonucleotide comprises a primer-binding sequence.

In some embodiments of any of the methods of determining a location of at least one analyte in a biological sample, a first oligonucleotide is bound (e.g., attached via any of the methods described herein) to a first analyte-binding domain via a 5' end and a second oligonucleotide is bound (e.g., attached via any of the method described herein) to a second analyte-binding domain via a 3' end. In some embodiments, a first oligonucleotide includes from 5' to 3': a functional sequence (e.g., any of the exemplary functional sequences described herein), a first barcode, and a first bridge sequence, and a second oligonucleotide includes from 3' to 5': a capture probe capture domain sequence, a second barcode, and a second bridge sequence.

In some embodiments of any of the methods of determining a location of at least one analyte in a biological sample, a first oligonucleotide is bound (e.g., attached via any of the methods described herein) to a first analyte-binding domain via a 5' end and a second oligonucleotide is bound (e.g., attached via any of the method described herein) to a second analyte-binding domain via a 5' end. In some embodiments, a first oligonucleotide includes from 5' to 3': a functional sequence (e.g., any of the exemplary functional sequences described herein), a first barcode, and a first bridging sequence and a second oligonucleotide includes from 5' to 3': a second bridging sequence, a second barcode, and a second functional sequence (e.g., any of the exemplary functional sequences described herein). In some embodiments, a first oligonucleotide includes from 5' to 3': a functional sequence (e.g., any of the exemplary functional sequences described herein) and a first barcode, and a second oligonucleotide includes from 5' to 3': a second barcode and a second functional sequence (e.g., any of the exemplary functional sequences described herein).

In some embodiments, a second oligonucleotide further includes a second bridge sequence that enables the second oligonucleotide to hybridize a first bridge sequence (e.g., a first bridge sequence on the first oligonucleotide). In some embodiments, the second bridge sequence of the second oligonucleotide has at least 80%, at least 85%, at least 90%, at least 91%, at least 92%, at least 93%, at least 94%, at least 95%, at least 96%, at least 97%, at least 98%, or at least 99% sequence identity to a sequence that is 100% complementary to a first bridge sequence or to one or more additional sequences (e.g., a third oligonucleotide, one or more additional oligonucleotides, a proximity probe, or a padlock oligonucleotide).

In some embodiments, a second bridge sequence is about 5 nucleotides to about 50 nucleotides (e.g., about 5 nucleotides to about 45 nucleotides, about 5 nucleotides to about 40 nucleotides, about 5 nucleotides to about 35 nucleotides, about 5 nucleotides to about 30 nucleotides, about 5 nucleotides to about 25 nucleotides, about 5 nucleotides to about 20 nucleotides, about 5 nucleotides to about 15 nucleotides, about 5 nucleotides to about 10 nucleotides, about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 25 nucleotides, about 10 nucleotides to about 20 nucleotides, about 10 nucleotides to about 15 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 25 nucleotides, about 15 nucleotides to about 20 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 25 nucleotides, about 25 nucleotides to about 45 nucleotides, about 25 nucleotides to about 40 nucleotides, about 25 nucleotides to about 35 nucleotides, about 25 nucleotides to about 30 nucleotides, about 30 nucleotides to about 45 nucleotides, about 30 nucleotides to about 40 nucleotides, about 30 nucleotides to about 35 nucleotides, about 35 nucleotides to about 45 nucleotides, about 35 nucleotides to about 40 nucleotides, or about 40 nucleotides to about 45 nucleotides).

In some embodiments, a second bridge sequence includes a sequence that is substantially complementary to a first bridge sequence. In some embodiments, a second oligonucleotide includes from 5' to 3': a functional sequence (e.g., any of the exemplary functional sequences described herein; e.g., a primer binding sequence), a second barcode, and a second bridge sequence.

In some embodiments, a second oligonucleotide includes a sequence including one or more uracil nucleotides. In some embodiments, including one or more uracil nucleotides in a second oligonucleotide enables use of DNA polymerases that include the ability to read and amplify templates containing uracil bases. For example, using DNA polymerase having the ability to read and amplify templates containing uracil enables strand-specific elongation.

In some embodiments, a second oligonucleotide includes about 2, 3, 4, 5, 6, 7, 8, 9, 10, or more uracil nucleotides. In some embodiments, the one or more uracil nucleotides in the second oligonucleotide are a contiguous sequence of two or more uracil nucleotides. In some embodiments, the one or more uracil nucleotides in the second oligonucleotide include one or more contiguous sequences of two or more uracil nucleotides.

In some embodiments, a second oligonucleotide includes from 5' to 3': a functional sequence (e.g., any of the exemplary functional sequences described herein), one or more uracil nucleotides, a second barcode, and a second bridge sequence. In some embodiments, a first oligonucleotide includes from 5' to 3': a functional sequence (e.g., any of the exemplary functional sequences described herein), one or more uracil nucleotides, a UMI, a second barcode, and a second bridge sequence.

In some embodiments, a second barcode is used to identify the second analyte-binding moiety to which it is bound. The second barcode can be any of the exemplary barcodes described herein.

In some embodiments of any of the methods of determining a location of an interaction between a first analyte and a second analyte in a biological sample, a first oligonucleotide is bound (e.g., attached via any of the methods described herein) to a first analyte-binding domain via a 5' end and a second oligonucleotide is bound (e.g., attached via any of the method described herein) to a second analyte-binding domain via a 3' end. In some embodiments, a first oligonucleotide includes from 5' to 3': a functional sequence (e.g., any of the exemplary functional sequences described herein), a first barcode, and a first bridge sequence, and a second oligonucleotide includes from 3' to 5': a capture probe capture domain sequence, a second barcode, and a second bridge sequence.

In some embodiments of any of the methods of determining a location of an interaction between a first analyte and a second analyte in a biological sample, a first oligonucleotide is bound (e.g., attached via any of the methods described herein) to a first analyte-binding domain via a 5' end and a second oligonucleotide is bound (e.g., attached via any of the method described herein) to a second analyte-binding domain via a 5' end. In some embodiments, a first oligonucleotide includes from 5' to 3': a functional sequence (e.g., any of the exemplary functional sequences described herein), a first barcode, and a first bridge sequence and a second oligonucleotide includes from 5' to 3': a second functional sequence (e.g., any of the exemplary functional sequences described herein), a second barcode, and a second bridge sequence. In some embodiments, a first oligonucleotide includes from 5' to 3': a functional sequence (e.g., any of the exemplary functional sequences described herein) and a first barcode, and a second oligonucleotide includes from 5' to 3': a second functional sequence (e.g., any of the exemplary functional sequences described herein) and a second barcode.

(d) Third Oligonucleotide

In some embodiments of any of the methods of determining a location of at least one analyte in a biological sample, a third oligonucleotide (i.e., a splint oligonucleotide) hybridizes to the first oligonucleotide and the second oligonucleotide via the first bridge sequence and the second bridge sequence, respectively. In some embodiments, a first sequence of the third oligonucleotide is at least partially complementary to the first bridge sequence. In some embodiments, a second sequence of the third oligonucleotide is at least partially complementary to the second bridge sequence. In some embodiments, the third oligonucleotide hybridizes to the first bridge sequence prior to hybridizing to the second bridge sequence. In some embodiments, the third oligonucleotide hybridizes to the second bridge sequence prior to hybridizing to the first bridge sequence. In some embodiments, the third oligonucleotide hybridizes simultaneously to the first bridge sequence and the second bridge sequence. As such, the third oligonucleotide serves as a splint in bringing the first and second oligonucleotides adjacent to one another, if they are present in a reaction.

In some embodiments of any of the methods of determining a location of at least one analyte in a biological sample, a third oligonucleotide is hybridized to the first oligonucleotide and the second oligonucleotide via the first barcode and the second barcode, respectively. In some embodiments, a first sequence of the third oligonucleotide is at least partially complementary to the first barcode. In some embodiments, a second sequence of the third oligonucleotide is at least partially complementary to the second barcode. In some embodiments, the third oligonucleotide hybridizes to the first barcode prior to hybridizing to the second barcode. In some embodiments, the third oligonucleotide hybridizes to the second barcode prior to hybridizing to the first barcode. In some embodiments, the third oligonucleotide hybridizes simultaneously to the first barcode and the second barcode. In some embodiments, a third oligonucleotide includes from 5' to 3' a second sequence that binds to a sequence of the second oligonucleotide (e.g., a second barcode) and a first sequence that binds to a sequence of the first oligonucleotide (e.g., a first barcode). In some embodiments, a third oligonucleotide includes from 5' to 3' a first sequence that binds to a sequence of the first oligonucleotide (e.g., a first barcode) and a second sequence that binds to a sequence of the second oligonucleotide (e.g., a second barcode).

In some embodiments, the third oligonucleotide includes a sequence of about 10 nucleotides to about 100 nucleotides (e.g., a sequence of about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 90 nucleotides, about 60 nucleotides to about 80 nucleotides, about 60 nucleotides to about 70 nucleotides, about 70 nucleotides to about 90 nucleotides, about 70 nucleotides to about 80 nucleotides, or about 80 nucleotides to about 90 nucleotides).

In some embodiments, the third oligonucleotide hybridized to both the first bridge sequence and second bridge sequence enables ligation of the first oligonucleotide and the second oligonucleotide. In some embodiments, a ligase is used. In some aspects, the ligase includes a DNA ligase. In some instances, the DNA ligase is a T4 DNA ligase. In some aspects, the ligase includes RNA ligase. In some aspects, the ligase includes T4 RNA ligase.

In some embodiments, the ligation of the first oligonucleotide and the second oligonucleotide includes enzymatic or chemical ligation. In some embodiments, the ligation of the first oligonucleotide and the second oligonucleotide includes enzymatic ligation. In some embodiments, the ligation reaction utilizes ligase (e.g., any of the exemplary ligases described herein). For example, the ligase is a splintR ligase. In some aspects, the methods include "sticky-end" or "blunt-end" ligations. Additionally, single-stranded ligation can be used to perform proximity ligation on a single-stranded nucleic acid molecule.

In some embodiments, the ligase creates a ligation product (e.g., a full length oligonucleotide) that includes both the first oligonucleotide and the second oligonucleotide. In some embodiments, a third oligonucleotide hybridizes to a first oligonucleotide and a second oligonucleotide when the first analyte-binding domain and the second analyte-binding domain are about 400 nm distance (e.g., about 300 nm, about 200 nm, about 150 nm, about 100 nm, about 50 nm, about 25 nm, about 10 nm, or about 5 nm) from each other.

In some embodiments, when the third oligonucleotide is hybridized to the first bridge sequence and the second bridge sequence, the first oligonucleotide and the second oligonucleotide are directly adjacent in a manner that enables ligation in the presence of a ligase enzyme. In some embodiments, when the first oligonucleotide and the second nucleotide are directly adjacent to each other, a ligation reaction occurs between a free 3' of the first oligonucleotide and a free 5' of the second oligonucleotide. In some embodiments, when the first oligonucleotide and the second oligonucleotide are directly adjacent to each other, a ligation reaction occurs directly between a free 3' end of the second oligonucleotide and a free 5' end of the first oligonucleotide. In some embodiments, when the third oligonucleotide is hybridized to the first bridge sequence and the second bridge sequence, the first oligonucleotide and the second oligonucleotide are not directly adjacent. For example, when the third oligonucleotide is hybridized to the first bridge sequence and the second bridge sequence, the first oligonucleotide and the second oligonucleotide requires additional nucleotides to hybridize to the third oligonucleotide in between the first and second oligonucleotides in order for a ligation product to be generated. In some embodiments, additional nucleotide sequences can be added between the first oligonucleotide and the second oligonucleotide by DNA polymerases (e.g., any of the exemplary DNA polymerases described herein).

In some embodiments, the third oligonucleotide is designed so that a portion of the nucleic acid sequence of the third oligonucleotide does not hybridize to either the first bridge sequence or the second bridge sequence. This portion of the third oligonucleotide can be located between the first sequence that is complementary to the first bridge sequence and the second sequence that is complementary to the second bridge sequence. In some embodiments, the third oligonucleotide is designed so that a portion of the nucleic acid sequence of the third oligonucleotide does not hybridize to either the first barcode or the second barcode. This portion of the third oligonucleotide can be located between the first sequence that is complementary to the first barcode and the second sequence that is complementary to the second barcode. In some embodiments, the portion of the of the nucleic acid sequence of the third oligonucleotide that does not hybridize to the first or second bridge sequence forms a secondary structure (e.g., stem-loop, hairpins, or other structure typically formed by single stranded DNA).

In some embodiments of any of the methods of determining a location of at least one analyte in a biological sample, the method includes use of more than one splint (i.e., more than one third) oligonucleotide. In some embodiments, one splint oligonucleotide affixes (e.g., hybridizes or ligates) to the first oligonucleotide. In some embodiments, a different splint oligonucleotide affixes (e.g., hybridizes or ligates) to the second oligonucleotide. In some embodiments, a first sequence of the additional splint oligonucleotide is at least partially complementary to a sequence of the first oligonucleotide (e.g., a functional sequence (e.g., any of the exemplary functional sequences described herein)). In some embodiments, a second sequence of the additional oligonucleotide is at least partially complementary to a sequence of the second oligonucleotide (e.g., a functional sequence (e.g., any of the exemplary functional sequences described herein)).

In some embodiments, one or more additional splint oligonucleotides comprise a sequence that is complementary or partially complementary to at least a portion of the third oligonucleotide. In some embodiments, the additional oligonucleotide hybridized to the first oligonucleotide includes a free 5' phosphate. In some embodiments, the third oligonucleotide hybridized to the first oligonucleotide includes a free 3' OH. In some embodiments, hybridization of the additional oligonucleotide and the third oligonucleotide to the first oligonucleotide enables ligation of the additional oligonucleotide to the third oligonucleotide via the free 5' phosphate of the additional nucleotide and the free 3' OH of the third oligonucleotide. In some embodiments, the additional oligonucleotide hybridized to the second oligonucleotide includes a free 3' OH. In some embodiments, the third oligonucleotide hybridized to the second oligonucleotide includes a free 5' phosphate. In some embodiments, hybridization of the additional oligonucleotide and the third oligonucleotide to the second oligonucleotide enables ligation of the additional oligonucleotide to the third oligonucleotide via the free 3' OH of the additional oligonucleotide and the free 5' phosphate of the third oligonucleotide.

In some embodiments, one of the additional oligonucleotides includes a capture probe capture domain sequence. In some embodiments, an additional oligonucleotide includes a priming sequence. In some embodiments, an additional oligonucleotide includes a capture probe capture domain sequence and a priming sequence. In some embodiments, an additional oligonucleotide includes from 5' to 3' a priming sequence and a capture probe capture domain sequence. In some embodiments, an additional oligonucleotide includes a capture probe capture domain sequence, a third functional sequence, and a priming sequence. In some embodiments, an additional oligonucleotide includes from 5' to 3' a priming sequence, a third functional sequence, and a capture probe capture domain sequence. In some embodiments, the third functional sequence is a cleavage domain (e.g., any of the exemplary cleavage domains described herein). In some embodiments, cleavage of the cleavage domain occurs before, contemporaneously with, or after ligation.

In some embodiments, the additional oligonucleotide is ligated to the third oligonucleotide using a ligase (e.g., any of the ligase enzymes described herein) thereby creating a ligation product. In some embodiments, the additional oligonucleotide is ligated to the 3' end of the third oligonucleotide and also ligated to the 5' end of the third oligonucleotide. In some embodiments, ligation of the additional oligonucleotide to the 3' end third oligonucleotide and the 5' end of the third oligonucleotide results in a ligation product that is circular. In some embodiments, the ligation product (e.g., any of the ligation products described herein) is amplified before contacting a capture probe on a spatial array. For example, the ligation product can be amplified using isothermal or non-isothermal amplification. A non-limiting example of isothermal amplification includes rolling circle amplification. Other methods of amplification are disclosed herein.

In some embodiments, the additional oligonucleotide (e.g., any of the additional oligonucleotides described herein) includes a sequence of about 10 nucleotides to about 100 nucleotides (e.g., a sequence of about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 90 nucleotides, about 60 nucleotides to about 80 nucleotides, about 60 nucleotides to about 70 nucleotides, about 70 nucleotides to about 90 nucleotides, about 70 nucleotides to about 80 nucleotides, or about 80 nucleotides to about 90 nucleotides).

(e) Capture Probe Capture Domain Sequence

In some embodiments, the first and/or second oligonucleotide include a capture probe capture domain sequence. In some instances, the first oligonucleotide comprises a capture probe capture domain sequence at its 5' end. In some instances, the first oligonucleotide comprises a capture probe capture domain sequence at its 3' end. In some instances, the second oligonucleotide comprises a capture probe capture domain sequence at its 5' end. In some instances, the second oligonucleotide comprises a capture probe capture domain sequence at its 3' end.

The capture probe capture domain sequence can include a sequence that is at least partially complementary to a sequence of a capture domain (e.g., any of the exemplary capture domains described herein). For example, a capture probe capture domain sequence can be a poly(A) sequence when the capture domain sequence is a poly(T) sequence. In another example, a capture probe capture domain sequence can be a random sequence (e.g., random hexamer) that is at least partially complementary to a capture domain sequence that is also a random sequence. In yet another example, a capture probe capture domain sequence can be a mixture of a homopolymeric sequence (e.g., a poly(T) sequence) and a random sequence (e.g., random hexamer) when a capture domain sequence is also a sequence that includes a homopolymeric sequence (e.g., a poly(A) sequence) and a random sequence. In some embodiments, the capture probe capture domain sequence includes ribonucleotides, deoxyribonucleotides, and/or synthetic nucleotides that are capable of participating in Watson-Crick type or analogous base pair interactions. In some embodiments, the capture probe capture domain sequence includes at least 10, 11, 12, 13, 14, 15, 16, 17, 18, 19, or 20 nucleotides. In some embodiments, the capture probe capture domain sequence includes at least 25, 30, or 35 nucleotides.

(f) Pre-Processing of Sample

Prior to addition of the probes, in some instances, biological samples can be stained using a wide variety of stains and staining techniques. In some instances, the biological sample is a section on a slide (e.g., a 10 µm section). In some instances, the biological sample is dried after placement onto a glass slide. In some instances, the biological sample is dried at 42° C. In some instances, drying occurs for about 1 hour, about 2, hours, about 3 hours, or until the sections become transparent. In some instances, the biological sample can be dried overnight (e.g., in a desiccator at room temperature).

In some embodiments, a sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin. In some instances, the methods disclosed herein include imaging the biological sample. In some instances, imaging the sample occurs prior to deaminating the biological sample. In some instances, the sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some instances, the stain is an H&E stain.

In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample.

In some embodiments, biological samples can be destained. Methods of destaining or discoloring a biological sample are known in the art, and generally depend on the nature of the stain(s) applied to the sample. For example, H&E staining can be destained by washing the sample in HCl, or any other acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in an acid (e.g., HCl). In some embodiments, destaining can include adding HCl to a downstream solution (e.g., permeabilization solution). In some embodiments, destaining can include dissolving an enzyme used in the disclosed methods (e.g., pepsin) in an acid (e.g., HCl) solution. In some embodiments, after destaining hematoxylin with an acid, other reagents can be added to the destaining solution to raise the pH for use in other applications. For example, SDS can be added to an acid destaining solution in order to raise the pH as compared to the acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., Nat Commun. 2015; 6:8390, Pirici et al., *J. Histochem. Cytochem.* 2009; 57:567-75, and Glass et al., J. Histochem. Cytochem. 2009; 57:899-905, the entire contents of each of which are incorporated herein by reference.

In some embodiments, immunofluorescence or immunohistochemistry protocols (direct and indirect staining techniques) can be performed as a part of, or in addition to, the exemplary spatial workflows presented herein. For example, tissue sections can be fixed according to methods described herein. The biological sample can be transferred to an array (e.g., capture probe array), wherein analytes (e.g., proteins) are probed using immunofluorescence protocols. For example, the sample can be rehydrated, blocked, and permeabilized (3×SSC, 2% BSA, 0.1% Triton X, 1 U/µl RNAse inhibitor for 10 minutes at 4° C.) before being stained with fluorescent primary antibodies (1:100 in 3×SSC, 2% BSA, 0.1% Triton X, 1 U/µl RNAse inhibitor for 30 minutes at 4° C.). The biological sample can be washed, coverslipped (in glycerol+1 U/µl RNAse inhibitor), imaged (e.g., using a confocal microscope or other apparatus capable of fluorescent detection), washed, and processed according to analyte capture or spatial workflows described herein.

In some instances, a glycerol solution and a cover slip can be added to the sample. In some instances, the glycerol solution can include a counterstain (e.g., DAPI).

As used herein, an antigen retrieval buffer can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases nonspecific binding of the antibodies to the array and/or biological sample (decreases background). Some embodiments provide for blocking buffers/blocking solutions that can be applied before and/or during application of the label, wherein the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

In some instances, the biological sample is deparaffinized. Deparaffinization can be achieved using any method known in the art. For example, in some instances, the biological samples are treated with a series of washes that include xylene and various concentrations of ethanol. In some instances, methods of deparaffinization include treatment of xylene (e.g., three washes at 5 minutes each). In some instances, the methods further include treatment with ethanol (e.g., 100% ethanol, two washes 10 minutes each; 95% ethanol, two washes 10 minutes each; 70% ethanol, two washes 10 minutes each; 50% ethanol, two washes 10 minutes each). In some instances, after ethanol washes, the biological sample can be washed with deionized water (e.g., two washes for 5 minutes each). It is appreciated that one skilled in the art can adjust these methods to optimize deparaffinization.

In some instances, the biological sample is decrosslinked. In some instances, the biological sample is decrosslinked in a solution containing TE buffer (comprising Tris and EDTA). In some instances, the TE buffer is basic (e.g., at a pH of about 9). In some instances, decrosslinking occurs at about 50° C. to about 80° C. In some instances, decrosslinking occurs at about 70° C. In some instances, decrosslinking occurs for about 1 hour at 70° C. Just prior to decrosslinking, the biological sample can be treated with an acid (e.g., 0.1M HCl for about 1 minute). After the decrosslinking step, the biological sample can be washed (e.g., with 1×PBST).

In some instances, the methods of preparing a biological sample for probe application include permeabilizing the sample. In some instances, the biological sample is permeabilized using a phosphate buffer. In some instances, the phosphate buffer is PBS (e.g., 1×PBS). In some instances, the phosphate buffer is PBST (e.g., 1×PBST). In some instances, the permeabilization step is performed multiple times (e.g., 3 times at 5 minutes each).

In some instances, the methods of preparing a biological sample for probe application include steps of equilibrating and blocking the biological sample. In some instances, equilibrating is performed using a pre-hybridization (pre-Hyb) buffer. In some instances, the pre-Hyb buffer is RNase-free. In some instances, the pre-Hyb buffer contains no bovine serum albumin (BSA), solutions like Denhardt's, or other potentially nuclease-contaminated biological materials.

In some instances, the equilibrating step is performed multiple times (e.g., 2 times at 5 minutes each; 3 times at 5 minutes each). In some instances, the biological sample is blocked with a blocking buffer. In some instances, the blocking buffer includes a carrier such as tRNA, for example yeast tRNA such as from brewer's yeast (e.g., at a final concentration of 10-20 μg/mL). In some instances, blocking can be performed for 5, 10, 15, 20, 25, or 30 minutes.

Any of the foregoing steps can be optimized for performance. For example, one can vary the temperature. In some instances, the pre-hybridization methods are performed at room temperature. In some instances, the pre-hybridization methods are performed at 4° C. (in some instances, varying the timeframes provided herein).

(g) Methods of Determining a Location of at Least One Analyte in a Biological Sample In some embodiments, disclosed are methods of determining a location of at least one analyte in a biological sample. In some aspects, the methods include binding a first analyte-binding moiety to a first analyte in the sample and binding a second analyte-binding moiety to a second analyte in the sample.

In some embodiments, provided herein is a method of determining a location of at least one analyte in a biological sample including: contacting the biological sample with a substrate including a plurality of capture probes, wherein a capture probe of the plurality of capture probes includes a spatial barcode and a capture domain; attaching a first analyte-binding moiety to the first analyte, wherein the first analyte-binding moiety is bound to a first oligonucleotide including a first barcode that is unique to the interaction between the first analyte and the first analyte-binding moiety; attaching a second analyte-binding moiety to the second analyte, wherein the second analyte-binding moiety is bound to a second oligonucleotide including a second barcode that is unique to the interaction between the second analyte and the second analyte-binding moiety; hybridizing a third oligonucleotide to the first oligonucleotide and to the second oligonucleotide; ligating the first oligonucleotide and the second oligonucleotide, thereby generating a ligation product including a capture probe capture domain sequence; and hybridizing the capture probe capture domain sequence to the capture domain; and (g) determining (i) all or a portion of the sequence of the spatial barcode or a complement thereof; (ii) all or a portion of the sequence of the first barcode or a complement thereof; (iii) all or a portion of the sequence of the second barcode or a complement thereof; and using the determined sequences of (i), (ii), and (iii) to identify the location and the abundance of the interaction between the first analyte and the second analyte in the biological sample.

In some aspects, after binding of the first and/or second analyte-binding moieties, the sample is washed (after adding the first and/or second analyte-binding moieties) to remove any unbound analyte-binding moieties. A wash step can be performed using any wash solution disclosed herein.

In some embodiments, the first oligonucleotide and/or the second oligonucleotide can be extended after binding to the analyte. A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

In some embodiments, the method includes disassociating the ligation product from the analyte-binding moieties. For instance, in some embodiments, the ligation product is cleaved from the analyte binding moieties. In some instances, the ligation product is then dissociated into a single-stranded molecules that can be detected by a capture probe as described herein. Dissociation can be performed using methods known in the art (i.e., increase in temperature, chemical means).

In some embodiments, all or a part of a ligation product (e.g., a full length oligonucleotide) can be amplified before, contemporaneously with, or after the ligation product (e.g., a full length oligonucleotide is contacted with the substrate that includes the capture probes). In some embodiments, after creation of the ligation product, the ligation product (i.e., including a first oligonucleotide, a second oligonucleotide, and a third oligonucleotide) can be cleaved from the first analyte-binding moiety and/or from the second analyte-binding moiety. In some embodiments, amplification includes PCR amplification. In some embodiments, amplification is by reverse transcription polymerase chain reaction (RT-PCR). In some embodiments, amplification includes a template switching oligonucleotides (TSOs). In some embodiments, amplification can be isothermal. In some embodiments, amplification is not isothermal.

(h) Methods for Determining Abundance and Location of Analyte Interactions by Detecting a Third Oligonucleotide In some embodiments, the method includes hybridizing a third oligonucleotide (e.g., a proximity probe) to all or a portion of a first oligonucleotide (e.g., any of the first probe oligonucleotides described herein) and all or a portion of a second oligonucleotide (e.g., any of the second probe oligonucleotides described herein). A non-limiting example of a method using a proximity probe to determine an interaction between a first and second analytes includes: contacting the biological sample with a substrate including a plurality of capture probes, wherein a capture probe of the plurality of capture probes comprises a spatial barcode and a capture domain; attaching a first analyte-binding moiety to the first analyte, wherein the first analyte-binding moiety is bound to a first oligonucleotide comprising a first barcode sequence; attaching a second analyte-binding moiety to the second analyte, wherein the second analyte-binding moiety is bound to a second oligonucleotide comprising a second barcode sequence; hybridizing a third oligonucleotide (e.g., a proximity probe) to a portion or all of the first barcode sequence in the first oligonucleotide and to a portion or all of the second barcode sequence in the second oligonucleotide, wherein the third oligonucleotide comprises a capture probe capture domain sequence; hybridizing the capture probe capture domain sequence to the capture domain; determining (i) all or a part of the sequence of the third oligonucleotide (e.g., a proximity probe) specifically bound to the capture domain, or a complement thereof, and (ii) all or a part of the sequence of the spatial barcode, or a complement thereof, and using the determined sequence of (i) and (ii) to identify the location of the first analyte and the second analyte in the biological sample. As used herein, a "proximity probe" can refer to a sequence that serves a proxy to identify an interaction between a first analyte and a second analyte. In some embodiments, determining all or part of the sequence of the third oligonucleotide (e.g., a proximity probe) includes determining (i) all or part of the sequence of the first barcode of the first oligonucleotide or a complement thereof and (ii) all or part of the sequence of the second barcode of the second oligonucleotide or a complement thereof.

In some embodiments, a third oligonucleotide (e.g., a proximity probe) includes a first sequence that is substantially complementary to all or a portion of a first oligonucleotide (e.g., any of the exemplary first oligonucleotides described herein), a second sequence that is substantially complementary to all or a portion of the second oligonucleotide (e.g., any of the exemplary second oligonucleotides described herein), and a capture probe capture domain (e.g., any of the exemplary capture probe capture domain sequences described herein). In some embodiments, the proximity probe also includes a functional sequence (e.g., any of the functional sequences described herein). In some embodiments, the first sequence of the proximity probe is substantially complementary to all or a portion of a first barcode sequence of the first oligonucleotide. In some embodiments, the second sequence of the proximity probe is substantially complementary to all or a portion of a second barcode sequence of the second oligonucleotide.

In some embodiments, the third oligonucleotide (e.g., the proximity probe) includes a sequence of about 10 nucleotides to about 100 nucleotides (e.g., a sequence of about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 90 nucleotides, about 60 nucleotides to about 80 nucleotides, about 60 nucleotides to about 70 nucleotides, about 70 nucleotides to about 90 nucleotides, about 70 nucleotides to about 80 nucleotides, or about 80 nucleotides to about 90 nucleotides).

In some instances, the third oligonucleotide (e.g., the proximity probe) hybridizes to the first oligonucleotide at a complementary sequence that is about 5, 6, 7, 8, 9, 10, 11, 12, 13, 14, 15, 16, 17, 18, 19, 20, 21, 22, 23, 24, 25, 26, 27, 28, 29, 30, or more nucleotides long. In some instances, the proximity probe hybridizes to the second oligonucleotide at a complementary sequence that is about 5, 6, 7, 8, 9, 10, 11, 12, 13, 14, 15, 16, 17, 18, 19, 20, 21, 22, 23, 24, 25, 26, 27, 28, 29, 30, or more nucleotides long.

In some embodiments, the third oligonucleotide (e.g., the proximity probe) further comprises a functional sequence. For example, the functional sequence is a primer binding sequence.

In some embodiments when the method includes a third oligonucleotide (e.g., a proximity probe), a washing step can be performed to remove proximity probes not bound to the first oligonucleotide and/or the second oligonucleotide. In some embodiments, two or more washing steps can be used to remove proximity probes that are not bound to the first and/or second oligonucleotides.

In some embodiments, following hybridization of the proximity probe to the first oligonucleotide and the second oligonucleotide, the first oligonucleotide and the second oligonucleotide are ligated together using any of the ligation methods and ligases described herein. For example, in some instances, ligation includes enzymatic ligation or chemical ligation. In some instances, the enzymatic ligation utilizes ligase such as a T4 DNA ligase.

In some embodiments, the method includes disassociating the proximity probe from the first oligonucleotide and the second oligonucleotide. In some embodiments, the method includes a releasing step that includes removing (e.g., disassociating) the proximity probe from the first and second oligonucleotides. In some embodiments, the releasing step includes contacting the proximity probe with an endoribonuclease. In some embodiments, two or more endoribonucleases can be used in the releasing step. Non-limiting examples of endoribonucleases include RNase H, RNase A, RNase C, or RNase I. In some embodiments, the releasing step is performed using an RNase H. Non-limiting examples of RNase H include: RNase H1, RNase H2, or RNase H1 and RNase H2. In some embodiments, a method using a proximity probe to determine an interaction between a first and second analytes includes ligating the first oligonucleotide to the second oligonucleotide prior to washing and/or releasing the third oligonucleotide from the first oligonucleotide and the second oligonucleotide.

(i) Methods for Determining Abundance and Location of Analyte Interactions Using Hybridized Proximity Oligonucleotides Also provided herein are methods for determining a location of an interaction between a first analyte and a second analyte in a biological sample by hybridizing the first oligonucleotide to the second oligonucleotide. A non-limiting example of a method for determining a location of an interaction between a first analyte and a second analyte in a biological sample by hybridizing the first oligonucleotide to the second oligonucleotide includes: contacting the biological sample with a substrate including a plurality of capture probes, wherein a capture probe of the plurality of capture probes includes a spatial barcode and a capture domain; attaching a first analyte-binding moiety to the first analyte, wherein the first analyte-binding moiety is bound to a first oligonucleotide including a first barcode that is unique to the interaction between the first analyte and the first analyte-binding moiety and a first bridge sequence; attaching a second analyte-binding moiety to the second analyte, wherein the second analyte-binding moiety is bound to a second oligonucleotide including a second barcode that is unique to the interaction between the second analyte and the second analyte-binding moiety and a second bridge sequence; (d) hybridizing the first bridge sequence to the second bridge sequence, thereby creating a hybridized proximity oligonucleotide including a capture probe capture domain sequence; (e) hybridizing the capture probe capture domain sequence to the capture domain; (f) determining (i) all or a portion of the sequence of the first barcode or a complement thereof; (ii) all or a portion of the sequence of the second barcode or a complement thereof, and (iii) all or a part of the sequence of the spatial barcode or a complement thereof, and using the determined sequence of (i), (ii), and (iii) to identify the location and the abundance of the interaction between the first analyte and the second analyte in the biological sample.

In some embodiments, hybridizing the first bridge sequence to the second bridge sequence creates a hybridized proximity oligonucleotide. As used herein "hybridized proximity oligonucleotide" can refer to a sequence that can be used as a proxy to identify an interaction between a first analyte and a second analyte. In some embodiments, the hybridized proximity oligonucleotide includes a double-stranded nucleic acid molecule. In some embodiments, the hybridized proximity oligonucleotide includes a single-stranded nucleic acid molecule. In some embodiments, the hybridized proximity oligonucleotide includes a nucleic acid molecule having single stranded overhangs on the 5' end, the 3' end, or both the 5' and 3' ends of the hybridized proximity oligonucleotide molecule.

In some embodiments, the hybridized proximity oligonucleotide includes a capture probe capture domain. In some embodiments, the hybridized proximity oligonucleotide is hybridized to a capture probe via a capture probe capture domain. In some cases, the hybridized proximity oligonucleotide can hybridize to the capture probe without further processing (releasing or extending of the hybridized proximity oligonucleotide). For example, a hybridized proximity oligonucleotide that includes a 5' single-stranded overhang can bind to a capture domain if the 5' overhang includes a capture probe capture domain sequence.

In some embodiments, the hybridized proximity oligonucleotide includes a sequence of about 10 nucleotides to about 300 nucleotides (e.g., a sequence of about 10 nucleotides to about 300 nucleotides, about 10 nucleotides to about 250 nucleotides, about 10 nucleotides to about 200 nucleotides, about 10 nucleotides to about 150 nucleotides, about 10 nucleotides to about 100 nucleotides, about 50 nucleotides to about 300 nucleotides, about 50 nucleotides to about 250 nucleotides, about 50 nucleotides to about 200 nucleotides, about 50 nucleotides to about 150 nucleotides, about 50 nucleotides to about 100 nucleotides, about 100 nucleotides to about 300 nucleotides, about 100 nucleotides to about 250 nucleotides, about 100 nucleotides to about 200 nucleotides, about 100 nucleotides to about 150 nucleotides, about 150 nucleotides to about 300 nucleotides, about 150 nucleotides to about 250 nucleotides, about 150 nucleotides to about 200 nucleotides, about 200 nucleotides to about 300 nucleotides, about 200 nucleotides to about 250 nucleotides, or about 250 nucleotides to about 300 nucleotides).

(j) Methods for Determining Abundance of Analyte Interaction Using Padlock Oligonucleotides Also provided herein are methods of determining abundance of an interaction between a first analyte and a second analyte in a biological sample using analyte-binding moieties and a padlock oligonucleotide. A non-limiting example of a method of determining abundance of an interaction between a first analyte and a second analyte in a biological sample using a padlock oligonucleotide includes: attaching a first analyte-binding moiety to the first analyte, wherein the first analyte-binding moiety is bound to a first oligonucleotide comprising a first barcode sequence; attaching a second analyte-binding moiety to the second analyte, wherein the second analyte-binding moiety is bound to a second oligonucleotide comprising a second barcode sequence; hybridizing a padlock oligonucleotide to the first oligonucleotide and the second oligonucleotide; circularizing the padlock oligonucleotide; amplifying the circularized padlock oligonucleotide using rolling circle amplification; and detecting the amplified circularized padlock oligonucleotide thereby identifying the abundance of the interaction between the first analyte and the second analyte in the biological sample. In some embodiments, the method further includes washing the biological sample after circularizing the padlock oligonucleotide in order to remove any unbound padlock oligonucleotides. In some embodiments, the method further includes ligating the first oligonucleotide and the second oligonucleotide after circularizing the padlock oligonucleotide. In some embodiments, the circularizing step comprises ligating the first sequence of the padlock oligonucleotide to the second sequence of the padlock oligonucleotide to create a circularized padlock oligonucleotide. In some embodiments, the amplifying step comprises: hybridizing one or more amplification primers to the padlock oligonucleotide; and amplifying the padlock oligonucleotide with a polymerase. In some embodiments, the polymerase has strand displacement activity. In some embodiments, the polymerase is a Phi29 DNA polymerase. In some embodiments, the amplification primer is substantially complementary to the backbone sequence of the padlock oligonucleotide. In some embodiments, the detecting step further includes: determining (i) all or a part of the sequence of the amplified circularized padlock oligonucleotide and using the determined sequence of the padlock oligonucleotide to identify the location of the analyte in the biological sample. In some embodiments, the determined sequence of the amplified circularized padlock oligonucleotide includes the first sequence of the padlock oligonucleotide and the second sequence of the padlock oligonucleotide.

As used herein, a "padlock oligonucleotide" refers to an oligonucleotide that has, at its 5' and 3' ends, sequences (e.g., a first sequence at the 5' end and a second sequence at the 3' end) that are complementary to a portion of the first oligonucleotide that is bound to a first analyte-binding moiety and a portion of the second oligonucleotide that is bound to a second-analyte binding moiety. Upon hybridization of the padlock oligonucleotide to the portion of the first oligonucleotide and a portion of the second oligonucleotide, the two ends of the padlock oligonucleotide are either brought into contact allowing circularization of the padlock oligonucleotide by ligation (e.g., ligation using any of the methods described herein). The ligation product can be referred to as the "circularized padlock oligonucleotide." After circularization of the padlock oligonucleotide, rolling circle amplification can be used to amplify the circularized padlock oligonucleotide. In some embodiments using a padlock oligonucleotide, the method does not include contacting the biological sample with an array comprising capture probes.

In some embodiments, a padlock oligonucleotide includes a first sequence that is substantially complementary to a portion of the first oligonucleotide, a backbone sequence comprising a barcode, and a second sequence that is substantially complementary to portion of the second oligonucleotide.

In some embodiments, a first sequence of a padlock oligonucleotide includes a sequence that is substantially complementary to a portion of the first oligonucleotide. In some embodiments, the first sequence of a padlock oligonucleotide is substantially complementary to a first barcode sequence of the first oligonucleotide. In some embodiments, the first sequence is at least 70% identical (e.g., at least 75% identical, at least 80% identical, at least 85% identical, at least 90% identical, at least 95% identical, or at least 99% identical) to the first portion of the first oligonucleotide. It is understood that the first sequence of a padlock oligonucleotide can include a sequence that is substantially complementary to a portion of the second oligonucleotide that is bound to the second analyte-binding moiety.

In some embodiments, a backbone sequence of a padlock oligonucleotide includes a sequence that is substantially complementary to an amplification primer. The amplification primer can be a primer used in a rolling circle amplification reaction (RCA) of the ligated padlock oligonucleotide hybridized to the analyte or analyte derived molecules. RCA, or rolling circle amplification, is well known in the art and includes a process by which circularized nucleic acid molecules are amplified with a DNA polymerase with strand displacement capabilities (and other necessary reagents for amplification to occur), thereby creating multiple concatenated copies of the circularized nucleic acid molecules.

In some embodiments, the backbone sequence includes a functional sequence. In some embodiments the backbone sequence includes a barcode sequence (e.g., any of the exemplary barcode sequences described herein). In some embodiments, the barcode sequence includes a sequence that is substantially complementary to an amplification primer.

In some embodiments, a second sequence of a padlock oligonucleotide includes a sequence that is substantially complementary to a portion of the second oligonucleotide. In some embodiments, the second sequence is at least 70% identical (e.g., at least 75% identical, at least 80% identical, at least 85% identical, at least 90% identical, at least 95% identical, or at least 99% identical) to the portion of the second oligonucleotide.

In some embodiments, the method includes washing the biological sample after the padlock oligonucleotide is hybridized to the first portion of the first oligonucleotide and the second portion of the second oligonucleotide. The washing step removes padlock oligonucleotides not bound to the first oligonucleotide and/or the second oligonucleotide. In some embodiments, the method includes two or more washing steps, where each step can include different wash reagents and applied to the biological samples for one or more different periods of time.

In some embodiments, the ligation step includes ligating the second sequence to the first sequence of the padlock oligonucleotide using enzymatic or chemical ligation. In some embodiments where the ligation is enzymatic, the ligase is selected from a T4 RNA ligase (Rnl2), a SplintR ligase, a single stranded DNA ligase, or a T4 DNA ligase. In some embodiments, the ligase is a T4 RNA ligase (Rnl2) ligase. In some embodiments, the ligase is a pre-activated T4 DNA ligase as described herein. A non-limiting example describing methods of generating and using pre-activated T4 DNA include U.S. Pat. No. 8,790,873, the entire contents of which are herein incorporated by reference.

In some aspects, this disclosure features methods of determining abundance of an interaction between a first analyte and a second analyte in a biological sample using analyte-binding moieties, a padlock oligonucleotide, and amplification of the padlock oligonucleotide. In a non-limiting example, the method includes an amplifying step where one or more amplification primers are hybridized to the circularized padlock oligonucleotide and the circularized padlock oligonucleotide is amplified using a polymerase, thereby creating an amplified circularized padlock oligonucleotide. In some cases, "amplified circularized padlock oligonucleotide" can be referred to as "amplified padlock oligonucleotide." The amplification product(s) (e.g., the amplified circularized padlock oligonucleotide) can be detected by determining (i) all or a part of the sequence of the amplified circularized padlock oligonucleotide and using the determined sequence of the padlock oligonucleotide to identify the location of the analyte in the biological sample.

As used herein, rolling circle amplification (RCA) refers to a polymerization reaction carried out using a single-stranded circular DNA (e.g., a circularized padlock oligonucleotide) as a template and an amplification primer that is substantially complementary to the single-stranded circular DNA (e.g., the circularized padlock oligonucleotide) to synthesize multiple continuous single-stranded copies of the template DNA (e.g., the circularized padlock oligonucleotide). In some embodiments, RCA includes hybridizing one or more amplification primers to the circularized padlock oligonucleotide and amplifying the circularized padlock oligonucleotide using a DNA polymerase with strand displacement activity, for example Phi29 DNA polymerase. In some embodiments, a first RCA reaction includes a first padlock oligonucleotide and a first amplification primer (or plurality of first amplification primers). A first RCA reaction can include the first padlock oligonucleotide hybridizing to a first analyte or first analyte derived molecule.

In some embodiments, an RCA reaction is carried out using a DNA polymerase and a dNTP mix including uracil, adenine, guanine and cytosine. In such cases, the uracils are incorporated into the amplified padlock oligonucleotide. In some embodiments, an RCA reaction is carried out using a DNA polymerase and a dNTP mix including uracil, adenine, guanine, cytosine and thymine. In such cases, uracils and thymines are both incorporated into the amplified padlock oligonucleotide. In some embodiments, the polymerase has strand displacement activity. A non-limiting example of a polymerase that includes strand displacement activity is a Phi29 DNA polymerase.

In some embodiments, an amplification primer includes a sequence that is substantially complementary to a sequence on the padlock oligonucleotide. In some embodiments, the amplification primer includes a sequence that is substantially complementary to one or more of the first sequence of the padlock oligonucleotide, the backbone sequence, or the second sequence of the padlock oligonucleotide. For example, the amplification primer can be substantially complementary to the backbone sequence. In some embodiments, the amplification primer includes a sequence that is substantially complementary to two or more of the first sequence, the backbone sequence, or the second sequence of the padlock oligonucleotide and an additional portion of the analyte or analyte derived molecule. By substantially complementary, it is meant that the amplification primer is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a sequence in the circularized padlock oligonucleotide.

(k) Methods for Determining Abundance without Capture on an Array

Also provided herein are methods of determining abundance of an interaction between a first analyte and a second analyte in a biological sample where the biological sample is not contacted with a substrate comprising a plurality of capture probes. In such cases, a first oligonucleotide bound to a first analyte-binding moiety is hybridized to a second oligonucleotide bound to a second analyte-binding moiety, thereby producing hybridized sequences. The hybridized product (e.g., the hybridized sequences) can be extended, and the extended product can be amplified. To determine the abundance, the sequence of (i) the extended hybridized product or (ii) amplified hybridized product is determined and used to identify the abundance of an interaction between a first analyte and/or a second analyte in the biological sample. In a second non-limiting example, the method includes: attaching a first analyte-binding moiety to the first analyte, wherein the first analyte-binding moiety is bound to a first oligonucleotide, wherein the first oligonucleotide includes: (i) a first barcode; and (ii) a first bridge sequence; attaching a second analyte-binding moiety to the second analyte, wherein the second analyte-binding moiety is bound to a second oligonucleotide; wherein the second oligonucleotide includes: (i) a second barcode; and (ii) a second bridge sequence; hybridizing the first bridge sequence to the second bridge sequence; extending (i) the first oligonucleotide using the second oligonucleotide as a template and (ii) extending the second oligonucleotide using the first oligonucleotide as a template; and (e) determining (i) all or a part of the sequence of the first barcode or a complement thereof, and/or (ii) all or a part of the sequence of the second barcode or a complement thereof, and using the determined sequence of (i) and/or (ii) to identify the abundance of the first analyte and/or the second analyte in the biological sample.

(l) Methods of Determining a Location of a Host Analyte-Pathogen-Derived Nucleic Acid Interaction Also provided herein is a method of determining a location of a host analyte-pathogen-derived analyte interaction in a biological sample where the pathogen-derived analyte includes a pathogen-derived nucleic acid analyte. In some cases, the method uses proximity ligation between a first antigen binding moiety that binds to a host analyte and a second oligonucleotide that binds to a pathogen-derived nucleic acid analyte (e.g., viral nucleic acid analyte) to determine the location of a host analyte-pathogen-derived nucleic acid analyte interaction in the biological sample. When the host analyte and the nucleic acid analyte are within about 400 nm of each other (e.g., about 300 nm, about 200 nm, about 150 nm, about 100 nm, about 50 nm, about 25 nm, about 10 nm, or about 5 nm) from each other in the biological sample proximity ligation results in a ligation product. The ligation product is an indication of a host analyte-pathogen-derived nucleic acid analyte interaction in the particular location in the biological sample.

In some embodiments, provided herein are methods for determining a location of a host analyte-pathogen-derived nucleic acid analyte interaction where the pathogen-derived nucleic acid analyte is a viral nucleic acid, a bacterial nucleic acid, a fungal nucleic acid, a protozoan nucleic acid, or a worm nucleic acid. Non-limiting examples of pathogens from which nucleic acid can be derived is described in Janeway et al. (*Immunobiology: The Immune System in Health and Disease,* 5th Ed. Editor (2001), which is herein incorporated by reference in its entirety. In some embodiments, provided herein are methods for determining a location of a host analyte-pathogen-derived nucleic acid analyte where the pathogen derived nucleic acid analyte is a viral nucleic acid. In some embodiments, the pathogen derived nucleic acid analyte is a bacterial nucleic acid. The pathogen-derived nucleic acid can be a fungal nucleic acid. In another example, the pathogen derived nucleic acid analyte can include a protozoan nucleic acid. In yet another example, the pathogen derived nucleic acid analyte can include a fungal nucleic acid.

In some embodiments, the first analyte-binding moiety and/or second analyte-binding moiety hybridize to a host analyte that binds to a pathogen-derived nucleic acid analyte (e.g., viral nucleic acid analyte). The initial response of a host cell to an invading pathogen is clearance of the non-self components, which can include viral nucleic acid analytes or nucleic acid analytes from other microbes. Viral nucleic acids can include viral genomes and viral replication products. Host cells can detect an invading pathogen by recognizing 'non-self' components through various means including, without limitation, receptors such as pattern recognition receptors. Pattern recognition receptors bind to pathogen-derived nucleic acid and can distinguish the pathogen-derived nucleic acid (e.g., viral genomes and/or viral replication products) from host-derived nucleic acid. Following binding, pattern recognition receptors can then target the pathogen-derived nucleic acid for degradation or activate antiviral signaling cascades. Non-limiting examples of receptors capable of binding to pathogen-derived nucleic acid (e.g., viral genomes and/or viral replication products) include RIG-I like receptors (RLRs) that recognize viral RNA, vDNA receptors such as cGAS, and NOD-like receptors, as described in Sparrer and Gack 2015 (*Curr. Opin. Microbiol.*, 26:1-9 (2015)), which is herein incorporated by reference in its entirety.

In some embodiments, the first analyte-binding moiety and/or second analyte-binding moiety hybridize to a host analyte that interacts with a pathogen-derived nucleic acid analyte (e.g., viral nucleic acid analyte). Other non-limiting examples of host analytes that can interact with a viral nucleic acid analyte include the host analytes described in Section VI(a)(i) (e.g., host analytes include cellular machinery, cell surface moieties, cell motor proteins, nuclear pore proteins, transcriptional and translational machinery).

Provided herein is a method of determining a location of a host analyte-viral analyte interaction in a biological sample including: (a) hybridizing an analyte-binding moiety to a first analyte in the biological sample, wherein the first analyte-binding moiety is bound to a first oligonucleotide, wherein the first oligonucleotide includes: (i) a first barcode; and (ii) a first bridge sequence; (b) hybridizing a second oligonucleotide to a viral nucleic acid analyte in the biological sample, wherein the second oligonucleotide includes: (i) a capture probe capture domain sequence; (ii) a detection sequence that is substantially complementary to the viral nucleic acid analyte; (iii) a second barcode; and (iv) a second bridge sequence; (c) contacting the biological sample with a third oligonucleotide; (d) hybridizing the third oligonucleotide to the first bridge and to the second bridge sequence; (e) ligating the first oligonucleotide and the second oligonucleotide, thereby generating a ligation product; (f) contacting the biological sample with a substrate, wherein a capture probe is affixed to the substrate, wherein the capture probe includes a spatial barcode and the capture domain; and (g) allowing the capture probe capture domain sequence to bind to the capture domain. In some embodiments, the method includes a wash step. The wash step can occur between step (b) and step (c). In some embodiments, the method also includes a determining step where (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the first analyte and the second analyte in the biological sample. In some embodiments, the second oligonucleotide does not include a second barcode. For example, the second oligonucleotide includes a capture probe capture domain sequence, a detection sequence and a second bridge sequence.

Also provided herein is a method where determining the location of a host analyte-viral analyte interaction in a biological sample includes a capture probe capture domain sequence on the first oligonucleotide. For example, the method of determining a location of a host analyte-viral analyte interaction in a biological sample includes: (a) hybridizing an analyte-binding moiety to a first analyte in the biological sample, wherein the first analyte-binding moiety is bound to a first oligonucleotide, wherein the first oligonucleotide includes: (i) a capture probe capture domain sequence (ii) a first barcode; and (ii) a first bridge sequence; (b) hybridizing a second oligonucleotide to a viral nucleic acid analyte in the biological sample, wherein the second oligonucleotide includes: (i) a detection sequence that is substantially complementary to the viral nucleic acid analyte; (ii) a second barcode; and (iii) a second bridge sequence; (c) contacting the biological sample with a third oligonucleotide; (d) hybridizing the third oligonucleotide to the first bridge sequence of the first oligonucleotide and the second bridge sequence of the second oligonucleotide; (e) ligating the first oligonucleotide and the second oligonucleotide, thereby generating a ligation product; (f) contacting the biological sample with a substrate, wherein a capture probe is affixed to the substrate, wherein the capture probe includes a spatial barcode and the capture domain; and (g) allowing the capture probe capture domain sequence to bind to the capture domain. In some embodiments, the method includes a wash step. The wash step can occur between step (b) and step (c). In some embodiments, the method also includes a determining step where (i) all or a part of the sequence of the ligation product bound to the capture domain, or a complement thereof, and (ii) all or a part of the sequence of the spatial barcode, or a complement thereof, and using the determined sequence of (i) and (ii) to identify the location of the first analyte and the second analyte in the biological sample. In some embodiments, the second oligonucleotide does not include a second barcode. For example, the second oligonucleotide includes a detection sequence and a second bridge sequence.

In some embodiments where the method includes determining a location of a host analyte-viral nucleic acid analyte interaction, the analyte-binding moiety is a protein. In some cases, the protein is an antibody. Non-limiting examples of an antibody is a monoclonal antibody, recombinant antibody, synthetic antibody, a single domain antibody, a single-chain variable fragment (scFv), and or an antigen-binding fragment (Fab). In some embodiments, the analyte-binding moiety is an aptamer. The aptamer can be a DNA aptamer or a RNA aptamer.

In some embodiments, the analyte-binding moiety is associated with the first oligonucleotide via a linker. In some embodiments, the first linker is a cleavable linker. Non-limiting examples of cleavable linkers used to associate the first oligonucleotide with the analyte-binding moiety include a photocleavable linker, UV-cleavable linker, or an enzyme-cleavable linker. In some embodiments, the first cleavable linker is an enzyme cleavable linker.

(i) First Oligonucleotide

In some embodiments where the method includes determining a location of a host analyte-viral nucleic acid analyte interaction, the first oligonucleotide is as described in Section VI(b). Additionally, the first oligonucleotide bound to the analyte-binding moiety includes a free 3' end. The first oligonucleotide includes from 5' to 3': a first barcode and a first bridge sequence. In some embodiments, the first oligonucleotide further includes a functional sequence. The functional sequence can be a primer sequence. In some embodiments, the first oligonucleotide includes from 5' to 3': a primer sequence, a first barcode, and a first bridge sequence. In some embodiments, the first oligonucleotide includes from 5' to 3': a functional sequence and a first barcode.

(ii) Second Oligonucleotide

In some embodiments where the method includes determining a location of a host analyte-pathogen-derived nucleic acid analyte interaction, the second oligonucleotide, the second oligonucleotide that hybridizes to a pathogen-derived nucleic acid analyte in the biological sample includes a sequence of about 20 nucleotides to about 80 nucleotides (e.g., about 25 nucleotides to about 80 nucleotides, about 30 nucleotides to about 80 nucleotides, about 35 nucleotides to about 80 nucleotides, about 40 nucleotides to about 80 nucleotides, about 45 nucleotides to about 80 nucleotides, about 50 nucleotides to about 80 nucleotides, about 55 nucleotides to about 80 nucleotides, about 60 nucleotides to about 80 nucleotides, about 65 nucleotides to about 80 nucleotides, about 70 nucleotides to about 80 nucleotides, about 75 nucleotides to about 80 nucleotides, about 25 nucleotides to about 75 nucleotides, about 30 nucleotides to about 75 nucleotides, about 35 nucleotides to about 75 nucleotides, about 40 nucleotides to about 75 nucleotides, about 45 nucleotides to about 75 nucleotides, about 50 nucleotides to about 75 nucleotides, about 55 nucleotides to about 75 nucleotides, about 60 nucleotides to about 75 nucleotides, about 65 nucleotides to about 75 nucleotides, about 30 nucleotides to about 70 nucleotides, about 35 nucleotides to about 70 nucleotides, about 40 nucleotides to about 70 nucleotides, about 45 nucleotides to about 70 nucleotides, about 50 nucleotides to about 70 nucleotides, about 55 nucleotides to about 70 nucleotides, about 60 nucleotides to about 70 nucleotides, about 65 nucleotides to about 70 nucleotides, about 35 nucleotides to about 65 nucleotides, about 40 nucleotides to about 70 nucleotides, about 45 nucleotides to about 65 nucleotides, about 50 nucleotides to about 65 nucleotides, about 55 nucleotides to about 65 nucleotides, about 60 nucleotides to about 65 nucleotides, about 40 nucleotides to about 60 nucleotides, about 45 nucleotides to about 60 nucleotides, about 50 nucleotides to about 60 nucleotides, about 55 nucleotides to about 60 nucleotides, about 45 nucleotides to about 55 nucleotides, or about 50 nucleotides to about 55 nucleotides). In some embodiments, the second oligonucleotide can be a single strand or doubled stranded nucleic acid sequence that binds to a viral nucleic acid. In some embodiments, the second oligonucleotide is not bound to an analyte-binding moiety. In such cases, the second oligonucleotide includes a free 5' end and a free 3' end. The 5' end can include a phosphorylated nucleotide at the 5' end. The 3' end can include a free hydroxyl group at the free 3' end.

In some embodiments, the second oligonucleotide includes from 3' to 5': a capture probe capture domain sequence, a detection sequence, a second barcode, and a second bridge sequence. In some embodiments, second oligonucleotide includes from 3' to 5': a detection sequence, a second barcode, and a second bridge sequence. In some embodiments, the second oligonucleotide includes from 5' to 3': a capture probe capture domain sequence, a detection sequence, a second barcode and a second bridge sequence. In some embodiments, the second oligonucleotide includes from 5' to 3': a detection sequence, a second barcode, and a second bridge sequence. In some embodiments, the second oligonucleotide includes from 3' to 5': a capture probe capture domain sequence, a detection sequence, and a second bridge sequence. In some embodiments, the second oligonucleotide includes from 3' to 5': a detection sequence and a second bridge sequence. In some embodiments, the second oligonucleotide includes from 5' to 3': a capture probe capture domain sequence, a detection sequence, and a second bridge sequence. In some embodiments, the second oligonucleotide includes from 5' to 3': a detection sequence and a second bridge sequence.

The second oligonucleotide can include a detection sequence where the detection sequence detects a pathogen-derived nucleic acid (e.g., a viral genomes and/or a viral replication product). In some embodiments, the second oligonucleotide includes a detection sequence that is substantially complementary to a pathogen-derived nucleic acid (e.g., a viral genomes and/or a viral replication product). By substantially complementary, it is meant that the detection sequence is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a sequence in an analyte.

The detection sequence of the second oligonucleotide includes a sequence of about 10 nucleotides to about 40 nucleotides (e.g., about 15 nucleotides to about 40 nucleotides, about 15 nucleotides to about 40 nucleotides, about 20 nucleotides to about 40 nucleotides, about 25 nucleotides to about 40 nucleotides, about 30 nucleotides to about 40 nucleotides, about 35 nucleotides to about 40 nucleotides, about 10 nucleotides to about 35 nucleotides, about 15 nucleotides to about 35 nucleotides, about 20 nucleotides to about 35 nucleotides, about 25 nucleotides to about 35 nucleotides, about 30 nucleotides to about 35 nucleotides, about 10 nucleotides to about 30 nucleotides, about 15 nucleotides to about 30 nucleotides, about 20 nucleotides to about 30 nucleotides, about 25 nucleotides to about 30 nucleotides, about 10 nucleotides to about 25 nucleotides, about 15 nucleotides to about 25 nucleotides, about 20 nucleotides to about 25 nucleotides, about 10 nucleotides to about 20 nucleotides, about 15 nucleotides to about 20 nucleotides, or about 10 nucleotides to about 15 nucleotides).

In some embodiments, the second oligonucleotide includes a cleavable domain. The cleavage domain is a second cleavable linker. Non-limiting examples of second cleavable linkers include photocleavable linkers, UV-cleavable linkers, or enzyme-cleavable linkers. For example, the second cleavable linker is an enzyme cleavable linker.

In some embodiments where the method includes determining a location of a host analyte-pathogen-derived nucleic acid (e.g., viral nucleic acid) analyte interaction, the first oligonucleotide bound to the analyte-binding moiety includes a first barcode and the second oligonucleotide that hybridizes to a pathogen-derived nucleic acid analyte (e.g., viral nucleic acid) includes a second barcode where the first and second barcodes are different. The first barcode on the first oligonucleotide can be used to identify the first analyte-binding moiety to which it is bound. The first barcode can be any of the exemplary barcodes described herein. The second barcode can be used to identify the second oligonucleotide, including the particular detection sequence included in the second oligonucleotide. In some embodiments, the detection sequence is used as a barcode to identify the second oligonucleotide. In such cases, the second oligonucleotide includes a capture probe capture domain sequence, a detection sequence, and a second bridge sequence or a detection sequence and a second bridge sequence.

(iii) First Analyte and Pathogen-Derived Nucleic Acid Analyte

In some embodiments where the method includes determining a location of a host analyte-pathogen-derived nucleic acid analyte interaction, the first analyte (e.g., host analyte) and the nucleic acid analyte interact with each other in the biological sample. In some embodiments, the first host analyte that interacts with the nucleic acid analyte is selected from the group consisting of host analytes including: lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, extracellular and intracellular proteins, antibodies, and antigen binding fragments. For example, a host protein binds to a viral nucleic acid and is detectable using the methods described herein where an analyte-binding moiety binds to the host protein and a second oligonucleotide binds to the viral nucleic acid. Proximity ligation ligates the first oligonucleotide bound to the analyte-binding moiety to the second oligonucleotide thereby producing a ligation product that can bind to a capture probe on a substrate.

In some embodiments where the method includes determining a location of a host analyte-pathogen-derived nucleic acid analyte interaction, the first analyte is a host analyte (e.g., non-limiting examples of host analytes as described in Section VI(a)(i) and elsewhere herein and the pathogen-derived nucleic acid analyte is a viral nucleic acid sequence). Nucleic acids found in viruses, and therefore found in host cells invaded by the virus, include viral genome and viral replication products. Non-limiting examples of nucleic acids found in viruses include linear double-stranded (ds) DNA, circular ds DNA, circular single-stranded (ss) DNA, linear ss DNA, ds DRNA, (+) strand RNA, (−) strand RNA, viral genome on a contiguous nucleic acid molecule, viral genome distributed across two or more nucleic acid molecules, and viral replication products (products of host cell-mediated transcription or reverse transcription of a viral nucleic acid sequence). In some embodiments, the second oligonucleotide hybridizes to any of the viral nucleic acid sequences described herein, including viral genomes and viral replication products. In some embodiments, the second oligonucleotide hybridizes to a viral RNA sequence. In some embodiments, the second oligonucleotide hybridizes to a viral DNA sequence.

(iv) Third Oligonucleotide

In some embodiments where the method includes determining a location of a host analyte-pathogen-derived nucleic acid (e.g., viral nucleic acid) analyte interaction, the method includes a third oligonucleotide that hybridizes to the first bridge sequence on the first oligonucleotide and the second bridge sequence on the second oligonucleotide. In some embodiments where the method includes determining a location of a host analyte-pathogen-derived nucleic acid analyte interaction, the third nucleotide is as described in Section VI(d). A non-limiting example of a third oligonucleotide includes a third oligonucleotide having a sequence from 3' to 5': a sequence that is at least partially complementary to the second bridge sequence and a sequence that is at least partially complementary to the first bridge sequence. Another non-limiting example of a third oligonucleotide includes a third oligonucleotide having a sequence from 5' to 3': a sequence that is at least partially complementary to the second bridge sequence a sequence that is at least partially complementary to the first bridge sequence.

(v) Capture Probe Capture Domain Sequence

In some embodiments where the method includes determining a location of a host analyte-pathogen-derived nucleic acid analyte interaction, the capture probe capture domain sequences is as described in Section VI(i). For example, the capture probe capture domain sequence includes a sequence that is complementary to the capture domain. In some cases, the ligation product includes the capture probe capture domain sequence or a sequence that is substantially complementary to the capture probe capture domain sequence.

(vi) Ligating, Extending, Releasing and Determining

In some embodiments where the method includes determining a location of a host analyte-pathogen-derived nucleic acid analyte interaction, the ligating step uses enzymatic ligation or chemical ligation to create a ligation product. In some embodiments, the enzymatic ligation utilizes a ligase. For example, a ligase can be a splintR ligase.

In some embodiments, the first oligonucleotide and/or the second oligonucleotide can be extended after binding to the analyte. A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

In some embodiments where the method includes determining a location of a host analyte-pathogen-derived nucleic acid (e.g., viral nucleic acid) analyte interaction, the method includes releasing the ligation product. Where the method includes determining a location of a host analyte-pathogen-derived nucleic acid analyte interaction, the method includes a releasing step where the first oligonucleotide is removed from the first analyte-binding moiety. The releasing step can include contacting the first analyte-binding moiety associated with the first oligonucleotide with an enzyme. As mentioned in Section VI(k), the analyte-binding moiety is associated with the first oligonucleotide via a cleavable linker. Non-limiting cleavable linkers include a photocleavable linker, UV-cleavable linker, or an enzyme-cleavable linker. In some embodiments, the cleavable linker is an enzyme cleavable linker. In such cases, the releasing step includes cleaving the cleavable linker that connects the analyte-binding moiety to the first oligonucleotide thereby releasing the first oligonucleotide. In some cases, the releasing step is performed after generation of the ligation product.

In some embodiments, all or a part of a ligation product (e.g., a full length oligonucleotide) can be amplified before, contemporaneously with, or after the ligation product (e.g., a full length oligonucleotide is contacted with the substrate that includes the capture probes). In some embodiments, after creation of the ligation product, the ligation product (i.e., comprising a first oligonucleotide, a second oligonucleotide, and a third oligonucleotide) can be cleaved from the first analyte-binding moiety. In some embodiments, amplification includes PCR amplification. In some embodiments, amplification is by reverse transcription polymerase chain reaction (RT-PCR). In some embodiments, amplification includes a template switching oligonucleotides (TSOs). In some embodiments, amplification can be isothermal. In some embodiments, amplification is not isothermal.

Following amplification, an amplification product includes (i) all or part of sequence of the ligation product bound to the capture domain, or a complement thereof, and (ii) all or a part of the sequence of the spatial barcode, or a complement thereof. In some embodiments, the determining step includes sequencing. The sequencing can include any of the sequencing technologies described herein, for example sequencing by synthesis, sequence by ligation, sequence by hybridization, etc.

(m) Methods of Determining a Location and Abundance of the Ligation Product on an Array After the ligation product has hybridized or otherwise been associated with a capture probe according to any of the methods described above in connection with the general spatial cell-based analytical methodology, the barcoded constructs that result from hybridization/association are analyzed.

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, the biological sample remains on the substrate during removal (e.g., via denaturation) of a copy of the capture probe (e.g., complement). In some embodiments, analysis of an analyte bound to capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture probe bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; and (d) analyzing the captured biological analyte, thereby spatially detecting the biological analyte of interest; where the biological sample is not removed from the substrate.

In some embodiments, the method further includes subjecting a region of interest in the biological sample to spatial transcriptomic analysis. In some embodiments, one or more of the capture probes includes a capture domain. In some embodiments, one or more of the capture probes comprises a unique molecular identifier (UMI). In some embodiments, one or more of the capture probes comprises a cleavage domain. In some embodiments, the cleavage domain comprises a sequence recognized and cleaved by uracil-DNA glycosylase, apurinic/apyrimidinic (AP) endonuclease (APE1), uracil-specific excision reagent (USER), and/or an endonuclease VIII. In some embodiments, one or more capture probes do not comprise a cleavage domain and is not cleaved from the array.

In some embodiments, a capture probe can be extended (an "extended capture probe," e.g., as described herein). For example, extending a capture probe can include generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA (e.g., cDNA) molecule is generated. In some embodiments, a "full-length" DNA molecule refers to the whole of the captured nucleic acid molecule. However, if a nucleic acid (e.g., RNA) was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Lucigen, Middleton, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Lucigen, Middleton, WI), and SplintR (available from New England Biolabs, Ipswich, MA). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g., by heating to denature a double-stranded molecule).

In some embodiments, the extended capture probe or complement or amplicon thereof is released from the surface of the substrate (e.g., array) by physical means. For example, where the extended capture probe is indirectly immobilized on the array substrate, e.g., via hybridization to a surface probe, it can be sufficient to disrupt the interaction between the extended capture probe and the surface probe. Methods for disrupting the interaction between nucleic acid molecules include denaturing double stranded nucleic acid molecules are known in the art. A straightforward method for releasing the DNA molecules (i.e., of stripping the array of extended probes) is to use a solution that interferes with the hydrogen bonds of the double stranded molecules. In some embodiments, the extended capture probe is released by an applying heated solution, such as water or buffer, of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

In some embodiments, probes complementary to the extended capture probe can be contacted with the substrate. In some embodiments, the biological sample can be in contact with the substrate when the probes are contacted with the substrate. In some embodiments, the biological sample can be removed from the substrate prior to contacting the substrate with probes. In some embodiments, the probes can be labeled with a detectable label (e.g., any of the detectable labels described herein). In some embodiments, probes that do not bind (e.g., hybridize) to an extended capture probe can be washed away. In some embodiments, probes complementary to the extended capture probe can be detected on the substrate (e.g., imaging, any of the detection methods described herein).

In some embodiments, probes complementary to an extended capture probe can be about 4 nucleotides to about 100 nucleotides long. In some embodiments, probes (e.g., detectable probes) complementary to an extended capture probe can be about 10 nucleotides to about 90 nucleotides long. In some embodiments, probes (e.g., detectable probes) complementary to an extended capture probe can be about 20 nucleotides to about 80 nucleotides long. In some embodiments, probes (e.g., detectable probes) complementary to an extended capture probe can be about 30 nucleotides to about 60 nucleotides long. In some embodiments, probes (e.g., detectable probes) complementary to an extended capture probe can be about 40 nucleotides to about 50 nucleotides long. In some embodiments, probes (e.g., detectable probes) complementary to an extended capture probe can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 nucleotides long.

In some embodiments, about 1 to about 100 probes can be contacted to the substrate and bind (e.g., hybridize) to an extended capture probe. In some embodiments, about 1 to about 10 probes can be contacted to the substrate and bind (e.g., hybridize) to an extended capture probe. In some embodiments, about 10 to about 100 probes can be contacted to the substrate and bind (e.g., hybridize) to an extended capture probe. In some embodiments, about 20 to about 90 probes can be contacted to the substrate and bind (e.g., hybridize) to an extended capture probe. In some embodiments, about 30 to about 80 probes (e.g., detectable probes) can be contacted to the substrate and bind (e.g., hybridize) to an extended capture probe. In some embodiments, about 40 to about 70 probes can be contacted to the substrate and bind (e.g., hybridize) to an extended capture probe. In some embodiments, about 50 to about 60 probes can be contacted to the substrate and bind (e.g., hybridize) to an extended capture probe. In some embodiments, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 probes can be contacted to the substrate and bind (e.g., hybridize) to an extended capture probe.

In some embodiments, the probes can be complementary to a single analyte (e.g., a single gene). In some embodiments, the probes can be complementary to one or more analytes (e.g., analytes in a family of genes). In some embodiments, the probes (e.g., detectable probes) can be for a panel of genes associated with a disease (e.g., cancer, Alzheimer's disease, Parkinson's disease).

In some instances, the one or more analytes and capture probe can be amplified or copied, creating a plurality of cDNA molecules. In some embodiments, cDNA can be denatured from the capture probe template and transferred (e.g., to a clean tube) for amplification, and/or library construction. The spatially-barcoded cDNA can be amplified via PCR prior to library construction. The cDNA can then be enzymatically fragmented and size-selected in order to optimize for cDNA amplicon size. P5 and P7 sequences directed to capturing the amplicons on a sequencing flowcell (Illumina sequencing instruments) can be appended to the amplicons, i7, and i5 can be used as sample indexes, and TruSeq Read 2 can be added via End Repair, A-tailing, Adaptor Ligation, and PCR. The cDNA fragments can then be sequenced using paired-end sequencing using TruSeq Read 1 and TruSeq Read 2 as sequencing primer sites. The additional sequences are directed toward Illumina sequencing instruments or sequencing instruments that utilize those sequences; however a skilled artisan will understand that additional or alternative sequences used by other sequencing instruments or technologies are also equally applicable for use in the aforementioned methods.

In some embodiments, where a sample is barcoded directly via hybridization with capture probes or analyte capture agents hybridized, bound, or associated with either the cell surface, or introduced into the cell, as described above, sequencing can be performed on the intact sample.

A wide variety of different sequencing methods can be used to analyze a barcoded analyte (e.g., the one or more analytes). In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based single plex methods, emulsion PCR), and/or isothermal amplification. Non-limiting examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods.

(n) In Situ Detection of a Ligation Product

Also provided herein are methods for amplifying the ligation product produced during (i) the methods of determining a location of at least one analyte in a biological sample and (ii) the methods determining a location of a host analyte-viral analyte interaction in a biological sample. Exemplary ligation products can include a first barcode, a first bridge sequence, a second bridge sequence, a second barcode, and a capture probe capture domain sequence. Amplification of a ligation product increases the copy number of the ligation product, thereby increasing the copy number of the components of the ligation product including the first barcode, the first bridge sequence, the second bridge sequence, the second barcode, and the capture probe capture domain sequence. In some embodiments where the method includes amplifying the ligation product, the amplifying includes rolling circle amplification (RCA).

Also provided herein are methods of detecting the amplified ligation product. Following amplification, the ligation product can be detected using in situ detection by hybridizing a plurality of in situ detection moieties to the increased copy number of ligation product. In some embodiments, the one or more detection moieties includes a nucleic acid that is substantially complementary to the ligation product or a sequence created using RCA. In some embodiments, the one or more detection moieties includes a detection label. In some embodiments, the detection label is selected from a fluorophore, a radioisotope, a chemiluminescent compound, a bioluminescent compound, or a dye where the detection label is used to identify the presence of the ligation product.

In one aspect, provided herein is a method of determining a location of at least one analyte in a biological sample that includes: (a) hybridizing a first analyte-binding moiety to a first analyte in the biological sample, wherein the first analyte-binding moiety is bound to a first oligonucleotide, wherein the first oligonucleotide includes: (i) a first barcode; and (ii) a first bridge sequence; (b) hybridizing a second analyte-binding moiety to a second analyte in the biological sample, wherein the second analyte-binding moiety is bound to a second oligonucleotide; wherein the second oligonucleotide includes: (i) a capture probe capture domain sequence; (ii) a second barcode; and (iii) a second bridge sequence; (c) contacting the biological sample with a third oligonucleotide; (d) hybridizing the third oligonucleotide to the first bridge sequence and to the second bridge sequence; (e) ligating the first oligonucleotide and the second oligonucleotide, thereby generating a ligation product; (f) amplifying the ligation product, where the amplifying includes rolling circle amplification (RCA); and (g) detecting the ligation product in situ by adding one or more detection moieties to the biological sample, thereby determining the location of the first analyte in the biological sample.

In another aspect, provided herein is a method of determining a location of a host analyte-viral analyte interaction in a biological sample that includes: (a) hybridizing an analyte-binding moiety to a first analyte in the biological sample, wherein the first analyte-binding moiety is bound to a first oligonucleotide, wherein the first oligonucleotide includes: (i) a first barcode; and (ii) a first bridge sequence; (b) hybridizing a second oligonucleotide to a viral nucleic acid analyte in the biological sample, wherein the second oligonucleotide includes: (i) a capture probe capture domain sequence; (ii) a detection sequence that is at substantially complementary to the viral nucleic acid analyte; (iii) a second barcode; and (iv) a second bridge sequence; (c) contacting the biological sample with a third oligonucleotide; (d) hybridizing the third oligonucleotide to the first bridge and to the second bridge sequence; (e) ligating the first oligonucleotide and the second oligonucleotide, thereby generating a ligation product; (f) amplifying the ligation product, where the amplifying includes rolling circle amplification (RCA); and (g) detecting the ligation product in situ by adding one or more detection moieties to the biological sample, thereby determining the location of the first analyte in the biological sample.

(o) Blocking Probes

In some embodiments, a capture probe capture domain is blocked prior to being added to a biological sample. In some embodiments, a capture probe capture domain of a third oligonucleotide is blocked prior to adding the third oligonucleotide (e.g., a proximity probe) to a biological sample. In some embodiments, capture probe capture domain is blocked prior to adding the third oligonucleotide (e.g., the proximity probe) to a substrate comprising a plurality of capture probes. In some embodiments, a first bridge sequence and/or a second bridge sequence can be blocked prior to adding to the biological sample. For example, a blocking probe can be used to block the first bridge sequence and/or a second bridge sequence. This prevents the first bridge sequence from prematurely hybridizing to the second bridge sequence. In some cases, premature hybridization can refer to hybridization that occurs prior to the respective analyte binding moieties binding to the target analytes (e.g., the first and second target analytes).

In some embodiments, a blocking probe is used to block or modify the free 3' end of the capture probe capture domain. In some embodiments, a blocking probe can be hybridized to the capture probe capture domain of the third oligonucleotide (e.g., the proximity probe) to mask the free 3' end of the capture probe capture domain. In some embodiments, a blocking probe can be a hairpin probe or partially double stranded probe. In some embodiments, the free 3' end of the capture probe capture domain of the proximity probe can be blocked by chemical modification, e.g., addition of an azidomethyl group as a chemically reversible capping moiety such that the capture probes do not include a free 3' end. Blocking or modifying the capture probe capture domain, particularly at the free 3' end of the capture probe capture domain, prior to contacting proximity probe with the substrate, prevents binding of the proximity probe to capture probe capture domain (e.g., prevents the binding of an poly(A) of a capture probe capture domain to a poly(T) capture domain).

In some embodiments, the blocking probes can be reversibly removed. For example, blocking probes can be applied to block the free 3' end of either or both the capture probe capture domain and/or the capture probes. Blocking interaction between the capture probe capture domain and the capture probe on the substrate can reduce non-specific binding to the capture probes. After the proximity probes are bound to the first and/or second oligonucleotides, the blocking probes can be removed from the 3' end of the capture probe capture domain and/or the capture probe, and the proximity probes can migrate to and become bound by the capture probes on the substrate. In some embodiments, the removal includes denaturing the blocking probe from capture probe capture domain and/or capture probe. In some embodiments, the removal includes removing a chemically reversible capping moiety. In some embodiments, the removal includes digesting the blocking probe with an RNAse (e.g., RNAse H).

In some embodiments, the blocking probes are oligo (dT) blocking probes. In some embodiments, the oligo (dT) blocking probes can have a length of 15-30 nucleotides. In some embodiments, the oligo (dT) blocking probes can have a length of 10-50 nucleotides, e.g., 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 45-50 nucleotides. In some embodiments, the analyte capture agents can be blocked at different temperatures (e.g., 4° C. and 37° C.). In some embodiments, the analyte capture agents can be blocked from binding to the capture probes more effectively at lower temperatures when using shorter blocking probes.

(p) Sequencing

After analytes capture agents from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is barcoded directly via hybridization with capture probes or analyte capture agents hybridized, bound, or associated with either the cell surface, or introduced into the cell, as described above, sequencing can be performed on the intact sample. Alternatively, if the barcoded sample has been separated into fragments, cell groups, or individual cells, as described above, sequencing can be performed on individual fragments, cell groups, or cells. For analytes that have been barcoded via partitioning with beads, as described above, individual analytes (e.g., cells, or cellular contents following lysis of cells) can be extracted from the partitions by breaking the partitions, and then analyzed by sequencing to identify the analytes.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for determining the sequence of genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, sequence by synthesis and Polony sequencing), ligation methods, and microarray methods. Additional examples of sequencing methods that can be used include targeted sequencing, single molecule sequencing, exon sequencing, electron microscopy-based sequencing, panel sequencing, transistor-mediated sequencing, direct sequencing, random shotgun sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), paired-end sequencing, near-term sequencing, exonuclease sequencing, sequencing by ligation, MS-PET sequencing, and any combinations thereof.

(q) Kits

In some embodiments, also provided herein are kits that include one or more reagents to detect one or more analytes described herein. In some instances, the kit includes a substrate including a plurality of capture probes including a spatial barcode and the capture domain. In some instances, the kit includes a first analyte-binding moiety, a second analyte-binding moiety, a third oligonucleotide, a proximity probe, or a padlock oligonucleotide.

Another non-limiting example of a kit used to perform any of the methods described herein includes: (a) an array including a plurality of capture probes; (b) a first analyte-binding moiety and a second analyte-binding moiety, wherein the first analyte-binding moiety is bound to a first oligonucleotide, wherein the first oligonucleotide includes: a first barcode, wherein the second analyte-binding moiety is bound to a second oligonucleotide; wherein the second oligonucleotide includes: (i) a capture probe capture domain sequence; and (ii) a second barcode; (c) a third oligonucleotide, wherein the third nucleotide includes a sequence that is substantially complementary to the first oligonucleotide, and a sequence that is substantially complementary to the second oligonucleotide; (d) a ligase; and (e) instructions for performing the method of any one of the preceding claims.

Another non-limiting example of a kit used to perform any of the methods described herein includes: (a) an array including a plurality of capture probes; (b) a first analyte-binding moiety and a second analyte-binding moiety, wherein the first analyte-binding moiety is bound to a first oligonucleotide, wherein the first oligonucleotide includes: a first barcode, wherein the second analyte-binding moiety is bound to a second oligonucleotide; wherein the second oligonucleotide includes: a second barcode; (c) a third oligonucleotide including (i) a first sequence that is substantially complementary to a portion of the first oligonucleotide, (ii) a second sequence that is substantially complementary to portion of the second oligonucleotide, and (iii) a capture probe capture domain sequence; (d) a ligase; and (e) instructions for performing the method of any one of the preceding claims.

Another non-limiting example of a kit used to perform any of the methods described herein includes: (a) an array including a plurality of capture probes; (b) a first analyte-binding moiety and a second analyte-binding moiety, wherein the first analyte-binding moiety is bound to a first oligonucleotide, wherein the first oligonucleotide includes: (i) a first barcode; and (ii) a first bridge sequence, wherein the second analyte-binding moiety is bound to a second oligonucleotide; wherein the second oligonucleotide includes: (i) a capture probe capture domain sequence; (ii) a second barcode; and (iii) a second bridge sequence, wherein the first bridge sequence is substantially complementary to the second bridge sequence; (c) a plurality of enzymes including a polymerase and a ligase; and (d) instructions for performing the method of any one of the preceding claims. In some embodiments, the first bridge sequence includes one or more uracil nucleotides. In some embodiments, the second bridge sequence includes one or more uracil nucleotides.

EXAMPLES

Figure 7A:
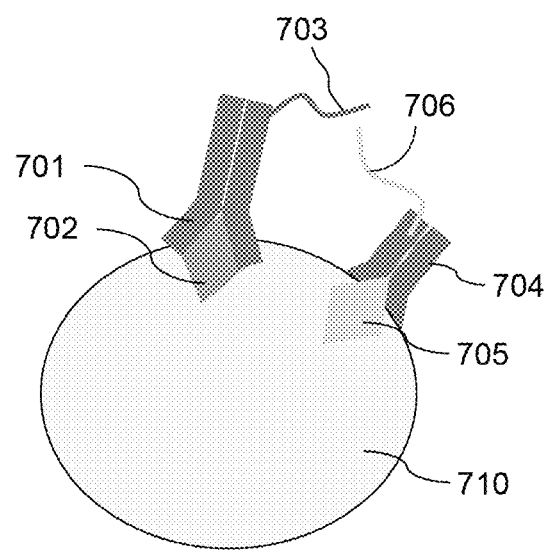
FIGS. 7A-7B are (A) a schematic showing hybridization of analyte-binding moieties to analytes in a biological sample, and (B) a schematic showing an exemplary proximity ligation event.
Figure 7B:
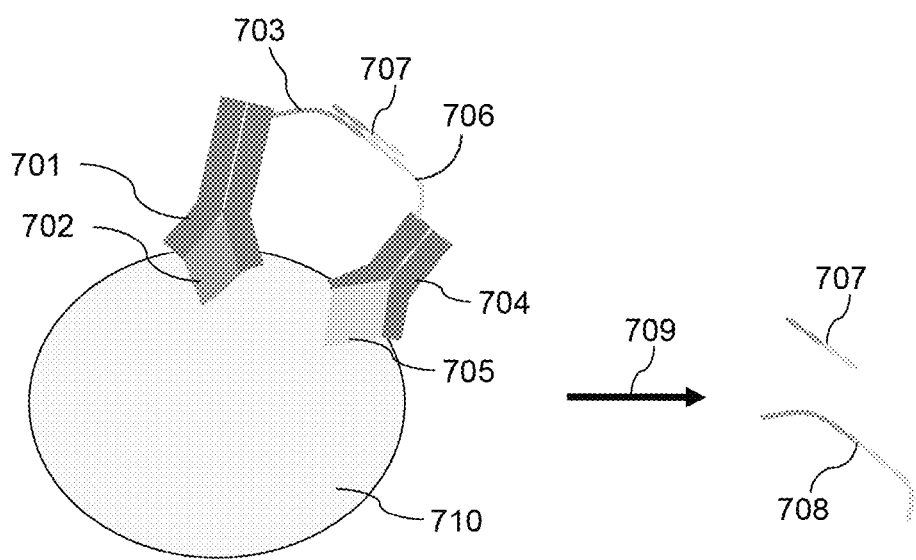

Example 1—Determining a Location of at Least One Analyte in a Biological Sample Using Proximity Ligation FIGS. 7A-B show an exemplary method for determining a location of at least one analyte of interest in a biological sample. In a non-limiting example, the location of at least one analyte of interest can be determined using proximity ligation. A first analyte-binding moiety 701 (FIG. 7A) binds to a first analyte 702 in the biological sample 710. The first analyte-binding moiety 701 is bound to a first oligonucleotide 703. The first oligonucleotide 703 includes a functional sequence; a first barcode; and a first bridge sequence. A second analyte-binding moiety 704 binds to a second analyte 705 in the biological sample 710. The second analyte-binding moiety 704 is bound to a second oligonucleotide 706. The second oligonucleotide 706 includes a capture probe capture domain sequence, a second barcode, and a second bridge sequence.

A third oligonucleotide 707 (FIG. 7B) is added to the biological sample 710 where the third oligonucleotide 707 includes a first sequence that is at least partially complementary to the first bridge sequence and a second sequence that is at least partially complementary to the second bridge sequence. When the first analyte-binding moiety 701 and the second analyte-binding moiety 704 are located in proximity to each other (e.g., when the first analyte and second analyte are within about 400 nm distance, about 300 nm, about 200 nm, about 150 nm, about 100 nm, about 50 nm, about 25 nm, about 10 nm, or about 5 nm) from each other in the biological sample, the third oligonucleotide 707 hybridizes to the first bridge sequence in the first oligonucleotide 703 and the second bridge sequence in the second oligonucleotide 706. Contacting the biological sample with a ligase results in a ligation product 708 that includes the first oligonucleotide 703 ligated to the second oligonucleotide 706. The ligation product is released from both the first analyte-binding moiety and second analyte-binding moiety (as depicted by the arrow and numeral 709).

Figure 8A:
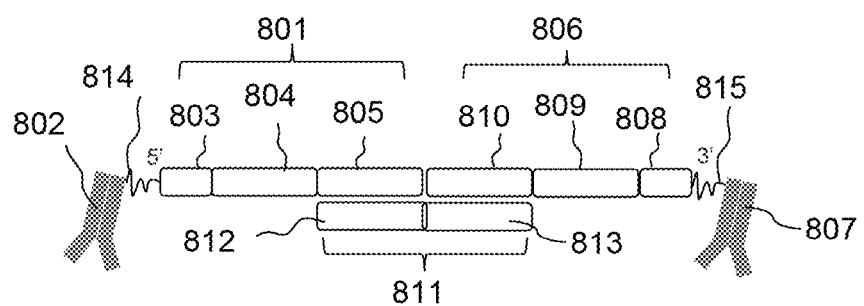
FIGS. 8A-8B are (A) a schematic showing the hybridization and ligation of two oligonucleotides coupled to two analyte-binding moieties, and (B) a schematic showing an exemplary ligation product.
Figure 8B:
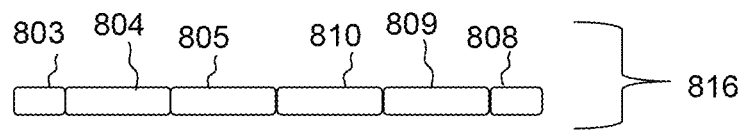

FIGS. 8A-B show exemplary proximity ligation between the first oligonucleotide and the second oligonucleotide via the third oligonucleotide. Here, the first oligonucleotide 801 (FIG. 8A) that is bound to the first analyte-binding moiety 802 includes from 5' to 3' a functional sequence 803, a first barcode 804, and a first bridge sequence 805. The second oligonucleotide 806 that is bound to the second analyte-binding moiety 807 includes from 3' to 5' a capture probe capture domain sequence 808, a second barcode 809, and a second bridge sequence 810. The third oligonucleotide 811 includes a first sequence 812 that is at least partially complementary to the first bridge sequence 805 and a second sequence 813 that is at least partially complementary to the second bridge sequence 810. The first oligonucleotide is bound to the first analyte-binding moiety via a first cleavable linker 814, and the second oligonucleotide is bound to the second analyte-binding moiety via a second cleavable linker 815. The ligation of the first oligonucleotide and the second oligonucleotide produces a ligation product 816 (FIG. 8B) that includes the components of each of the first and second oligonucleotides. Cleavage of the cleavable linkers following the ligation reaction results in a ligation product that can hybridize to a capture probe. The capture probe capture domain sequence of the ligation product can then be captured by the capture probe when the biological sample is contacted with a substrate, as in FIG. 10.

Figure 9A:
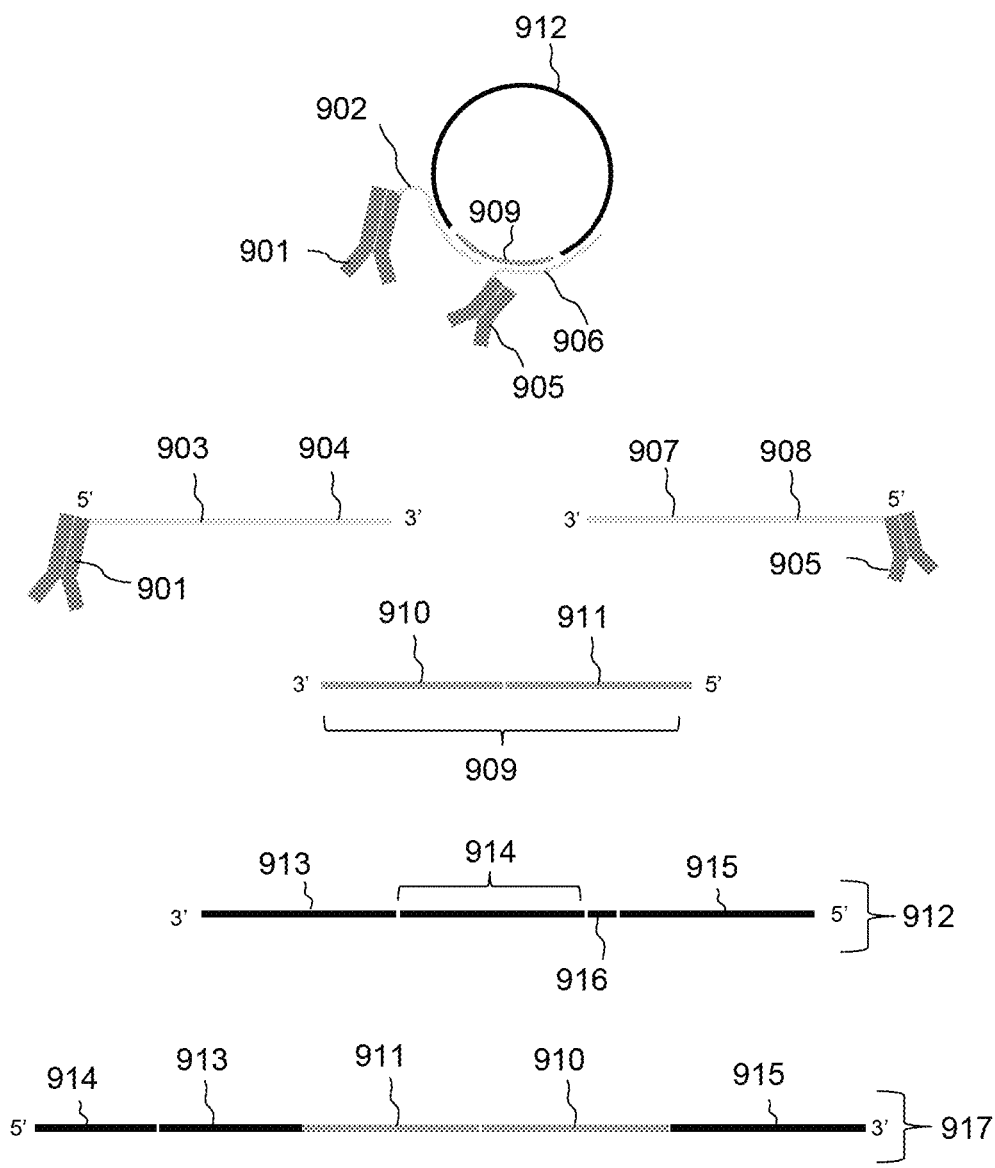
FIGS. 9A-9B are (A) a schematic showing an exemplary proximity ligation event, and (B) a schematic showing an exemplary proximity ligation event.

Example 2—Determining a Location of at Least One Analyte in a Biological Sample Using Proximity Ligation of a Third and Fourth Oligonucleotide FIG. 9A shows an exemplary method for determining a location of at least one analyte in a biological sample using proximity ligation of a third and fourth oligonucleotide. A first analyte-binding moiety 901 is bound to a first oligonucleotide 902. The first oligonucleotide 902 includes a first functional sequence 903 and a first barcode 904. A second analyte-binding moiety 905 is bound to a second oligonucleotide 906. The second oligonucleotide includes a second barcode 907 and a second functional sequence 908.

A third oligonucleotide 909 is added. The third oligonucleotide 909 includes a first sequence 910 that is at least partially complementary to the first oligonucleotide 902 and a second sequence 911 that is at least partially complementary to the second oligonucleotide 906. When the first analyte-binding moiety 901 and the second analyte-binding moiety 905 are located in proximity to each other (e.g., when the first analyte and second analyte are within about 400 nm distance, about 300 nm, about 200 nm, about 150 nm, about 100 nm, about 50 nm, about 25 nm, about 10 nm, or about 5 nm) in the biological sample, the third oligonucleotide 909 hybridizes to the first oligonucleotide 902 and the second oligonucleotide 906.

An additional oligonucleotide 912 is added. The additional oligonucleotide includes a capture probe capture domain sequence 915, a third functional sequence 914, and a priming sequence 913. The functional sequence 914 includes a cleavage site 916. Contacting the biological sample with a ligase results in a ligation product that includes the third oligonucleotide 909 ligated to the additional oligonucleotide 912, thereby creating a circularized oligonucleotide that includes 909 and 912. Addition of an endonuclease that recognizes the cleavage site 916 produces the linear ligation product 917. The capture probe capture domain sequence 915 of the ligation product can then be captured by the capture probe when the biological sample is contacted with a substrate, as in FIG. 10.

Figure 9B:
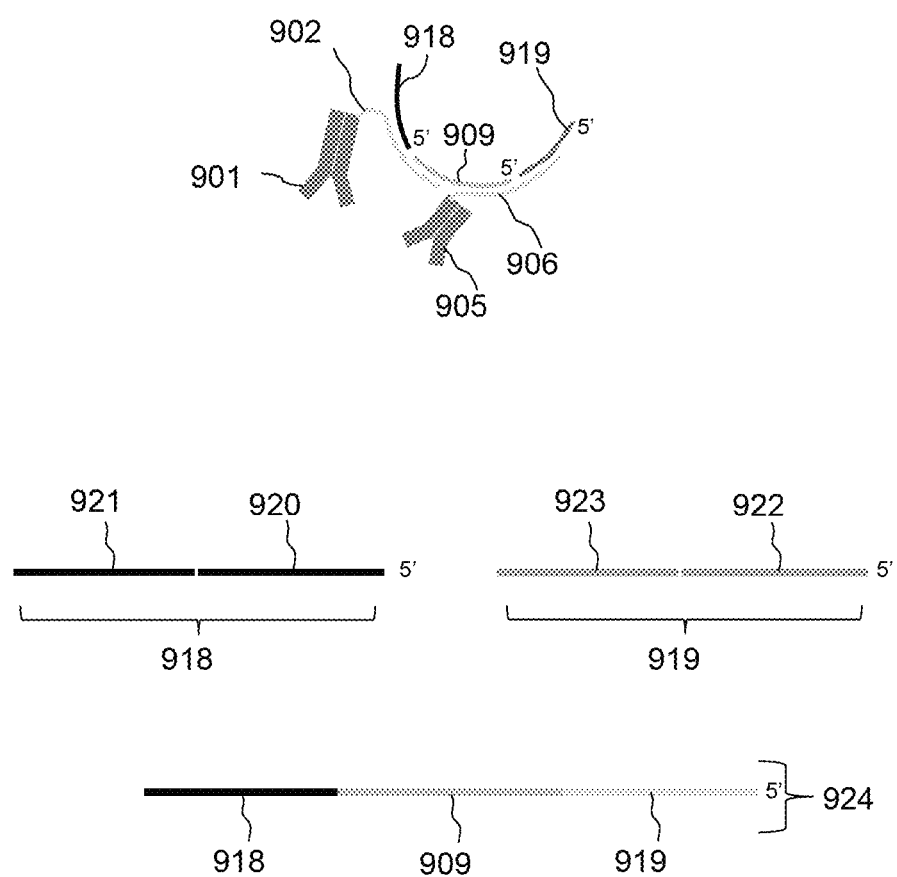

In another non-limiting example, as seen in FIG. 9B, two additional oligonucleotides along with the third oligonucleotide 909 are added. The two additional oligonucleotides include a first additional oligonucleotide 918 and a second additional oligonucleotide 919. The first additional oligonucleotide 918 includes from 5' to 3' a first sequence 920 that is at least partially complementary to the first oligonucleotide 902 and a capture probe capture domain sequence 921. The second additional oligonucleotide 919 includes from 5' to 3' a primer sequence 922 and a second sequence 923 that is at least partially complementary to the second oligonucleotide 906. Contacting the biological sample with a ligase results in a ligation product 924 that includes the first additional oligonucleotide 918, the third oligonucleotide 909, and the second additional oligonucleotide 919 ligated together. The capture probe capture domain sequence 921 of the ligation product can then be captured by the capture probe when the biological sample is contacted with a substrate, as in FIG. 10.

Example 3—Spatial Profiling

Figure 10:
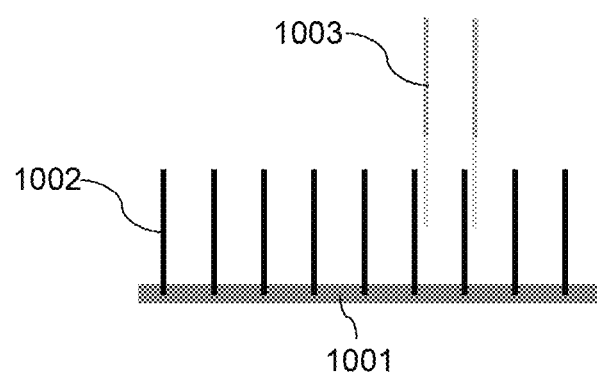
FIG. 10 is a schematic showing the capture of a ligation product on a substrate.

Next, as seen in FIG. 10, the biological sample is contacted with a substrate 1001. The substrate 1001 includes a plurality of capture probes 1002 affixed to the substrate. The capture probes 1002 include a spatial barcode and a capture domain. The capture probe capture domain sequence from the ligation product 1003 (the ligation product depicted as numeral 708 in FIG. 7, 816 in FIG. 8, 917 in FIG. 9, and 925 in FIG. 9) hybridizes to the capture domain thereby coupling the ligation product to the substrate 1001. Finally, the location of the first analyte and the location of the second analyte are resolved by determining (i) all or a part of the sequence of the ligation product 1003 bound to the capture domain, or a complement thereof, and (ii) all or a part of the sequence of the spatial barcode, or a complement thereof, and using the determined sequence of (i) and (ii) to identify the location of the first analyte and the second analyte in the biological sample.

Figure 11A:
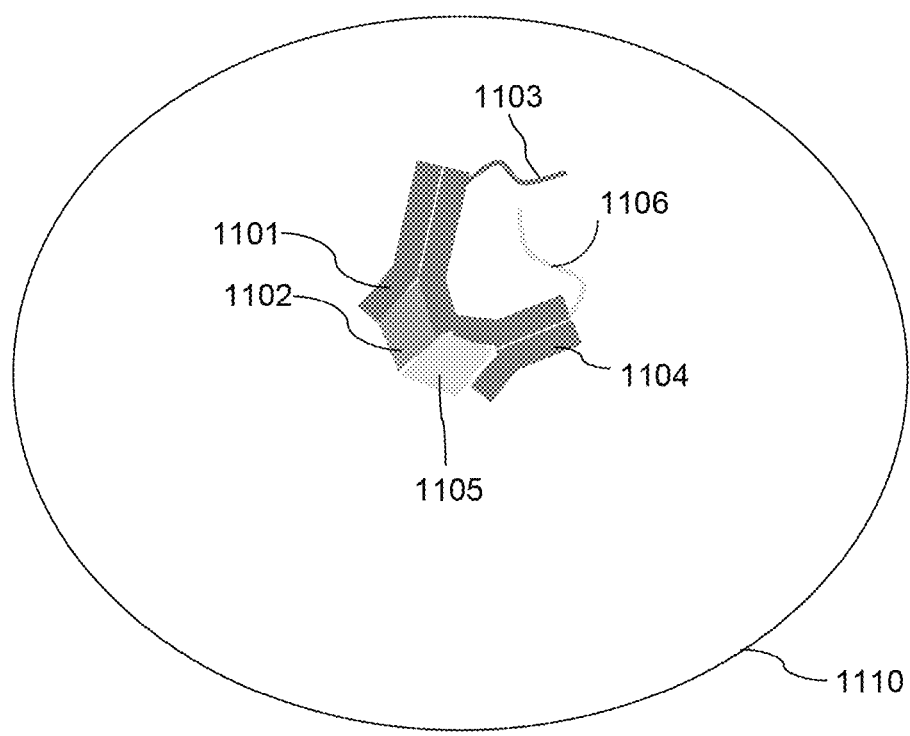
FIGS. 11A-11B are (A) a schematic showing an exemplary hybridization of a first analyte-binding moiety to a host analyte and a second analyte-binding moiety to a viral analyte, and (B) a schematic showing an exemplary ligation event where the second analyte is a viral analyte.
Figure 11B:
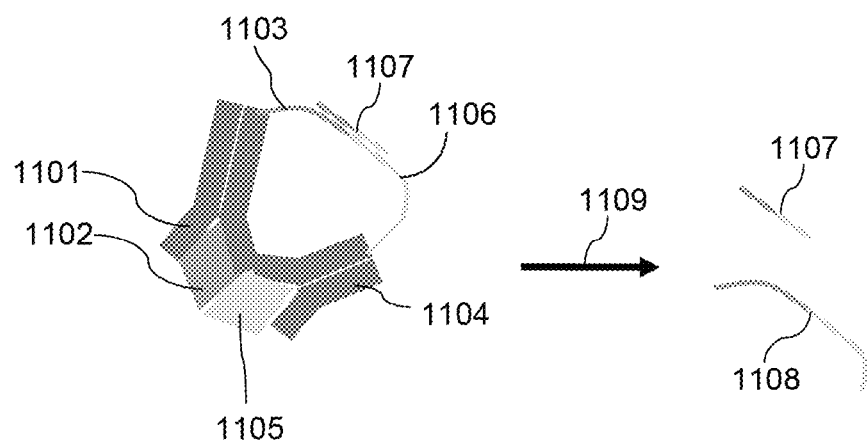

Example 4—Determining a Location of Host Analyte-Viral Analyte Interaction in a Biological Sample Using Proximity Ligation FIGS. 11A-11B show an exemplary method for determining a location of a host analyte-viral analyte interaction in a biological sample. In a non-limiting example, the location of a host analyte-viral analyte interaction can be determined using proximity ligation. A first analyte-binding moiety 1101 binds to a host analyte 1102 on or in a biological sample 1110. The first analyte-binding moiety 1101 is bound to a first oligonucleotide 1103. The first oligonucleotide 1103 includes a functional sequence; a first barcode; and a first bridge sequence. A second analyte-binding moiety 1104 binds to a viral analyte 1105. The second analyte-binding moiety 1104 is bound to a second oligonucleotide 1106. The second oligonucleotide 1106 includes a capture probe capture domain, a second barcode, and a second bridge sequence.

A third oligonucleotide 1107 (FIG. 11B) is added to the biological sample 1110 where the third oligonucleotide 1107 includes a first sequence that is at least partially complementary to the first bridge sequence and a second sequence that is at least partially complementary to the second bridge sequence. When the first analyte-binding moiety 1101 and the second analyte-binding moiety 1104 are located in proximity to each other (e.g., proximity ligation between the first oligonucleotide and the second oligonucleotide via the third oligonucleotide occurs when the first analyte and second analyte are within about 400 nm distance (e.g., about 110 nm, about 200 nm, about 150 nm, about 100 nm, about 50 nm, about 25 nm, about 10 nm, or about 5 nm) from each other in the biological sample), the third oligonucleotide 1107 hybridizes to the first bridge sequence in the first oligonucleotide 1103 and the second bridge sequence in the second oligonucleotide 1106. Contacting the biological sample with a ligase results in a ligation product 1108 that includes the first oligonucleotide 1103 ligated to the second oligonucleotide 1106. The ligation product is released from both the first analyte-binding moiety and second analyte-binding moiety (as depicted by the arrow and numeral 1109), the third oligonucleotide is released from ligation product, and the ligated product is contacted with a substrate, where a capture probe is affixed to the substrate and the capture probe includes a spatial barcode and the capture domain that binds the capture probe capture domain on the ligation product. Once captured on the substrate, the ligation product is processed (e.g., capture probe extension, second strand cDNA synthesis, library preparation and determination of the ligation product sequence). The presence of the sequence of the ligation product (e.g., no proximity ligation results in no ligation product to be sequenced) is used to identify the location of the host analyte-viral analyte interaction in the biological sample.

Figure 12A:
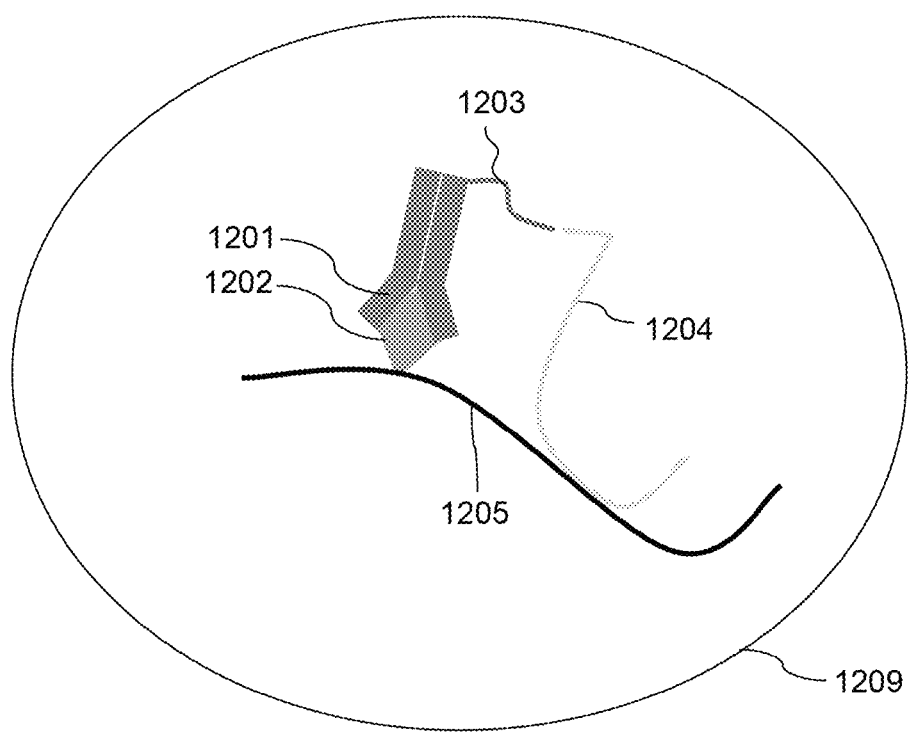
FIGS. 12A-12B are (A) a schematic showing an exemplary hybridization of a first analyte-binding moiety to a host analyte and a second oligonucleotide to a viral nucleic acid analyte, and (B) a schematic showing an exemplary ligation event where one of the analytes is a viral nucleic acid analyte.
Figure 12B:
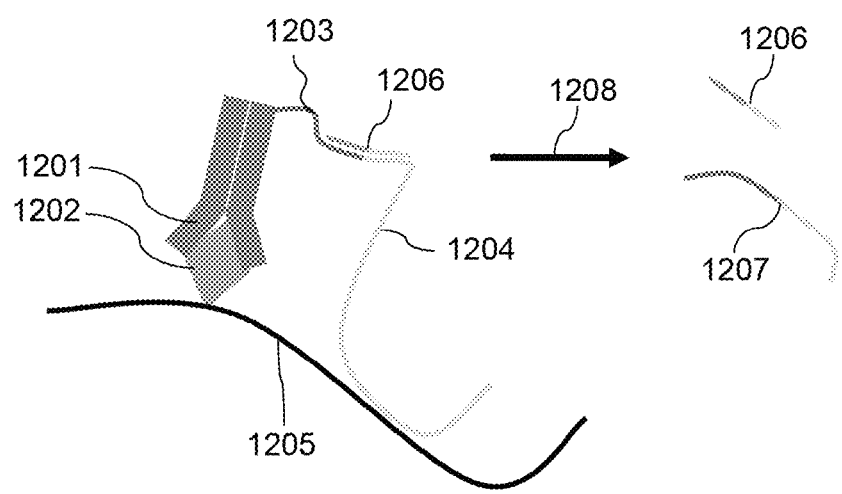

Example 5—Determining a Location of Host Analyte-Viral Nucleic Acid Analyte Interaction in a Biological Sample Using Proximity Ligation FIGS. 12A-12B show an exemplary method for determining a location of a host analyte-viral nucleic acid analyte in a biological sample. In a non-limiting example, the location of a host analyte-viral analyte interaction can be determined using proximity ligation. A first analyte-binding moiety 1201 binds to a host analyte 1202 in or on a biological sample 1209. The first analyte-binding moiety 1201 is bound to a first oligonucleotide 1203. The first oligonucleotide 1203 includes a functional sequence; a first barcode; and a first bridge sequence. A second oligonucleotide 1204 binds to a viral nucleic acid analyte 1205. The second oligonucleotide 1204 includes a capture probe capture domain, a detection sequence that is at substantially complementary to the viral nucleic acid analyte 1205 or a portion thereof, a second barcode, and a second bridge sequence.

A third oligonucleotide 1206 (FIG. 12B) is added to the biological sample 1209 where the third oligonucleotide 1206 includes a first sequence that is at least partially complementary to the first bridge sequence and a second sequence that is at least partially complementary to the second bridge sequence. When the first analyte-binding moiety 1201 and the second oligonucleotide 1204 are located in proximity to each other (e.g., proximity ligation between the first oligonucleotide and the second oligonucleotide via the third oligonucleotide occurs when the first analyte and second analyte are within about 400 nm distance (e.g., about 300 nm, about 200 nm, about 150 nm, about 100 nm, about 50 nm, about 25 nm, about 10 nm, or about 5 nm) from each other in the biological sample), the third oligonucleotide 1206 hybridizes to the first bridge sequence in the first oligonucleotide 1203 and the second bridge sequence in the second oligonucleotide 1204. Contacting the biological sample with a ligase results in a ligation product 1207 that includes the first oligonucleotide 1203 ligated to the second oligonucleotide 1204. The ligation product 1207 is released from the first analyte-binding moiety (as depicted by the arrow and numeral 1208), the third oligonucleotide is released from the ligation product and the ligation product is contacted with a substrate, where a capture probe is affixed to the substrate and the capture probe includes a spatial barcode and the capture domain that binds the capture probe capture domain on the ligation product. Once captured on the substrate, the ligation product is processed (e.g., extension, second strand cDNA synthesis, library preparation and determination of the ligation product sequence). The presence of the sequence of the ligation product identifies the location of the host analyte-viral analyte interaction in the biological sample.

Figure 13:
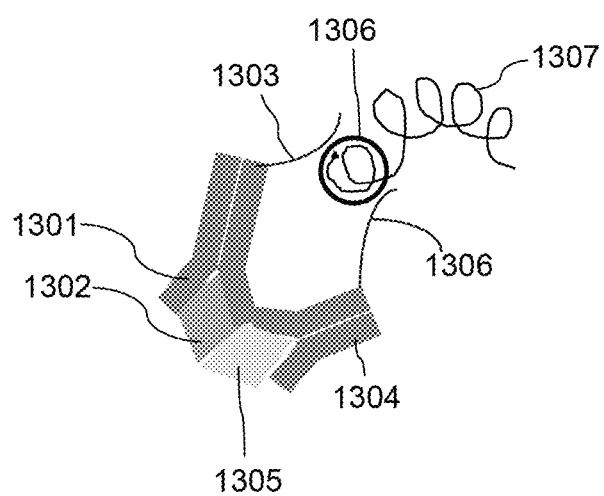
FIG. 13 is a schematic showing proximity ligation combined with rolling circle amplification.

Example 6—Determining a Location of Host Analyte-Viral Nucleic Acid Analyte Interaction in a Biological Sample Using Proximity Ligation and Rolling Circle Amplification FIG. 13 shows an exemplary method for determining a location of a host analyte-viral nucleic acid analyte in a biological sample using proximity ligation and rolling circle amplification. As seen in FIG. 13, a first analyte-binding moiety 1301 binds to a host analyte 1302. The first analyte-binding moiety 1301 is bound to a first oligonucleotide 1303. A second analyte-binding moiety 1304 binds to a viral analyte 1305. The second analyte-binding moiety 1304 is bound to a second oligonucleotide 1306. The second oligonucleotide 1306 includes a capture probe capture domain, a second barcode, and a second bridge sequence.

A third oligonucleotide 1306 is added where the third oligonucleotide 1306 includes a first sequence that is at least partially complementary to the first bridge sequence and a second sequence that is at least partially complementary to the second bridge sequence. When the first analyte-binding moiety 1301 and the second oligonucleotide 1304 are located in proximity to each other (e.g., proximity ligation between the first oligonucleotide and the second oligonucleotide via the third oligonucleotide occurs when the first analyte and second analyte are within about 400 nm distance (e.g., about 300 nm, about 200 nm, about 150 nm, about 100 nm, about 50 nm, about 25 nm, about 10 nm, or about 5 nm) from each other in the biological sample), the third oligonucleotide 1306 hybridizes to the first bridge sequence in the first oligonucleotide 1303 and the second bridge sequence in the second oligonucleotide 1306. The third oligonucleotide 1306 is then amplified using rolling circle amplification (RCA) to produce an amplification product 1307. Finally, one or more in situ detection moieties are added to the biological sample, where a detection moiety includes a sequence that is substantially complementary to at least a portion of the ligation product and includes a fluorophore.

The biological sample is washed to remove detection moieties that did not bind go the ligation product or amplified ligation product. Detection of the fluorophores enables determination of the location of the first analyte in the biological sample.

Figure 14:
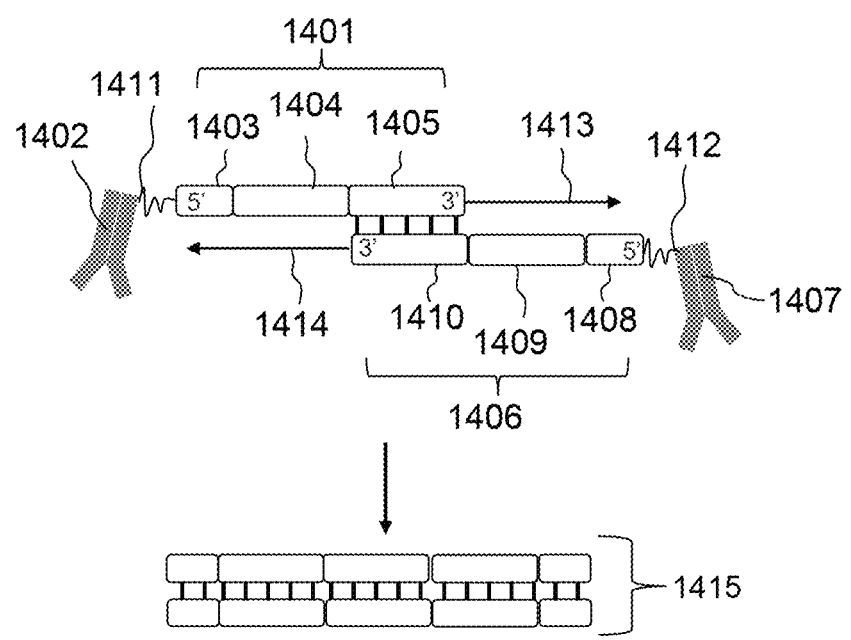
FIG. 14 is schematic diagram showing a first oligonucleotide bound to a first analyte-binding moiety hybridized to a second probe oligonucleotide bound to a second analyte-binding moiety.

Example 7—Determining an Interaction Between a First Analyte and a Second Analyte in a Biological Sample FIG. 14 shows an exemplary method for determining abundance of an interaction between a first analyte and a second analyte in a biological sample. The first oligonucleotide 1401 that is bound to the first analyte-binding moiety 1402 at its 5' end includes from 5' to 3' a functional sequence 1403, a first barcode 1404, and a first bridge sequence 1405. The first bridge sequence includes a sequence that is substantially complementary to the second bridge sequence. The second oligonucleotide 1406 that is bound to the second analyte-binding moiety 1407 at its 5' end includes from 5' to 3' a complement of a capture probe capture domain sequence 1408, a second barcode (or complement thereof) 1409, and a second bridge sequence 1410. The second bridge sequence includes a sequence that is substantially complementary to the first bridge sequence. The first oligonucleotide is bound to the first analyte-binding moiety via a first cleavable linker 1411, and the second oligonucleotide is bound to the second analyte-binding moiety via a second cleavable linker 1412.

After attaching the first analyte-binding moiety to the first analyte and the second analyte-binding moiety to the second analyte, the first bridge sequence 1405 hybridizes to the second bridge sequence 1410 thereby generating a hybridized proximity oligonucleotide. The first oligonucleotide is extended 1413 using the second oligonucleotide as a template, and the second oligonucleotide is extended 1414 using the first oligonucleotide as a template, thereby creating a double stranded hybridized proximity oligonucleotide 1415.

The sequences of the resulting extended first oligonucleotide and extended second oligonucleotides are determined in order to identify the abundance of interaction between the first analyte and the second analyte in the biological sample. Alternatively, the capture probe capture domain sequence of the hybridized proximity oligonucleotide can then be captured by the capture probe, as in FIG. 10, and the sequence of spatial barcode and the hybridized proximity oligonucleotide can be determined in order to determine the location of the interaction.

Figure 15A:
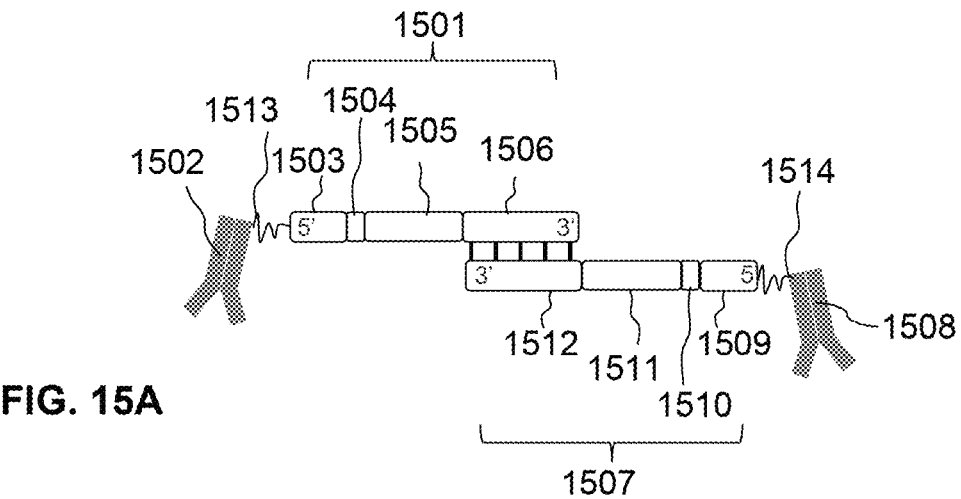
FIGS. 15A-15C are (A) a schematic diagram showing a first oligonucleotide bound to a first analyte-binding moiety hybridized to a second probe oligonucleotide bound to a second analyte-binding moiety where the first and second oligonucleotides include one or more uracil nucleotides, (B)

Example 8—Determining a Location of an Interaction Between a First Analyte and a Second Analyte in a Biological Sample FIG. 15A shows an exemplary method for determining abundance of an interaction between a first analyte and a second analyte in a biological sample where the first and second oligonucleotides include one or more uracil nucleotides. The first oligonucleotide 1501 that is bound to the first analyte-binding moiety 1502 includes from 5' to 3' a functional sequence 1503, one or more uracil nucleotides 1504, a first barcode 1505, and a first bridge sequence 1506. The first bridge sequence includes a sequence that is substantially complementary to the second bridge sequence. The second oligonucleotide 1507 that is bound to the second analyte-binding moiety 1508 includes from 5' to 3' a capture probe capture domain sequence 1509 (or a complement thereof), one or more uracil nucleotides 1510, a second barcode 1511, and a second bridge sequence 1512. The second bridge sequence includes a sequence that is substantially complementary to the first bridge sequence. The first oligonucleotide is bound to the first analyte-binding moiety via a first cleavable linker 1513, and the second oligonucleotide is bound to the second analyte-binding moiety via a second cleavable linker 1514.

After attaching the first analyte-binding moiety to the first analyte and the second analyte-binding moiety to the second analyte, the first bridge sequence 1506 hybridizes to the second bridge sequence 1512 thereby creating a hybridized proximity oligonucleotide. The sample is washed to remove any unbound analyte-binding moieties. The first and second oligonucleotides are cleaved off the first and second analyte-binding moieties. The sequence of the resulting hybridized proximity oligonucleotide is determined in order to identify the abundance of interaction between the first analyte and the second analyte in the biological sample. Alternatively, the capture probe capture domain sequence of the hybridized proximity oligonucleotide can then be captured by the capture probe, as in FIG. 10, and the sequence of spatial barcode and the hybridized proximity oligonucleotide can be determined in order to determine the location of the interaction.

Figure 15B:
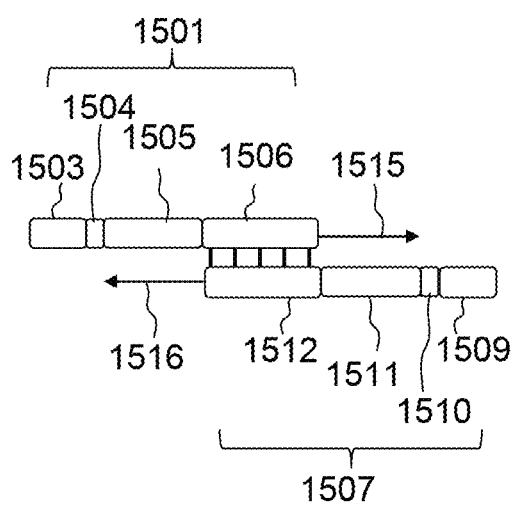

As shown in FIG. 15B, the first oligonucleotide is extended 1515 with a U(−) polymerase using the second oligonucleotide as a template, and the second oligonucleotide is extended 1516 with a U(−) polymerase using the first oligonucleotide as a template, thereby creating a partially double stranded hybridized proximity oligonucleotide. The partially double stranded hybridized proximity oligonucleotide includes a single stranded capture probe capture domain capable of binding to the capture probe on a substrate. The single stranded overhang is a product of the U(−) polymerase not processing through the one or more uracil nucleotides present in the first and second oligonucleotides. The partially double stranded hybridized proximity oligonucleotide is then bound to a capture probe on a substrate and the resulting extended first oligonucleotide and extended second oligonucleotides are determined in order to identify the location and the abundance of interaction between the first analyte and the second analyte in the biological sample.

Figure 15C:
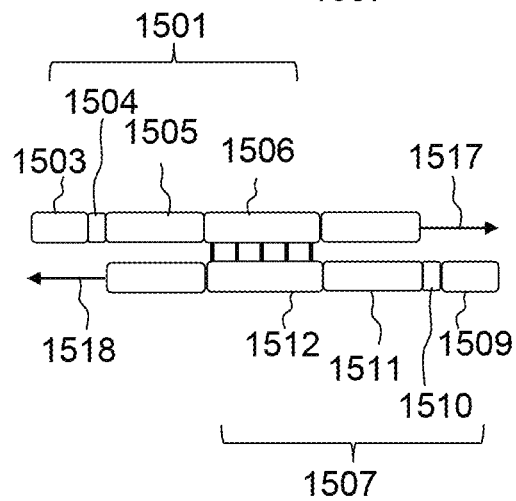

Alternatively, as shown in FIG. 15C, the first oligonucleotide is then extended 1517 with a U(+) polymerase using the second oligonucleotide as a template, and the second oligonucleotide is extended 1518 with a U(+) polymerase using the first oligonucleotide as a template, thereby creating a full length double stranded hybridized proximity oligonucleotide. Here, a Q5U Hot Start High-Fidelity polymerase (i.e., a polymerase) is used, for example, that includes a mutation in the uracil-binding pocket that enables the ability to read and amplify templates containing uracil bases. Extending the hybridized proximity oligonucleotide creates a double-stranded hybridized proximity oligonucleotide where each strand can include a spatial barcode and a capture probe capture domain sequence. Each resulting strand is then captured by hybridizing the capture probe capture domain to a capture domain on a substrate. All or part of the sequence of the hybridized proximity oligonucleotide bound to the capture domain, or a complement thereof is determined. The determined sequence is used to identify the location of the interaction between the first analyte and the second analyte in the biological sample.

Example 9—Determining a Location of an Interaction Between a First Analyte and a Second Analyte Using a Proximity Probe FIG. 16 shows an exemplary method for determining abundance of an interaction between a first analyte and a second analyte in a biological sample using a proximity probe. The first oligonucleotide 1601 that is bound to the first analyte-binding moiety 1602 includes from 5' to 3': a first functional sequence 1603 and a first barcode 1604. The second oligonucleotide 1605 that is bound to the second analyte-binding moiety 1606 includes from 3' to 5': a second functional sequence 1607 and a second barcode 1608. The first oligonucleotide is bound to the first analyte-binding moiety via a first cleavable linker 1609, and the second oligonucleotide is bound to the second analyte-binding moiety via a second cleavable linker 1610.

After attaching the first and/or second analyte-binding moieties to the first and second analytes, the sample is washed to remove any unbound analyte-binding moieties. A wash step can be performed using any wash solution disclosed herein. After the washing step to remove any unbound analyte-binding moieties, the biological sample can be contacted with the proximity probe 1611, which is allowed to hybridize to the first oligonucleotide and the second oligonucleotide.

The proximity probe 1611 includes a capture probe capture domain sequence 1612, a first sequence 1613 that is substantially complementary to the first barcode sequence 1604, a second sequence 1614 that is substantially complementary to the second barcode sequence 1608, and a functional sequence 1615.

A second wash step can be performed after hybridizing the proximity probe to the first and second oligonucleotides in order to remove any unbound proximity probes. The proximity probe is then released the proximity probe from the first and second oligonucleotides. The proximity probe is then allowed to hybridize to a capture probe via the interaction between the capture probe capture domain and the capture domain. All or part of the sequence of the proximity probe bound to the capture domain, or a complement thereof is determined. The determined sequence along with the determined sequence of the spatial barcode is used to identify the location of the interaction between the first analyte and the second analyte in the biological sample.

Example 10—Determining a Location of an Interaction Between a First Analyte and a Second Analyte Using a Padlock Oligonucleotide FIG. 17 shows an exemplary method for determining abundance of an interaction between a first analyte and a second analyte in a biological sample using a padlock oligonucleotide. The first oligonucleotide 1701 that is bound to the first analyte-binding moiety 1702 includes from 5' to 3' a functional sequence 1703, a first barcode 1704, and a first bridge sequence 1705. The second oligonucleotide 1706 that is bound to the second analyte-binding moiety 1707 includes from 3' to 5' an optional capture probe capture domain sequence 1708, a second barcode 1709, and a second bridge sequence 1710. The first oligonucleotide is bound to the first analyte-binding moiety via a first cleavable linker 1711, and the second oligonucleotide is bound to the second analyte-binding moiety via a second cleavable linker 1712.

After attaching the first and/or second analyte-binding moieties to the first and second analytes, the sample is washed to remove any unbound analyte-binding moieties. A wash step can be performed using any wash solution disclosed herein. After the washing step to remove any unbound analyte-binding moieties, the biological sample can be contacted with the padlock oligonucleotide 1713, which is allowed to hybridize to the first oligonucleotide and the second oligonucleotide.

The padlock oligonucleotide 1713 includes a first sequence 1714 that is substantially complementary to a portion of the first oligonucleotide 1705, a backbone sequence including a barcode 1715, and a second sequence 1716 that is substantially complementary to portion of the second oligonucleotide 1710, wherein the first oligonucleotide and the second oligonucleotide are adjacent in the biological sample. The padlock oligonucleotide is circularized using ligation.

A second wash step can be performed after hybridizing the padlock oligonucleotide to the first and second oligonucleotides and/or after circularizing the padlock oligonucleotide in order to remove any unbound padlock oligonucleotides. The padlock oligonucleotide is released from the first and second oligonucleotides and amplified using rolling circle amplification. The amplified circularized padlock oligonucleotide is detected and used to identify the location of the interaction between the first analyte and the second analyte in the biological sample.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining a location of an interaction between a protein and a nucleic acid in a tissue sample, the method comprising:
   (a) contacting the tissue sample with a substrate comprising a plurality of capture probes, wherein a capture probe of the plurality of capture probes comprises a spatial barcode and a capture domain;
   (b) attaching a first analyte-binding moiety to the protein, wherein the first analyte-binding moiety is bound to a first oligonucleotide comprising a first barcode that is unique to the interaction between the protein and the first analyte-binding moiety;
   (c) hybridizing a second oligonucleotide to the nucleic acid, wherein the second oligonucleotide comprises a capture probe capture domain sequence;
   (d) hybridizing a third oligonucleotide to the first oligonucleotide and to the second oligonucleotide;
   (e) washing the tissue sample to remove any third oligonucleotides that are unbound to the first oligonucleotide and/or the second oligonucleotide;
   (f) ligating the first oligonucleotide and the second oligonucleotide, thereby generating a ligation product comprising the first barcode and the capture probe capture domain sequence;
   (g) dissociating the third oligonucleotide from the first oligonucleotide and the second oligonucleotide;
   (h) while the capture domain of the capture probe is affixed to the substrate, hybridizing the capture probe capture domain sequence of the ligation product to the capture domain; and
   (i) determining (i) the sequence of the spatial barcode or a complement thereof; (ii) the sequence of the first barcode or a complement thereof, and (iii) a sequence of the second oligonucleotide that is complementary to the nucleic acid or a complement thereof; and using the determined sequences of (i), (ii), and (iii) to identify the location of the interaction between the protein and the nucleic acid in the tissue sample.

2. The method of claim 1, wherein the first oligonucleotide further comprises a first functional sequence.

3. The method of claim 1, wherein the second oligonucleotide further comprises a second functional sequence.

4. The method of claim 1, wherein the first oligonucleotide comprises a free 5' end and/or a free 3' end.

5. The method of claim 1, wherein the second oligonucleotide comprises a free 5' end and/or a free 3' end.

6. The method of claim 1, wherein the first analyte-binding moiety is a protein.

7. The method of claim 1, wherein the first analyte-binding moiety is associated with the first oligonucleotide via a first linker.

8. The method of claim 7, wherein the first linker is a cleavable linker, wherein the cleavable linker is a photo-cleavable linker, UV-cleavable linker, or an enzyme-cleavable linker.

9. The method of claim 1, wherein the protein is a transcription factor.

10. The method of claim 1, wherein the nucleic acid is RNA.

11. The method of claim 1, wherein the third oligonucleotide comprises a sequence of about 20 nucleotides to about 60 nucleotides.

12. The method of claim 1, wherein step (e) uses chemical ligation to generate the ligation product.

13. The method of claim 1, wherein step (e) uses enzymatic ligation to generate the ligation product, wherein the enzymatic ligation utilizes a ligase selected from a T4 RNA ligase (Rnl2), a PBCV-1 ligase, a single-stranded DNA ligase, or a T4 DNA ligase.

14. The method of claim 1, wherein the first oligonucleotide or the second oligonucleotide further comprises a primer sequence.

15. The method of claim 1, wherein the first oligonucleotide and/or the second oligonucleotide is a DNA oligonucleotide.

16. The method of claim 1, further comprising a releasing step comprising removing (i) the first oligonucleotide from the first analyte-binding moiety.

17. The method of claim 1, further comprising releasing the ligation product from the nucleic acid, wherein releasing comprises contacting the tissue sample with an endoribonuclease.

18. The method of claim 17, wherein the endoribonuclease is an RNase H enzyme.

19. The method of claim 1, further comprising extending a 3' end of the capture probe using the ligation product as a template to generate an extended capture probe.

20. The method of claim 1, wherein the determining step comprises amplifying the ligation product bound to the capture domain, thereby generating an amplification product.

21. The method of claim 1, wherein the nucleic acid is DNA.

22. The method of claim 1, wherein the tissue sample is a fresh tissue sample or a frozen tissue sample.

23. The method of claim 1, wherein the tissue sample is a formalin-fixed, paraffin-embedded tissue sample.

24. The method of claim 1, wherein the tissue sample was previously stained using immunofluorescence, immunohistochemistry, hematoxylin, or eosin.

25. The method of claim 1, further comprising contacting the tissue sample with a permeabilization agent, wherein the permeabilization agent comprises proteinase K or pepsin.

26. The method of claim 1, wherein the capture probe further comprises one or more functional domains, a unique molecular identifier (UMI), a cleavage domain, or combinations thereof.

27. The method of claim 1, wherein the capture domain comprises a poly-uridine sequence or a poly-thymidine sequence.

28. The method of claim 1, further comprising determining an abundance of the interaction between the protein and the nucleic acid in the tissue sample.

* * * * *